US008163876B2

(12) United States Patent
Henry et al.

(10) Patent No.: US 8,163,876 B2
(45) Date of Patent: Apr. 24, 2012

(54) DNA SEQUENCES, VECTORS AND PROTEINS OF AVIAN INFLUENZA HEMAGGLUTININ

(75) Inventors: Matthew Henry, Indianapolis, IN (US); Ignacio M. Larrinua, Indianapolis, IN (US); Sean M. Russell, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 503 days.

(21) Appl. No.: 12/299,404

(22) PCT Filed: Jun. 8, 2007

(86) PCT No.: PCT/US2007/070755
§ 371 (c)(1),
(2), (4) Date: Nov. 3, 2008

(87) PCT Pub. No.: WO2007/149715
PCT Pub. Date: Dec. 27, 2007

(65) Prior Publication Data
US 2009/0106864 A1   Apr. 23, 2009

Related U.S. Application Data

(60) Provisional application No. 60/814,241, filed on Jun. 16, 2006.

(51) Int. Cl.
*A01H 5/00*    (2006.01)
*C07K 7/00*    (2006.01)
*A61K 39/00*   (2006.01)
*C12N 15/11*   (2006.01)
*C12N 15/00*   (2006.01)
*C12N 5/04*    (2006.01)

(52) U.S. Cl. ............ 530/350; 530/324; 424/186.1; 435/320.1; 435/419; 536/23.6

(58) Field of Classification Search .............. None
See application file for complete search history.

(56) References Cited

U.S. PATENT DOCUMENTS

2005/0048074 A1   3/2005   Cardineau et al.
2009/0106864 A1*  4/2009   Henry et al. .............. 800/298

FOREIGN PATENT DOCUMENTS

| WO | WO 2004/098533  | 11/2004  |
|----|-----------------|----------|
| WO | WO2004/098533 * | 11/2004  |
| WO | WO 2005/116260  | 12/2005  |
| WO | WO 2008/060669  | 5/2008   |

OTHER PUBLICATIONS

Guan et al. Hemagglutinin [Influenza A virus (A/Chicken/Hong Kong/822.1/01 (H5N1))]. (2003) GenBank Accession AAO52869; one page.*
Ducatez et al. (PNAS. Jan. 4, 2011; 108 (1): 349-354).*
Sequence alignment of SEQ ID No. 2 with SEQ ID No. 18 of Cardineau et al. Feb. 2005.*
Sequence alignment of instant SEQ ID No. 2 with SEQ ID No. 4 of WO 2004/098530 of Miller et al.*
Database Geneseq, Accession No. ARV40008, Jul. 24, 2008, XP-002579072, pp. 1-2.
Database Geneseq, Accession No. ADU69204, "Avian influenza virus HA (hemagglutination antigen) protein" Feb. 10, 2005, XP-002579073, p. 1.
Database Geneseq, Accession No. ADU69210, "Vector pCHA DNA related to AIV hemagglutination antigen" Feb. 10, 2005, XP-002579074, pp. 1-3.

* cited by examiner

*Primary Examiner* — Shanon A Foley
(74) *Attorney, Agent, or Firm* — Ronald S. Maciak; Saliwanchik, Lloyd & Eisenschenk

(57) ABSTRACT

The subject invention provides novel amino acid sequences (including a consensus sequence) of the Avian Influenza A virus hemagglutinin protein. These newly constructed genes are designed to provide a broader spectrum of activity across the serotype family thus providing a basis for a vaccine that has broad heterologous disease protection. The novel genes have been further improved by the addition of strategic glycosylation sites into the amino acids sequences that they encode. These genes can also, optionally, be codon optimized for plant expression, inserted into the appropriate vector and cloned into plants for expression. Polypeptides produced by recombinant host cells or transgenic plants can also be used as source of antigen for the formulation of vaccines for the control of influenza in susceptible individuals. Additionally, transgenic plant material may also be used as source of antigen for the formulation of vaccines for the control of influenza in susceptible individuals.

8 Claims, 20 Drawing Sheets

| ALLELE: HLA-A1 | | | |
|---|---|---|---|
| Rank | Sequence | At Position | SEQ ID NO: |
| 1 | KGDQICI | 15 | 21 |
| 2 | IGECPKY | 315 | 22 |
| 3 | IPEIATRP | 226 | 23 |
| 4 | AAEQTKL | 200 | 24 |
| 5 | FIAPEYA | 263 | 25 |
| ALLELE: HLA-A2 | | | |
| Rank | Sequence | At Position | SEQ ID NO: |
| 1 | PMCDEF | 81 | 26 |
| 2 | PKYVKSD | 319 | 27 |
| 3 | PLILRDC | 65 | 28 |
| 4 | GKLCSLN | 55 | 29 |
| 5 | KIVKKGD | 271 | 30 |
| ALLELE: HLA-A*0201 | | | |
| Rank | Sequence | At Position | SEQ ID NO: |
| 1 | TIGECPK | 314 | 31 |
| 2 | TIMEKNV | 34 | 32 |
| 3 | VLATGLR | 328 | 33 |
| 4 | VIALAIISV | 5 | 38 |
| 5 | YIVEKDN | 94 | 34 |
| ALLELE: HLA-A*0205 | | | |
| Rank | Sequence | At Position | SEQ ID NO: |
| 1 | YVSVGTS | 213 | 35 |
| 2 | TIMEKNV | 34 | 32 |
| 3 | NVPEWS | 88 | 36 |
| 4 | RMEFFW | 241 | 37 |
| 5 | YIVEKDN | 94 | 34 |

FIG. 1

| ALLELE: DRB1_0101 | | | |
|---|---|---|---|
| Rank | Sequence | At Position | Score | SEQ ID NO: |
| 1 | IVIALAIIS | 3 | 2.9 | 39 |
| 2 | FHNIHPLTI | 306 | 2.6 | 42 |
| 3 | WTILKPNDA | 245 | 2.3 | 87 |
| 4 | LLILWGIHH | 187 | 1.6 | 61 |
| 5 | YVSVGTSTL | 212 | 1.35 | 98 |
| 6 | WGIHHPNDA | 191 | 1.2 | 84 |
| 7 | FFRNVVWLI | 158 | 1.06 | 41 |
| 8 | LVLATGLRN | 326 | 0.9 | 67 |
| 9 | LKPNDAINF | 248 | 0.64 | 60 |
| 10 | LNGVKPLIL | 59 | 0.55 | 63 |

| ALLELE: DRB1_0102 | | | |
|---|---|---|---|
| Rank | Sequence | At Position | Score | SEQ ID NO: |
| 1 | IVIALAIIS | 3 | 3.9 | 39 |
| 2 | LLILWGIHH | 187 | 2.6 | 61 |
| 3 | FHNIHPLTI | 306 | 2.6 | 42 |
| 4 | LVLATGLRN | 326 | 1.9 | 67 |
| 5 | LKPNDAINF | 248 | 1.64 | 60 |
| 6 | LNGVKPLIL | 59 | 1.55 | 63 |
| 7 | IKKNNAYPT | 166 | 1.44 | 51 |
| 8 | WTILKPNDA | 245 | 1.3 | 87 |
| 9 | IAPEYAYKI | 263 | 1.1 | 45 |
| 10 | FFRNVVWLI | 158 | 1.06 | 41 |

| ALLELE: DRB1_0301 | | | |
|---|---|---|---|
| Rank | Sequence | At Position | Score | SEQ ID NO: |
| 1 | IVIALAIIS | 3 | 5.1 | 39 |
| 2 | VKGDQICIG | 13 | 4.7 | 75 |
| 3 | ILRDCSVAG | 66 | 4.5 | 53 |
| 4 | VEKDNPINS | 95 | 4.4 | 73 |
| 5 | YKIVKKGDS | 269 | 4.1 | 93 |
| 6 | VKSDRLVLA | 321 | 4 | 77 |
| 7 | LAIISVVKG | 7 | 3.8 | 56 |
| 8 | VVKGDQICI | 12 | 3.3 | 81 |
| 9 | IQIIPRSSW | 129 | 3.27 | 55 |
| 10 | LTIGECPKY | 312 | 3 | 66 |

| ALLELE: DRB1_0305 | | | |
|---|---|---|---|
| Rank | Sequence | At Position | Score | SEQ ID NO: |
| 1 | YKIVKKGDS | 269 | 4.7 | 93 |
| 2 | IVIALAIIS | 3 | 3.7 | 39 |
| 3 | VEKDNPINS | 95 | 3 | 73 |
| 4 | VKSDRLVLA | 321 | 3 | 77 |
| 5 | YVKSDRLVL | 320 | 3 | 97 |
| 6 | WGIHHPNDA | 191 | 2.41 | 84 |
| 7 | WLLGNPMCD | 75 | 2.4 | 86 |
| 8 | VKGDQICIG | 13 | 2.3 | 75 |
| 9 | IQIIPRSSW | 129 | 2.27 | 55 |
| 10 | FHNIHPLTI | 306 | 2.2 | 42 |

| ALLELE: DRB1_0306 | | | |
|---|---|---|---|
| Rank | Sequence | At Position | Score | SEQ ID NO: |
| 1 | IVIALAIIS | 3 | 4.38 | 39 |
| 2 | VKSDRLVLA | 321 | 3.88 | 77 |
| 3 | VEKDNPINS | 95 | 3.68 | 73 |
| 4 | VWLIKKNNA | 163 | 3.3 | 83 |
| 5 | VKGDQICIG | 13 | 3.3 | 75 |
| 6 | IQIIPRSSW | 129 | 3 | 55 |
| 7 | ILRDCSVAG | 66 | 2.98 | 53 |
| 8 | YVKSDRLVL | 320 | 2.5 | 97 |
| 9 | YKIVKKGDS | 269 | 2.3 | 93 |
| 10 | LAIISVVKG | 7 | 2.28 | 56 |

| ALLELE: DRB1_0307 | | | |
|---|---|---|---|
| Rank | Sequence | At Position | Score | SEQ ID NO: |
| 1 | IVIALAIIS | 3 | 4.38 | 39 |
| 2 | VKSDRLVLA | 321 | 3.88 | 77 |
| 3 | VEKDNPINS | 95 | 3.68 | 73 |
| 4 | VWLIKKNNA | 163 | 3.3 | 83 |
| 5 | VKGDQICIG | 13 | 3.3 | 75 |
| 6 | IQIIPRSSW | 129 | 3 | 55 |
| 7 | ILRDCSVAG | 66 | 2.98 | 53 |
| 8 | YVKSDRLVL | 320 | 2.5 | 97 |
| 9 | YKIVKKGDS | 269 | 2.3 | 93 |
| 10 | LAIISVVKG | 7 | 2.28 | 56 |

| ALLELE: DRB1_0308 | | | |
|---|---|---|---|
| Rank | Sequence | At Position | Score | SEQ ID NO: |
| 1 | IVIALAIIS | 3 | 4.38 | 39 |
| 2 | VKSDRLVLA | 321 | 3.88 | 77 |
| 3 | VEKDNPINS | 95 | 3.68 | 73 |
| 4 | VWLIKKNNA | 163 | 3.3 | 83 |
| 5 | VKGDQICIG | 13 | 3.3 | 75 |
| 6 | IQIIPRSSW | 129 | 3 | 55 |
| 7 | ILRDCSVAG | 66 | 2.98 | 53 |
| 8 | YVKSDRLVL | 320 | 2.5 | 97 |
| 9 | YKIVKKGDS | 269 | 2.3 | 93 |
| 10 | LAIISVVKG | 7 | 2.28 | 56 |

| ALLELE: DRB1_0309 | | | |
|---|---|---|---|
| Rank | Sequence | At Position | Score | SEQ ID NO: |
| 1 | YKIVKKGDS | 269 | 5.1 | 93 |
| 2 | IVIALAIIS | 3 | 4.1 | 39 |
| 3 | YVKSDRLVL | 320 | 3.96 | 97 |
| 4 | VKGDQICIG | 13 | 3.7 | 75 |
| 5 | ILRDCSVAG | 66 | 3.5 | 53 |
| 6 | WLLGNPMCD | 75 | 3.5 | 86 |
| 7 | VEKDNPINS | 95 | 3.4 | 73 |
| 8 | YVSVGTSTL | 212 | 3.13 | 98 |
| 9 | FHNIHPLTI | 306 | 3.1 | 42 |
| 10 | VKSDRLVLA | 321 | 3 | 77 |

| ALLELE: DRB1_0311 | | | |
|---|---|---|---|
| Rank | Sequence | At Position | Score | SEQ ID NO: |
| 1 | IVIALAIIS | 3 | 4.38 | 39 |
| 2 | VKSDRLVLA | 321 | 3.88 | 77 |
| 3 | VEKDNPINS | 95 | 3.68 | 73 |
| 4 | VWLIKKNNA | 163 | 3.3 | 83 |
| 5 | VKGDQICIG | 13 | 3.3 | 75 |
| 6 | IQIIPRSSW | 129 | 3 | 55 |
| 7 | ILRDCSVAG | 66 | 2.98 | 53 |
| 8 | YVKSDRLVL | 320 | 2.5 | 97 |
| 9 | YKIVKKGDS | 269 | 2.3 | 93 |
| 10 | LAIISVVKG | 7 | 2.28 | 56 |

| ALLELE: DRB1_0401 | | | |
|---|---|---|---|
| Rank | Sequence | At Position | Score | SEQ ID NO: |
| 1 | WGIHHPNDA | 191 | 3.7 | 84 |
| 2 | IVIALAIIS | 3 | 3.38 | 39 |
| 3 | YHANNSTEQ | 22 | 3.1 | 91 |
| 4 | YGNCNTKCQ | 286 | 3.1 | 90 |
| 5 | WTILKPNDA | 245 | 2.9 | 87 |
| 6 | FHNIHPLTI | 306 | 2.5 | 42 |
| 7 | YIVEKDNPI | 93 | 2.3 | 92 |
| 8 | ILRDCSVAG | 66 | 2.18 | 53 |
| 9 | YVSVGTSTL | 212 | 2.1 | 98 |
| 10 | IKRSYNNTN | 175 | 2.1 | 52 |

| ALLELE: DRB1_0402 | | | |
|---|---|---|---|
| Rank | Sequence | At Position | Score | SEQ ID NO: |
| 1 | IVIALAIIS | 3 | 4.8 | 39 |
| 2 | VPQRETRRQ | 335 | 4.6 | 79 |
| 3 | IIPRSSWSN | 131 | 3.4 | 49 |
| 4 | MEFFWTILK | 241 | 3.3 | 69 |
| 5 | IGYHANNST | 20 | 3.2 | 47 |
| 6 | YQNPTTYVS | 206 | 2.9 | 96 |
| 7 | WGIHHPNDA | 191 | 2.8 | 84 |
| 8 | LILWGIHHP | 188 | 2.8 | 58 |
| 9 | LILRDCSVA | 65 | 2.7 | 57 |
| 10 | WLIKKNNAY | 164 | 2.5 | 85 |

| ALLELE: DRB1_0404 | | | |
|---|---|---|---|
| Rank | Sequence | At Position | Score | SEQ ID NO: |
| 1 | IVIALAIIS | 3 | 4.38 | 39 |
| 2 | MEFFWTILK | 241 | 3.58 | 69 |
| 3 | YVSVGTSTL | 212 | 3.2 | 98 |
| 4 | LKHLLSSTN | 116 | 2.4 | 59 |
| 5 | LAIISVVKG | 7 | 2.4 | 56 |
| 6 | WTILKPNDA | 245 | 2.2 | 87 |
| 7 | LLILWGIHH | 187 | 2.16 | 61 |
| 8 | YQNPTTYVS | 206 | 1.8 | 96 |
| 9 | MERIVIALA | 0 | 1.8 | 71 |
| 10 | LYQNPTTYV | 205 | 1.8 | 68 |

| ALLELE: DRB1_0405 | | | |
|---|---|---|---|
| Rank | Sequence | At Position | Score | SEQ ID NO: |
| 1 | YVSVGTSTL | 212 | 5.2 | 98 |
| 2 | LKHLLSSTN | 116 | 3.4 | 59 |
| 3 | IVIALAIIS | 3 | 3.38 | 39 |
| 4 | WTILKPNDA | 245 | 3.2 | 87 |
| 5 | WLIKKNNAY | 164 | 3.1 | 85 |
| 6 | YGNCNTKCQ | 286 | 2.9 | 90 |
| 7 | YQNPTTYVS | 206 | 2.8 | 96 |
| 8 | YHANNSTEQ | 22 | 2.8 | 91 |
| 9 | IKRSYNNTN | 175 | 2.7 | 52 |
| 10 | LAIISVVKG | 7 | 2.7 | 56 |

| ALLELE: DRB1_0408 | | | |
|---|---|---|---|
| Rank | Sequence | At Position | Score | SEQ ID NO: |
| 1 | YVSVGTSTL | 212 | 4.2 | 98 |
| 2 | IVIALAIIS | 3 | 3.38 | 39 |
| 3 | WTILKPNDA | 245 | 3.2 | 87 |
| 4 | YQNPTTYVS | 206 | 2.8 | 96 |
| 5 | MEFFWTILK | 241 | 2.58 | 69 |
| 6 | FHNIHPLTI | 306 | 2.4 | 42 |
| 7 | FRNVVWLIK | 159 | 2.2 | 43 |
| 8 | YGNCNTKCQ | 286 | 2.1 | 90 |
| 9 | WLIKKNNAY | 164 | 2 | 85 |
| 10 | YHANNSTEQ | 22 | 2 | 91 |

| ALLELE: DRB1_0410 | | | |
|---|---|---|---|
| Rank | Sequence | At Position | Score | SEQ ID NO: |
| 1 | LKHLLSSTN | 116 | 4.4 | 59 |
| 2 | IVIALAIIS | 3 | 4.38 | 39 |
| 3 | YVSVGTSTL | 212 | 4.2 | 98 |
| 4 | LAIISVVKG | 7 | 3.7 | 56 |
| 5 | IKRSYNNTN | 175 | 3.7 | 52 |
| 6 | LLILWGIHH | 187 | 3.38 | 61 |
| 7 | MEFFWTILK | 241 | 2.88 | 69 |
| 8 | LLSSTNHFE | 119 | 2.7 | 62 |
| 9 | MEKNVTVTH | 35 | 2.5 | 70 |
| 10 | LVLATGLRN | 326 | 2.5 | 67 |

| ALLELE: DRB1_0421 | | | |
|---|---|---|---|
| Rank | Sequence | At Position | Score | SEQ ID NO: |
| 1 | IVIALAIIS | 3 | 3.78 | 39 |
| 2 | WGIHHPNDA | 191 | 3.7 | 84 |
| 3 | ILRDCSVAG | 66 | 3.58 | 53 |
| 4 | FHNIHPLTI | 306 | 3.4 | 42 |
| 5 | YIVEKDNPI | 93 | 3.2 | 92 |
| 6 | YVSVGTSTL | 212 | 3.06 | 98 |
| 7 | WLIKKNNAY | 164 | 3 | 85 |
| 8 | INFESNGNF | 254 | 3 | 54 |
| 9 | WTILKPNDA | 245 | 2.9 | 87 |
| 10 | IKRSYNNTN | 175 | 2.9 | 52 |

| ALLELE: DRB1_0423 | | | |
|---|---|---|---|
| Rank | Sequence | At Position | Score | SEQ ID NO: |
| 1 | IVIALAIIS | 3 | 4.38 | 39 |
| 2 | MEFFWTILK | 241 | 3.58 | 69 |
| 3 | YVSVGTSTL | 212 | 3.2 | 98 |
| 4 | LKHLLSSTN | 116 | 2.4 | 59 |
| 5 | LAIISVVKG | 7 | 2.4 | 56 |
| 6 | WTILKPNDA | 245 | 2.2 | 87 |
| 7 | LLILWGIHH | 187 | 2.16 | 61 |
| 8 | YQNPTTYVS | 206 | 1.8 | 96 |
| 9 | MERIVIALA | 0 | 1.8 | 71 |
| 10 | LYQNPTTYV | 205 | 1.8 | 68 |

| ALLELE: DRB1_0426 | | | |
|---|---|---|---|
| Rank | Sequence | At Position | Score | SEQ ID NO: |
| 1 | WGIHHPNDA | 191 | 3.7 | 84 |
| 2 | IVIALAIIS | 3 | 3.38 | 39 |
| 3 | YHANNSTEQ | 22 | 3.1 | 91 |
| 4 | YGNCNTKCQ | 286 | 3.1 | 90 |
| 5 | WTILKPNDA | 245 | 2.9 | 87 |
| 6 | FHNIHPLTI | 306 | 2.5 | 42 |
| 7 | YIVEKDNPI | 93 | 2.3 | 92 |
| 8 | ILRDCSVAG | 66 | 2.18 | 53 |
| 9 | YVSVGTSTL | 212 | 2.1 | 98 |
| 10 | IKRSYNNTN | 175 | 2.1 | 52 |

FIG. 2 (continued)

ALLELE: DRB1_0701

| Rank | Sequence | At Position | Score | SEQ ID NO: |
|---|---|---|---|---|
| 1 | YVKSDRLVL | 320 | 8.1 | 97 |
| 2 | FHNIHPLTI | 306 | 7.5 | 42 |
| 3 | YVSVGTSTL | 212 | 6.92 | 98 |
| 4 | LNGVKPLIL | 59 | 6 | 63 |
| 5 | YNNTNQEDL | 179 | 5.9 | 95 |
| 6 | VTVTHAQDI | 39 | 5.4 | 80 |
| 7 | FFRNVVWLI | 158 | 5.3 | 41 |
| 8 | IVIALAIIS | 3 | 4.7 | 39 |
| 9 | VVKGDQICI | 12 | 4.7 | 81 |
| 10 | LKPNDAINF | 248 | 3.8 | 60 |

ALLELE: DRB1_0703

| Rank | Sequence | At Position | Score | SEQ ID NO: |
|---|---|---|---|---|
| 1 | YVKSDRLVL | 320 | 8.1 | 97 |
| 2 | FHNIHPLTI | 306 | 7.5 | 42 |
| 3 | YVSVGTSTL | 212 | 6.92 | 98 |
| 4 | LNGVKPLIL | 59 | 6 | 63 |
| 5 | YNNTNQEDL | 179 | 5.9 | 95 |
| 6 | VTVTHAQDI | 39 | 5.4 | 80 |
| 7 | FFRNVVWLI | 158 | 5.3 | 41 |
| 8 | IVIALAIIS | 3 | 4.7 | 39 |
| 9 | VVKGDQICI | 12 | 4.7 | 81 |
| 10 | LKPNDAINF | 248 | 3.8 | 60 |

ALLELE: DRB1_0801

| Rank | Sequence | At Position | Score | SEQ ID NO: |
|---|---|---|---|---|
| 1 | YKIVKKGDS | 269 | 4.4 | 93 |
| 2 | YAYKIVKKG | 267 | 3.8 | 88 |
| 3 | WLIKKNNAY | 164 | 3 | 85 |
| 4 | VVWLIKKNN | 162 | 2.9 | 82 |
| 5 | IISVVKGDQ | 9 | 2.7 | 50 |
| 6 | IVIALAIIS | 3 | 2.5 | 39 |
| 7 | VPQRETRRQ | 335 | 2.3 | 79 |
| 8 | YGNCNTKCQ | 286 | 2.3 | 90 |
| 9 | WLLGNPMCD | 75 | 2.2 | 86 |
| 10 | YVSVGTSTL | 212 | 2.1 | 98 |

ALLELE: DRB1_0802

| Rank | Sequence | At Position | Score | SEQ ID NO: |
|---|---|---|---|---|
| 1 | YKIVKKGDS | 269 | 4.4 | 93 |
| 2 | YAYKIVKKG | 267 | 2.5 | 88 |
| 3 | IVIALAIIS | 3 | 2.5 | 39 |
| 4 | LILRDCSVA | 65 | 2.1 | 57 |
| 5 | WLIKKNNAY | 164 | 1.9 | 85 |
| 6 | IISVVKGDQ | 9 | 1.9 | 50 |
| 7 | FHNIHPLTI | 306 | 1.5 | 42 |
| 8 | YGNCNTKCQ | 286 | 1.5 | 90 |
| 9 | VPQRETRRQ | 335 | 1.5 | 79 |
| 10 | WTILKPNDA | 245 | 1.4 | 87 |

ALLELE: DRB1_0804

| Rank | Sequence | At Position | Score | SEQ ID NO: |
|---|---|---|---|---|
| 1 | IVIALAIIS | 3 | 3.5 | 39 |
| 2 | YKIVKKGDS | 269 | 3.4 | 93 |
| 3 | LILRDCSVA | 65 | 3.1 | 57 |
| 4 | IISVVKGDQ | 9 | 2.9 | 50 |
| 5 | VPQRETRRQ | 335 | 2.5 | 79 |
| 6 | LNQRSIPEI | 220 | 2.3 | 64 |
| 7 | IHPLTIGEC | 309 | 2 | 48 |
| 8 | VVWLIKKNN | 162 | 1.9 | 82 |
| 9 | MERIVIALA | 0 | 1.8 | 71 |
| 10 | LLILWGIHH | 187 | 1.78 | 61 |

ALLELE: DRB1_0806

| Rank | Sequence | At Position | Score | SEQ ID NO: |
|---|---|---|---|---|
| 1 | VVWLIKKNN | 162 | 3.9 | 82 |
| 2 | IISVVKGDQ | 9 | 3.7 | 50 |
| 3 | IVIALAIIS | 3 | 3.5 | 39 |
| 4 | YKIVKKGDS | 269 | 3.4 | 93 |
| 5 | VPQRETRRQ | 335 | 3.3 | 79 |
| 6 | LILRDCSVA | 65 | 3.1 | 57 |
| 7 | LLILWGIHH | 187 | 3 | 61 |
| 8 | IIPRSSWSN | 131 | 3 | 49 |
| 9 | YAYKIVKKG | 267 | 2.8 | 88 |
| 10 | IATRPKVNG | 228 | 2.8 | 46 |

FIG. 2 (continued)

| ALLELE: DRB1_0813 | | | |
|---|---|---|---|
| Rank | Sequence | At Position | Score | SEQ ID NO: |
| 1 | WLIKKNNAY | 164 | 3.9 | 85 |
| 2 | LILRDCSVA | 65 | 3.9 | 57 |
| 3 | YKIVKKGDS | 269 | 3.7 | 93 |
| 4 | WTILKPNDA | 245 | 3.4 | 87 |
| 5 | IVIALAIIS | 3 | 3.38 | 39 |
| 6 | YVSVGTSTL | 212 | 2.9 | 98 |
| 7 | IQIIPRSSW | 129 | 2.5 | 55 |
| 8 | VVWLIKKNA | 163 | 2.2 | 83 |
| 9 | WGIHHPNDA | 191 | 2.2 | 84 |
| 10 | YNGRSSFFR | 152 | 2.15 | 94 |

| ALLELE: DRB1_0817 | | | |
|---|---|---|---|
| Rank | Sequence | At Position | Score | SEQ ID NO: |
| 1 | YKIVKKGDS | 269 | 4.5 | 93 |
| 2 | YAYKIVKKG | 267 | 4.4 | 88 |
| 3 | IVIALAIIS | 3 | 4.1 | 39 |
| 4 | WLLGNPMCD | 75 | 3.8 | 86 |
| 5 | YVKSDRLVL | 320 | 3.6 | 97 |
| 6 | LLILWGIHH | 187 | 3.6 | 61 |
| 7 | FHNIHPLTI | 306 | 3.5 | 42 |
| 8 | VVWLIKKNN | 162 | 3.5 | 82 |
| 9 | LVLATGLRN | 326 | 3.5 | 67 |
| 10 | WLIKKNNAY | 164 | 3.3 | 85 |

| ALLELE: DRB1_1101 | | | |
|---|---|---|---|
| Rank | Sequence | At Position | Score | SEQ ID NO: |
| 1 | YKIVKKGDS | 269 | 4.6 | 93 |
| 2 | IVIALAIIS | 3 | 4.1 | 39 |
| 3 | FHNIHPLTI | 306 | 3.9 | 42 |
| 4 | YVKSDRLVL | 320 | 2.9 | 97 |
| 5 | FRNVVWLIK | 159 | 2.9 | 43 |
| 6 | LLILWGIHH | 187 | 2.78 | 61 |
| 7 | YEELKHLLS | 113 | 2.1 | 89 |
| 8 | YGNCNTKCQ | 286 | 2.1 | 90 |
| 9 | WTILKPNDA | 245 | 2.1 | 87 |
| 10 | IISVVKGDQ | 9 | 2.1 | 50 |

| ALLELE: DRB1_1102 | | | |
|---|---|---|---|
| Rank | Sequence | At Position | Score | SEQ ID NO: |
| 1 | IVIALAIIS | 3 | 3.8 | 39 |
| 2 | VKPLILRDC | 62 | 3.2 | 76 |
| 3 | WGIHHPNDA | 191 | 3.1 | 84 |
| 4 | LILWGIHHP | 188 | 2.5 | 58 |
| 5 | VVWLIKKNN | 162 | 2.4 | 82 |
| 6 | VPQRETRRQ | 335 | 2.2 | 79 |
| 7 | FFRNVVWLI | 158 | 1.9 | 41 |
| 8 | MPFHNIHPL | 304 | 1.8 | 72 |
| 9 | LLILWGIHH | 187 | 1.78 | 61 |
| 10 | MEFFWTILK | 241 | 1.7 | 69 |

| ALLELE: DRB1_1104 | | | |
|---|---|---|---|
| Rank | Sequence | At Position | Score | SEQ ID NO: |
| 1 | IVIALAIIS | 3 | 5.1 | 39 |
| 2 | LLILWGIHH | 187 | 3.78 | 61 |
| 3 | YKIVKKGDS | 269 | 3.6 | 93 |
| 4 | IISVVKGDQ | 9 | 3.1 | 50 |
| 5 | VIALAIISV | 4 | 3 | 74 |
| 6 | VVWLIKKNN | 162 | 2.9 | 82 |
| 7 | FHNIHPLTI | 306 | 2.9 | 42 |
| 8 | MEFFWTILK | 241 | 2.6 | 69 |
| 9 | LVLATGLRN | 326 | 2.5 | 67 |
| 10 | IHPLTIGEC | 309 | 2.5 | 48 |

| ALLELE: DRB1_1106 | | | |
|---|---|---|---|
| Rank | Sequence | At Position | Score | SEQ ID NO: |
| 1 | IVIALAIIS | 3 | 5.1 | 39 |
| 2 | LLILWGIHH | 187 | 3.78 | 61 |
| 3 | YKIVKKGDS | 269 | 3.6 | 93 |
| 4 | IISVVKGDQ | 9 | 3.1 | 50 |
| 5 | VIALAIISV | 4 | 3 | 74 |
| 6 | VVWLIKKNN | 162 | 2.9 | 82 |
| 7 | FHNIHPLTI | 306 | 2.9 | 42 |
| 8 | MEFFWTILK | 241 | 2.6 | 69 |
| 9 | LVLATGLRN | 326 | 2.5 | 67 |
| 10 | IHPLTIGEC | 309 | 2.5 | 48 |

FIG. 2 (continued)

| ALLELE: DRB1_1107 | | | |
|---|---|---|---|
| Rank | Sequence | At Position | Score | SEQ ID NO: |
| 1 | IVIALAIIS | 3 | 4.7 | 39 |
| 2 | VEKDNPINS | 95 | 4 | 73 |
| 3 | VKSDRLVLA | 321 | 4 | 77 |
| 4 | YKIVKKGDS | 269 | 3.7 | 93 |
| 5 | VKGDQICIG | 13 | 3.3 | 75 |
| 6 | IQIIPRSSW | 129 | 3.27 | 55 |
| 7 | IISVVKGDQ | 9 | 3.2 | 50 |
| 8 | ILRDCSVAG | 66 | 3.1 | 53 |
| 9 | VVWLIKKNNA | 163 | 2.61 | 83 |
| 10 | LAIISVVKG | 7 | 2.4 | 56 |

| ALLELE: DRB1_1114 | | | |
|---|---|---|---|
| Rank | Sequence | At Position | Score | SEQ ID NO: |
| 1 | WGIHHPNDA | 191 | 4.1 | 84 |
| 2 | FFRNVVWLI | 158 | 2.9 | 41 |
| 3 | IVIALAIIS | 3 | 2.8 | 39 |
| 4 | WTILKPNDA | 245 | 2.5 | 87 |
| 5 | YGNCNTKCQ | 286 | 2.3 | 90 |
| 6 | VKPLILRDC | 62 | 2.2 | 76 |
| 7 | YKIVKKGDS | 269 | 2.2 | 93 |
| 8 | YVKSDRLVL | 320 | 1.9 | 97 |
| 9 | WLIKKNNAY | 164 | 1.8 | 85 |
| 10 | YAYKIVKKG | 267 | 1.8 | 88 |

| ALLELE: DRB1_1120 | | | |
|---|---|---|---|
| Rank | Sequence | At Position | Score | SEQ ID NO: |
| 1 | WGIHHPNDA | 191 | 4.1 | 84 |
| 2 | FFRNVVWLI | 158 | 3.8 | 41 |
| 3 | YAYKIVKKG | 267 | 3.2 | 88 |
| 4 | IVIALAIIS | 3 | 3.2 | 39 |
| 5 | WLIKKNNAY | 164 | 3.1 | 85 |
| 6 | YVKSDRLVL | 320 | 2.86 | 97 |
| 7 | YKIVKKGDS | 269 | 2.6 | 93 |
| 8 | WTILKPNDA | 245 | 2.5 | 87 |
| 9 | LILWGIHHP | 188 | 2.5 | 58 |
| 10 | FHNIHPLTI | 306 | 2.2 | 42 |

| ALLELE: DRB1_1121 | | | |
|---|---|---|---|
| Rank | Sequence | At Position | Score | SEQ ID NO: |
| 1 | IVIALAIIS | 3 | 3.8 | 39 |
| 2 | VKPLILRDC | 62 | 3.2 | 76 |
| 3 | WGIHHPNDA | 191 | 3.1 | 84 |
| 4 | LILWGIHHP | 188 | 2.5 | 58 |
| 5 | VVWLIKKNN | 162 | 2.4 | 82 |
| 6 | VPQRETRRQ | 335 | 2.2 | 79 |
| 7 | FFRNVVWLI | 158 | 1.9 | 41 |
| 8 | MPFHNIHPL | 304 | 1.8 | 72 |
| 9 | LLILWGIHH | 187 | 1.78 | 61 |
| 10 | MEFFWTILK | 241 | 1.7 | 69 |

| ALLELE: DRB1_1128 | | | |
|---|---|---|---|
| Rank | Sequence | At Position | Score | SEQ ID NO: |
| 1 | YKIVKKGDS | 269 | 5 | 93 |
| 2 | FHNIHPLTI | 306 | 4.8 | 42 |
| 3 | IVIALAIIS | 3 | 4.5 | 39 |
| 4 | YVKSDRLVL | 320 | 3.86 | 97 |
| 5 | FEKIQIIPR | 126 | 3 | 40 |
| 6 | VIALAIISV | 4 | 3 | 74 |
| 7 | FRNVVWLIK | 159 | 3 | 43 |
| 8 | FFRNVVWLI | 158 | 2.9 | 41 |
| 9 | VVWLIKKNN | 162 | 2.7 | 82 |
| 10 | YEELKHLLS | 113 | 2.5 | 89 |

| ALLELE: DRB1_1301 | | | |
|---|---|---|---|
| Rank | Sequence | At Position | Score | SEQ ID NO: |
| 1 | IVIALAIIS | 3 | 4.2 | 39 |
| 2 | LILWGIHHP | 188 | 3.5 | 58 |
| 3 | VKPLILRDC | 62 | 3.2 | 76 |
| 4 | VVWLIKKNN | 162 | 3.2 | 82 |
| 5 | WGIHHPNDA | 191 | 3.1 | 84 |
| 6 | FFRNVVWLI | 158 | 2.8 | 41 |
| 7 | MPFHNIHPL | 304 | 2.76 | 72 |
| 8 | LAIISVVKG | 7 | 2.4 | 56 |
| 9 | YAYKIVKKG | 267 | 2.2 | 88 |
| 10 | LRNVPQRET | 332 | 2.2 | 65 |

FIG. 2 (continued)

ALLELE: DRB1_1302

| Rank | Sequence | At Position | Score | SEQ ID NO: |
|---|---|---|---|---|
| 1 | WGIHHPNDA | 191 | 4.1 | 84 |
| 2 | FFRNVVWLI | 158 | 3.8 | 41 |
| 3 | YAYKIVKKG | 267 | 3.2 | 88 |
| 4 | IVIALAIIS | 3 | 3.2 | 39 |
| 5 | WLIKKNNAY | 164 | 3.1 | 85 |
| 6 | YVKSDRLVL | 320 | 2.86 | 97 |
| 7 | YKIVKKGDS | 269 | 2.6 | 93 |
| 8 | WTILKPNDA | 245 | 2.5 | 87 |
| 9 | LILWGIHHP | 188 | 2.5 | 58 |
| 10 | FHNIHPLTI | 306 | 2.2 | 42 |

ALLELE: DRB1_1304

| Rank | Sequence | At Position | Score | SEQ ID NO: |
|---|---|---|---|---|
| 1 | VVWLIKKNN | 162 | 4.4 | 82 |
| 2 | IVIALAIIS | 3 | 3.8 | 39 |
| 3 | LVLATGLRN | 326 | 3.4 | 67 |
| 4 | VNGQSGRME | 234 | 3.4 | 78 |
| 5 | VKPLILRDC | 62 | 3.2 | 76 |
| 6 | WGIHHPNDA | 191 | 3.1 | 84 |
| 7 | VPQRETRRQ | 335 | 3 | 79 |
| 8 | LLILWGIHH | 187 | 3 | 61 |
| 9 | LILWGIHHP | 188 | 2.9 | 58 |
| 10 | MPFHNIHPL | 304 | 2.8 | 72 |

ALLELE: DRB1_1305

| Rank | Sequence | At Position | Score | SEQ ID NO: |
|---|---|---|---|---|
| 1 | YKIVKKGDS | 269 | 5 | 93 |
| 2 | FHNIHPLTI | 306 | 4.8 | 42 |
| 3 | IVIALAIIS | 3 | 4.5 | 39 |
| 4 | YVKSDRLVL | 320 | 3.86 | 97 |
| 5 | FEKIQIIPR | 126 | 3 | 40 |
| 6 | VIALAIISV | 4 | 3 | 74 |
| 7 | FRNVVWLIK | 159 | 3 | 43 |
| 8 | FFRNVVWLI | 158 | 2.9 | 41 |
| 9 | VVWLIKKNN | 162 | 2.7 | 82 |
| 10 | YEELKHLLS | 113 | 2.5 | 89 |

ALLELE: DRB1_1307

| Rank | Sequence | At Position | Score | SEQ ID NO: |
|---|---|---|---|---|
| 1 | YKIVKKGDS | 269 | 4.5 | 93 |
| 2 | IVIALAIIS | 3 | 2.5 | 39 |
| 3 | FHNIHPLTI | 306 | 2.1 | 42 |
| 4 | IISVVKGDQ | 9 | 2 | 50 |
| 5 | WTILKPNDA | 245 | 1.8 | 87 |
| 6 | YGNCNTKCQ | 286 | 1.5 | 90 |
| 7 | MERIVIALA | 0 | 1.4 | 71 |
| 8 | IHPLTIGEC | 309 | 1.4 | 48 |
| 9 | IQIIPRSSW | 129 | 1.3 | 55 |
| 10 | VVWLIKKNN | 162 | 1.3 | 82 |

ALLELE: DRB1_1311

| Rank | Sequence | At Position | Score | SEQ ID NO: |
|---|---|---|---|---|
| 1 | IVIALAIIS | 3 | 5.1 | 39 |
| 2 | LLILWGIHH | 187 | 3.78 | 61 |
| 3 | YKIVKKGDS | 269 | 3.6 | 93 |
| 4 | IISVVKGDQ | 9 | 3.1 | 50 |
| 5 | VIALAIISV | 4 | 3 | 74 |
| 6 | VVWLIKKNN | 162 | 2.9 | 82 |
| 7 | FHNIHPLTI | 306 | 2.9 | 42 |
| 8 | MEFFWTILK | 241 | 2.6 | 69 |
| 9 | LVLATGLRN | 326 | 2.5 | 67 |
| 10 | IHPLTIGEC | 309 | 2.5 | 48 |

ALLELE: DRB1_1321

| Rank | Sequence | At Position | Score | SEQ ID NO: |
|---|---|---|---|---|
| 1 | YKIVKKGDS | 269 | 4.6 | 93 |
| 2 | IVIALAIIS | 3 | 4.1 | 39 |
| 3 | FHNIHPLTI | 306 | 4.1 | 42 |
| 4 | LLILWGIHH | 187 | 4 | 61 |
| 5 | VVWLIKKNN | 162 | 3.9 | 82 |
| 6 | YVKSDRLVL | 320 | 3.9 | 97 |
| 7 | LVLATGLRN | 326 | 3.5 | 67 |
| 8 | WLLGNPMCD | 75 | 3.1 | 86 |
| 9 | FWTILKPND | 244 | 3.05 | 44 |
| 10 | IISVVKGDQ | 9 | 2.9 | 50 |

FIG. 2 (continued)

| ALLELE: DRB1_1322 | | | |
|---|---|---|---|
| Rank | Sequence | At Position | Score | SEQ ID NO: |
| 1 | IVIALAIIS | 3 | 3.8 | 39 |
| 2 | VKPLILRDC | 62 | 3.2 | 76 |
| 3 | WGIHHPNDA | 191 | 3.1 | 84 |
| 4 | LILWGIHHP | 188 | 2.5 | 58 |
| 5 | VVWLIKKNN | 162 | 2.4 | 82 |
| 6 | VPQRETRRQ | 335 | 2.2 | 79 |
| 7 | FFRNVVWLI | 158 | 1.9 | 41 |
| 8 | MPFHNIHPL | 304 | 1.8 | 72 |
| 9 | LLILWGIHH | 187 | 1.78 | 61 |
| 10 | MEFFWTILK | 241 | 1.7 | 69 |

| ALLELE: DRB1_1323 | | | |
|---|---|---|---|
| Rank | Sequence | At Position | Score | SEQ ID NO: |
| 1 | WGIHHPNDA | 191 | 4.1 | 84 |
| 2 | FFRNVVWLI | 158 | 2.9 | 41 |
| 3 | IVIALAIIS | 3 | 2.8 | 39 |
| 4 | WTILKPNDA | 245 | 2.5 | 87 |
| 5 | YGNCNTKCQ | 286 | 2.3 | 90 |
| 6 | VKPLILRDC | 62 | 2.2 | 76 |
| 7 | YKIVKKGDS | 269 | 2.2 | 93 |
| 8 | YVKSDRLVL | 320 | 1.9 | 97 |
| 9 | WLIKKNNAY | 164 | 1.8 | 85 |
| 10 | YAYKIVKKG | 267 | 1.8 | 88 |

| ALLELE: DRB1_1327 | | | |
|---|---|---|---|
| Rank | Sequence | At Position | Score | SEQ ID NO: |
| 1 | IVIALAIIS | 3 | 4.2 | 39 |
| 2 | LILWGIHHP | 188 | 3.5 | 58 |
| 3 | VKPLILRDC | 62 | 3.2 | 76 |
| 4 | VVWLIKKNN | 162 | 3.2 | 82 |
| 5 | WGIHHPNDA | 191 | 3.1 | 84 |
| 6 | FFRNVVWLI | 158 | 2.8 | 41 |
| 7 | MPFHNIHPL | 304 | 2.76 | 72 |
| 8 | LAIISVVKG | 7 | 2.4 | 56 |
| 9 | YAYKIVKKG | 267 | 2.2 | 88 |
| 10 | LRNVPQRET | 332 | 2.2 | 65 |

| ALLELE: DRB1_1328 | | | |
|---|---|---|---|
| Rank | Sequence | At Position | Score | SEQ ID NO: |
| 1 | IVIALAIIS | 3 | 4.2 | 39 |
| 2 | LILWGIHHP | 188 | 3.5 | 58 |
| 3 | VKPLILRDC | 62 | 3.2 | 76 |
| 4 | VVWLIKKNN | 162 | 3.2 | 82 |
| 5 | WGIHHPNDA | 191 | 3.1 | 84 |
| 6 | FFRNVVWLI | 158 | 2.8 | 41 |
| 7 | MPFHNIHPL | 304 | 2.76 | 72 |
| 8 | LAIISVVKG | 7 | 2.4 | 56 |
| 9 | YAYKIVKKG | 267 | 2.2 | 88 |
| 10 | LRNVPQRET | 332 | 2.2 | 65 |

| ALLELE: DRB1_1501 | | | |
|---|---|---|---|
| Rank | Sequence | At Position | Score | SEQ ID NO: |
| 1 | IVIALAIIS | 3 | 4.8 | 39 |
| 2 | LVLATGLRN | 326 | 4.3 | 67 |
| 3 | YVKSDRLVL | 320 | 4.2 | 97 |
| 4 | LLILWGIHH | 187 | 3.9 | 61 |
| 5 | IGYHANNST | 20 | 3.6 | 47 |
| 6 | VVKGDQICI | 12 | 3.5 | 81 |
| 7 | VIALAIISV | 4 | 3.45 | 74 |
| 8 | LNGVKPLIL | 59 | 3.4 | 63 |
| 9 | FHNIHPLTI | 306 | 3.3 | 42 |
| 10 | IQIIPRSSW | 129 | 3.2 | 55 |

| ALLELE: DRB1_1502 | | | |
|---|---|---|---|
| Rank | Sequence | At Position | Score | SEQ ID NO: |
| 1 | YVKSDRLVL | 320 | 5.2 | 97 |
| 2 | FHNIHPLTI | 306 | 4.3 | 42 |
| 3 | IVIALAIIS | 3 | 3.8 | 39 |
| 4 | WGIHHPNDA | 191 | 3.6 | 84 |
| 5 | LVLATGLRN | 326 | 3.3 | 67 |
| 6 | YVSVGTSTL | 212 | 3.26 | 98 |
| 7 | LLILWGIHH | 187 | 2.9 | 61 |
| 8 | FRNVVWLIK | 159 | 2.7 | 43 |
| 9 | IGYHANNST | 20 | 2.6 | 47 |
| 10 | VVKGDQICI | 12 | 2.5 | 81 |

FIG. 2 (continued)

| ALLELE: DRB1_1506 | | | |
|---|---|---|---|
| Rank | Sequence | At Position | Score | SEQ ID NO: |
| 1 | IVIALAIIS | 3 | 4.8 | 39 |
| 2 | LVLATGLRN | 326 | 4.3 | 67 |
| 3 | YVKSDRLVL | 320 | 4.2 | 97 |
| 4 | LLILWGIHH | 187 | 3.9 | 61 |
| 5 | IGYHANNST | 20 | 3.6 | 47 |
| 6 | VVKGDQICI | 12 | 3.5 | 81 |
| 7 | VIALAIISV | 4 | 3.45 | 74 |
| 8 | LNGVKPLIL | 59 | 3.4 | 63 |
| 9 | FHNIHPLTI | 306 | 3.3 | 42 |
| 10 | IQIIPRSSW | 129 | 3.2 | 55 |
| ALLELE: DRB5_0101 | | | |
| Rank | Sequence | At Position | Score | SEQ ID NO: |
| 1 | FRNVVWLIK | 159 | 5.4 | 43 |
| 2 | FHNIHPLTI | 306 | 4.6 | 42 |
| 3 | IVIALAIIS | 3 | 4.5 | 39 |
| 4 | LLILWGIHH | 187 | 4 | 61 |
| 5 | YVSVGTSTL | 212 | 3.7 | 98 |
| 6 | FEKIQIIPR | 126 | 3.7 | 40 |
| 7 | YKIVKKGDS | 269 | 3.5 | 93 |
| 8 | LNGVKPLIL | 59 | 3.2 | 63 |
| 9 | WTILKPNDA | 245 | 2.8 | 87 |
| 10 | YNGRSSFFR | 152 | 2.8 | 94 |
| ALLELE: DRB5_0105 | | | |
| Rank | Sequence | At Position | Score | SEQ ID NO: |
| 1 | FRNVVWLIK | 159 | 5.4 | 43 |
| 2 | FHNIHPLTI | 306 | 4.6 | 42 |
| 3 | IVIALAIIS | 3 | 4.5 | 39 |
| 4 | LLILWGIHH | 187 | 4 | 61 |
| 5 | YVSVGTSTL | 212 | 3.7 | 98 |
| 6 | FEKIQIIPR | 126 | 3.7 | 40 |
| 7 | YKIVKKGDS | 269 | 3.5 | 93 |
| 8 | LNGVKPLIL | 59 | 3.2 | 63 |
| 9 | WTILKPNDA | 245 | 2.8 | 87 |
| 10 | YNGRSSFFR | 152 | 2.8 | 94 |

FIG. 2 (continued)

| Peptide No. | Start Position | End Position | Peptide Derived from SEQ ID NO: 13 | Peptide Length | SEQ ID NO: |
|---|---|---|---|---|---|
| 1 | 24 | 31 | HANNSTEQ | 8 | 99 |
| 2 | 109 | 117 | GDFNDYEEL | 9 | 100 |
| 3 | 136 | 142 | SSWSNHD | 7 | 101 |
| 4 | 174 | 186 | PTIKRSYNNTNQE | 13 | 102 |
| 5 | 196 | 212 | HPNDAAEQTKLYQNPTT | 17 | 103 |
| 6 | 229 | 236 | IATRPKVN | 8 | 104 |
| 7 | 335 | 345 | NVPQRETRRQK | 11 | 105 |
| 8 | 4 | 23 | IVIALAIISVVKGDQICIGY | 20 | 106 |
| 9 | 39 | 48 | NVTVTHAQDI | 10 | 107 |
| 10 | 55 | 76 | GKLCSLNGVKPLILRDCSVAGW | 22 | 108 |
| 11 | 84 | 99 | DEFLNVPEWSYIVEKD | 16 | 109 |
| 12 | 103 | 109 | NSLCYPG | 7 | 110 |
| 13 | 116 | 124 | ELKHLLSST | 9 | 111 |
| 14 | 129 | 136 | KIQIIPRS | 8 | 112 |
| 15 | 144 | 154 | SSGVSSACPYN | 11 | 113 |
| 16 | 160 | 167 | FRNVVWLI | 8 | 114 |
| 17 | 187 | 194 | DLLILWGI | 8 | 115 |
| 18 | 203 | 209 | QTKLYQN | 7 | 116 |
| 19 | 211 | 219 | TTYVSVGTS | 9 | 117 |
| 20 | 265 | 276 | APEYAYKIVKKG | 12 | 118 |
| 21 | 291 | 301 | NTKCQTPVGAI | 11 | 119 |
| 22 | 307 | 331 | FHNIHPLTIGECPKYVKSDRLVLAT | 25 | 120 |
| 23 | 349 | 355 | FGAIAGF | 7 | 121 |

SEQUENCE LISTING

<160> NUMBER OF SEQ ID NOS: 121

<210> SEQ ID NO 1
<211> LENGTH: 1749
<212> TYPE: DNA
<213> ORGANISM: Avian influenza

<400> SEQUENCE: 1

```
gaagacctca tggagaggat tgtgatagca cttgccatca tttctgtggt caaaggtgat      60
cagatctgca ttggctacca tgccaacaat tccaccaaac aagtggacac aatcatggag     120
aagaatgtga cagtcactca tgctcaagac attcttgaaa aggaacacaa tgggaaactc     180
tgcagcctca agggtgtgag acctctgata ctgaaagatt gcagtgtggc tgggtggttg     240
cttggcaacc caatgtgtga tgagtttctg aatgtccctg aatggtccta cattgttgag     300
aaagacaatc ccaccaatgg tctctgctac cctggtgact tcaatgacta tgaagagttg     360
aagtatctca tgtcaaacac aaaccacttt gagaagattc agatcattcc gaggaacagt     420
tggtcaaacc atgatgcttc ttctggagtc tcctcagctt gtccgtacaa tggtcgaagt     480
agcttctttc gaaatgtggt ttggctgatc aagaaatcca atgcctaccc aactatcaag     540
agaacataca acaataccaa tgttgaggac ttgctcatac tttggggaat ccaccatccg     600
```

```
aatgatgctg cagaacaaac tgaactctat cagaacagca acacctatgt gagtgttggc    660
acttcaacct tgaaccagcg tagcattcca gagattgcca ctcgtcccaa ggtcaatggt    720
caatctggga ggattgagtt cttttggaca atcttgagac cgaatgatgc catcagcttt    780
gaatccaatg gaacttcat tgctccagag tatgcctaca agatagtgaa gaaaggagat    840
tctgcaatca tgcgatctga acttgagtat ggcaactgtg atacaaagtg tcaaacacct    900
gttggtgcca tcaacagctc aatgcctttc cacaatgttc atccacttac cataggagag    960
tgtcccaagt atgtcaagtc agacaagttg gttcttgcca ccggtctgag gaatgtccca   1020
caaagagaaa ctagaggact gtttggcgcc attgctggat tcattgaagg aggctggcaa   1080
ggcatggttg atggatggta tggctatcat cactccaacg aacaaggctc tggctatgca   1140
gctgacaaag agtccacaca gaaagccata gatggaatca ccaacaaagt gaacagtatc   1200
atagacaaga tgaacactca gtttgaagct gttgggaaag agttcaacaa cttggaacga   1260
aggattgaga acctcaacaa aaagatggaa gatgggtttc ttgatgtctg gacatacaat   1320
gctgaactcc ttgttctcat ggagaatgag aggacacttg acttccacga ttcctatgtc   1380
aagaacctct atgacaaagt tcgtctccag ttgagagaca atgcaaagga gcttggcaat   1440
gggtgctttg agttctacca caagtgtgac aatgagtgca tggaaagtgt gaggaatggc   1500
acctatgact accctcagta ctcagaggaa ctcgtttga acagaagaa gatagatggt   1560 gtgaaactgg aatctatggg aacttaccag attctgagca tctactcaac tgttgcatct   1620
tccttggcat tggcaatcat ggttgctgga ctgagtttct ggatgtgttc aatgggagc    1680 cttcaatgca gaatctgcat ttgagtagtt agcttaatca cctagagctc cgtcaccaga   1740
tctctcgag                                                          1749
```

<210> SEQ ID NO 2
<211> LENGTH: 564
<212> TYPE: PRT
<213> ORGANISM: Avian influenza
<400> SEQUENCE: 2

```
Met Glu Arg Ile Val Ile Ala Leu Ala Ile Ile Ser Val Val Lys Gly
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Glu His Asn Gly Lys Leu Cys Ser Leu Lys Gly Val Arg
    50                  55                  60

Pro Leu Ile Leu Lys Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Thr Asn Gly Leu Cys Tyr Pro Gly Asp Phe Asn
            100                 105                 110

Asp Tyr Glu Glu Leu Lys Tyr Leu Met Ser Asn Thr Asn His Phe Glu
        115                 120                 125

Lys Ile Gln Ile Ile Pro Arg Asn Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Ser Asn Ala Tyr Pro Thr Ile
                165                 170                 175
```

Lys Arg Thr Tyr Asn Asn Thr Asn Val Glu Asp Leu Ile Leu Trp
            180                 185                 190

Gly Ile His His Pro Asn Asp Ala Ala Glu Gln Thr Glu Leu Tyr Gln
                195                 200                 205

Asn Ser Asn Thr Tyr Val Ser Val Gly Thr Ser Thr Leu Asn Gln Arg
            210                 215                 220

Ser Ile Pro Glu Ile Ala Thr Arg Pro Lys Val Asn Gly Gln Ser Gly
225                 230                 235                 240

Arg Ile Glu Phe Phe Trp Thr Ile Leu Arg Pro Asn Asp Ala Ile Ser
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Arg Ser Glu Leu Glu Tyr Gly
            275                 280                 285

Asn Cys Asp Thr Lys Cys Gln Thr Pro Val Gly Ala Ile Asn Ser Ser
290                 295                 300

Met Pro Phe His Asn Val His Pro Leu Thr Ile Gly Glu Cys Pro Lys
305                 310                 315                 320

Tyr Val Lys Ser Asp Lys Leu Val Leu Ala Thr Gly Leu Arg Asn Val
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
            355                 360                 365

Ser Asn Glu Gln Gly Ser Gly Tyr Ala Ala Asp Lys Glu Ser Thr Gln
370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
            435                 440                 445

Thr Leu Asp Phe His Asp Ser Tyr Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
            500                 505                 510

Glu Glu Ile Asp Gly Val Lys Leu Glu Ser Met Gly Thr Tyr Gln Ile
            515                 520                 525

Leu Ser Ile Tyr Ser Thr Val Ala Ser Ser Leu Ala Leu Ala Ile Met
            530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 3
<211> LENGTH: 1749
<212> TYPE: DNA
<213> ORGANISM: Avian influenza

```
<400> SEQUENCE: 3
gaagacctca tggagaggat tgtgatagca cttgccatca tttctgtggt caaaggtgat      60
cagatctgca ttggctacca tgccaacaat tccaccaaac aagtggacac aatcatggag     120
aagaatgtga cagtcactca tgctcaagac attcttgaaa ggaacacaa tgggaaactc      180 tgcagcctca gggtgtgag acctctgata ctgaaagatt gcagtgtggc tgggtggttg      240
cttggcaacc caatgtgtga tgagtttctg aatgtccctg aatggtccta cattgttgag      300
aaagacaatc ccaccaatgg tctctgctac cctggtgact caatgactac tgaagagttg      360
aagtatctca tgtcaaacac aaaccacttt gagaagattc agatcattcc gaggaacagt      420
tggtcaaacc atgatgcttc ttctggagtc cctcagctt gtccgtacaa tggtcgaagt       480
agcttctttc gaaatgtggt ttggctgatc aagaaatcca atgcctaccc aactatcaag      540
agaacataca acaataccaa tgttgaggac ttgctcatac tttggggaat ccaccatccg      600
aatgatgctg cagaacaaac tgaactctat cagaacagca cacctatgt gagtgttggc        660 acttcaacct gaaccagcg tagcattcca gagattgcca ctcgtcccaa ggtcaatggt        720
caaaacggga ggattgagtt cttttggaca atcttgagac cgaatgatgc catcagcttt      780
gaatccaatg ggaacttcat tgctccagag tatgcctaca agatagtgaa gaaaggagat      840
tctgcaatca tgcgatctga acttgagtat ggcaactgtg atacaaagtg tcaaacacct      900
gttggtgcca tcaacagctc aatgcctttc cacaatgttc atccacttac cataggagag      960
tgtcccaagt atgtcaagtc agacaagttg gttcttgcca ccggtctgag gaatgtccca     1020
caaagagaaa ctagaggact gtttggcgcc attgctggat tcattgaagg aggctggcaa     1080
ggcatggttg atggatggta tggctatcat cactccaacg aacaaggctc tggctatgca     1140
gctgacaaag agtccacaca gaaagccata gatggaatca ccaacaaagt gaacagtatc     1200
atagacaaga tgaacactca gtttgaagct gttgggaaag agttcaacaa cttggaacga     1260
aggattgaga acctcaacaa aaagatggaa gatgggtttc ttgatgtctg gacatacaat     1320
gctgaactcc ttgttctcat ggagaatgag aggacacttg acttccacga ttcctatgtc     1380
aagaacctct atgacaaagt tcgtctccag ttgagagaca atgcaaagga gcttggcaat     1440
gggtgctttg agttctacca cagtgtgac aatgagtgca tggaaagtgt gaggaatggc      1500
acctatgact ccctcagta ctcagaggaa tctcgtttga acagaagaa gatagatggt       1560 gtgaaactgg aatctatggg aacttaccag attctgagca tctactcaac tgttgcatct     1620
tccttggcat tggcaatcat ggttgctgga ctgagtttct ggatgtgttc caatgggagc     1680
cttcaatgca gaatctgcat ttgagtagtt agcttaatca cctagagctc cgtcaccaga     1740
tctctcgag                                                            1749

<210> SEQ ID NO 4
<211> LENGTH: 564
<212> TYPE: PRT
<213> ORGANISM: Avian influenza

<400> SEQUENCE: 4

Met Glu Arg Ile Val Ile Ala Leu Ala Ile Ile Ser Val Val Lys Gly
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45
```

-continued

```
Leu Glu Lys Glu His Asn Gly Lys Leu Cys Ser Leu Lys Gly Val Arg
    50                  55                  60
Pro Leu Ile Leu Lys Asp Cys Ser Val Ala Gly Trp Leu Leu Gly Asn
65                  70                  75                  80
Pro Met Cys Asp Glu Phe Leu Asn Val Pro Glu Trp Ser Tyr Ile Val
                85                  90                  95
Glu Lys Asp Asn Pro Thr Asn Gly Leu Cys Tyr Pro Gly Asp Phe Asn
            100                 105                 110
Asp Tyr Glu Glu Leu Lys Tyr Leu Met Ser Asn Thr Asn His Phe Glu
        115                 120                 125
Lys Ile Gln Ile Ile Pro Arg Asn Ser Trp Ser Asn His Asp Ala Ser
    130                 135                 140
Ser Gly Val Ser Ser Ala Cys Pro Tyr Asn Gly Arg Ser Ser Phe Phe
145                 150                 155                 160
Arg Asn Val Val Trp Leu Ile Lys Lys Ser Asn Ala Tyr Pro Thr Ile
                165                 170                 175
Lys Arg Thr Tyr Asn Asn Thr Asn Val Glu Asp Leu Leu Ile Leu Trp
            180                 185                 190
Gly Ile His His Pro Asn Asp Ala Ala Glu Gln Thr Glu Leu Tyr Gln
        195                 200                 205
Asn Ser Asn Thr Tyr Val Ser Val Gly Thr Ser Thr Leu Asn Gln Arg
    210                 215                 220
Ser Ile Pro Glu Ile Ala Thr Arg Pro Lys Val Asn Gly Gln Asn Gly
225                 230                 235                 240
Arg Ile Glu Phe Phe Trp Thr Ile Leu Arg Pro Asn Asp Ala Ile Ser
                245                 250                 255
Phe Glu Ser Asn Gly Asn Phe Ile Ala Pro Glu Tyr Ala Tyr Lys Ile
            260                 265                 270
Val Lys Lys Gly Asp Ser Ala Ile Met Arg Ser Glu Leu Glu Tyr Gly
        275                 280                 285
Asn Cys Asp Thr Lys Cys Gln Thr Pro Val Gly Ala Ile Asn Ser Ser
    290                 295                 300
Met Pro Phe His Asn Val His Pro Leu Thr Ile Gly Glu Cys Pro Lys
305                 310                 315                 320
Tyr Val Lys Ser Asp Lys Leu Val Leu Ala Thr Gly Leu Arg Asn Val
                325                 330                 335
Pro Gln Arg Glu Thr Arg Gly Leu Phe Gly Ala Ile Ala Gly Phe Ile
            340                 345                 350
Glu Gly Gly Trp Gln Gly Met Val Asp Gly Trp Tyr Gly Tyr His His
        355                 360                 365
Ser Asn Glu Gln Gly Ser Gly Tyr Ala Ala Asp Lys Glu Ser Thr Gln
    370                 375                 380
Lys Ala Ile Asp Gly Ile Thr Asn Lys Val Asn Ser Ile Ile Asp Lys
385                 390                 395                 400
Met Asn Thr Gln Phe Glu Ala Val Gly Lys Glu Phe Asn Asn Leu Glu
                405                 410                 415
Arg Arg Ile Glu Asn Leu Asn Lys Lys Met Glu Asp Gly Phe Leu Asp
            420                 425                 430
Val Trp Thr Tyr Asn Ala Glu Leu Leu Val Leu Met Glu Asn Glu Arg
        435                 440                 445
Thr Leu Asp Phe His Asp Ser Tyr Val Lys Asn Leu Tyr Asp Lys Val
    450                 455                 460
Arg Leu Gln Leu Arg Asp Asn Ala Lys Glu Leu Gly Asn Gly Cys Phe
465                 470                 475                 480
```

```
Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
            500                 505                 510

Glu Glu Ile Asp Gly Val Lys Leu Glu Ser Met Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 5
<211> LENGTH: 1761
<212> TYPE: DNA
<213> ORGANISM: Avian influenza

<400> SEQUENCE: 5
gaagacctca tggagaggat tgtgatagca cttgccatca tttctgtggt caaaggtgat      60
cagatctgca ttggctacca tgccaacaat tccaccaaac aagtggacac aatcatggag     120
aagaatgtga cagtcactca tgctcaagac attcttgaaa aggaacacaa tgggaaactc     180
tgcagcctca gggtgtgag acctctgata ctgaaagatt gcagtgtggc tgggtggttg     240
cttggcaacc caatgtgtga tgagtttctg aatgtccctg aatggtccta cattgttgag     300
aaagacaatc ccaccaatgg tctctgctac cctggtgact caatgactac tgaagagttg     360
aagtatctca gtcaaacac aaaccacttt gagaagattc agatcattcc gaggaacagt     420
tggtcaaacc atgatgcttc ttctggagtc tcctcagctt gtccgtacaa tggtcgaagt     480
agcttctttc gaaatgtggt ttggctgatc aagaaatcca atgcctaccc aactatcaag     540
agaacataca acaataccaa tgttgaggac ttgctcatac tttggggaat ccaccatccg     600
aatgatgctg cagaacaaac tgaactctat cagaacagca cacctatgt gagtgttggc     660
acttcaacct tgaaccagcg tagcattcca gagattgcca ctcgtcccaa ggtcaatggt     720
caatctggga ggattgagtt cttttggaca atcttgagac cgaatgatgc catcagcttt     780
gaatccaatg gaacttcat tgctccagag tatgcctaca gatagtgaa gaaaggagat     840
tctgcaatca tgcgatctga acttgagtat ggcaactgtg atacaaagtg tcaaacacct     900
gttggtgcca tcaacagctc aatgcctttc cacaatgttc atccacttac cataggagag     960
tgtcccaagt atgtcaagtc agacaagttg gttcttgcca ccggtctgag aatgtcccaa    1020
caaagagaaa ctagaaggca agagagga ctgtttggcg ccattgctgg attcattgaa    1080
ggaggctggc aaggcatggt tgatggatgg tatggctatc atcactccaa cgaacaaggc    1140
tctggctatg cagctgacaa agagtccaca cagaaagcca tagatggaat caccaacaaa    1200
gtgaacagta tcatagacaa gatgaacact cagtttgaag ctgttgggaa agagttcaac    1260
aacttggaac gaaggattga gaacctcaac aaaagatgg aagatgggtt tcttgatgtc    1320
tggacataca atgctgaact ccttgttctc atggagaatg agaggacact tgacttccac    1380
gattcctatg tcaagaacct ctatgacaaa gttcgtctcc agttgagaga caatgcaaag    1440
gagcttggca atgggtgctt tgagttctac cacaagtgtg acaatgagtg catggaaagt    1500
gtgaggaatg gcacctatga ctaccctcag tactcagagg aatctcgttt gaacagagaa    1560
gagatagatg gtgtgaaact ggaatctatg ggaacttacc agattctgag catctactca    1620
```

```
actgttgcat cttccttggc attggcaatc atggttgctg gactgagttt ctggatgtgt    1680
tccaatggga gccttcaatg cagaatctgc atttgagtag ttagcttaat cacctagagc    1740
tccgtcacca gatctctcga g                                              1761
```

<210> SEQ ID NO 6
<211> LENGTH: 568
<212> TYPE: PRT
<213> ORGANISM: Avian influenza

<400> SEQUENCE: 6

```
Met Glu Arg Ile Val Ile Ala Leu Ala Ile Ile Ser Val Val Lys Gly
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys His Asn Gly Lys Leu Cys Ser Leu Lys Gly Val Arg
    50                  55                  60

Pro Leu Ile Leu Lys Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Thr Asn Gly Leu Cys Tyr Pro Gly Asp Phe Asn
            100                 105                 110

Asp Tyr Glu Glu Leu Lys Tyr Leu Met Ser Asn Thr Asn His Phe Glu
        115                 120                 125

Lys Ile Gln Ile Ile Pro Arg Asn Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Ser Asn Ala Tyr Pro Thr Ile
                165                 170                 175

Lys Arg Thr Tyr Asn Asn Thr Asn Val Glu Asp Leu Leu Ile Leu Trp
            180                 185                 190

Gly Ile His His Pro Asn Asp Ala Ala Glu Gln Thr Glu Leu Tyr Gln
        195                 200                 205

Asn Ser Asn Thr Tyr Val Ser Val Gly Thr Ser Thr Leu Asn Gln Arg
    210                 215                 220

Ser Ile Pro Glu Ile Ala Thr Arg Pro Lys Val Asn Gly Gln Ser Gly
225                 230                 235                 240

Arg Ile Glu Phe Phe Trp Thr Ile Leu Arg Pro Asn Asp Ala Ile Ser
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Arg Ser Glu Leu Glu Tyr Gly
        275                 280                 285

Asn Cys Asp Thr Lys Cys Gln Thr Pro Val Gly Ala Ile Asn Ser Ser
    290                 295                 300

Met Pro Phe His Asn Val His Pro Leu Thr Ile Gly Glu Cys Pro Lys
305                 310                 315                 320

Tyr Val Lys Ser Asp Lys Leu Val Leu Ala Thr Gly Leu Arg Asn Val
                325                 330                 335

Pro Gln Arg Glu Thr Arg Arg Gln Lys Arg Gly Leu Phe Gly Ala Ile
            340                 345                 350
```

```
Ala Gly Phe Ile Glu Gly Gly Trp Gln Gly Met Val Asp Gly Trp Tyr
        355                 360                 365
Gly Tyr His His Ser Asn Glu Gln Gly Ser Gly Tyr Ala Ala Asp Lys
    370                 375                 380
Glu Ser Thr Gln Lys Ala Ile Asp Gly Ile Thr Asn Lys Val Asn Ser
385                 390                 395                 400
Ile Ile Asp Lys Met Asn Thr Gln Phe Glu Ala Val Gly Lys Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
        435                 440                 445
Glu Asn Glu Arg Thr Leu Asp Phe His Asp Ser Tyr Val Lys Asn Leu
    450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Val Arg Asn Gly Thr Tyr Asp Tyr Pro Gln Tyr Ser Glu Glu Ser
            500                 505                 510
Arg Leu Asn Arg Glu Glu Ile Asp Gly Val Lys Leu Glu Ser Met Gly
        515                 520                 525
Thr Tyr Gln Ile Leu Ser Ile Tyr Ser Thr Val Ala Ser Ser Leu Ala
    530                 535                 540
Leu Ala Ile Met Val Ala Gly Leu Ser Phe Trp Met Cys Ser Asn Gly
545                 550                 555                 560
Ser Leu Gln Cys Arg Ile Cys Ile
                565

<210> SEQ ID NO 7
<211> LENGTH: 1749
<212> TYPE: DNA
<213> ORGANISM: Avian influenza

<400> SEQUENCE: 7
gaagacctca tggagaggat tgtgatagca cttgccatca tttctgtggt caaaggtgat      60
cagatctgca ttggctacca tgccaacaat tccaccgaac aagtggacac aatcatggag     120
aagaatgtga cagtcactca tgctcaagac attcttgaaa agactcacaa tgggaaactc     180
tgcagcctca cggtgtgaa acctctgata ctgagagatt gcagtgtggc tgggtggctt     240
cttggcaacc caatgtgtga tgagtttctg aatgtccctg aatggcccta cattgttgag     300
aaagccaatc ccgtcaattc gctctgctac cctggtgact tcaatgacta tgaagagttg     360
aagcacctcc tgtcaagcac aaaccacttt gagaagattc agatcattcc gaggagcagt     420
tggtcaaacc atgatgcttc ttctggagtc tcctcagctt gtccgtacaa tggtcgaagt     480
agcttctttc gaaatgtggt ttggctgatc aagaaaaact ctacctaccc aactatcaag     540
agatcataca acaataccaa tcaagaggac ttgttgatac tttggggaat ccaccatccg     600
aatgatgctg cagaacaaac taaactctat cagaacccca ccacctatgt gagtgttggc     660
acttcaacct gaaccagcg tagcattcca gagattgcca ctcgtcccaa ggtcaatggt     720
caatctggga ggatggagtt cttttggaca atcctcaaac cgaatgatgc catcaacttt     780
gaatccaatg gaacttcat tgctccagag tatgcctaca gatagtgaa gaaaggagat     840
tctgcaatca tgaagtctga acttgagtat ggcaactgta cacaaagtg tcaaacacct     900
```

```
gttggtgcca tcaacagctc aatgcctttc cacaatattc atccacttac cataggagag    960
tgtcccaagt atgtcaagtc agaccgattg gttcttgcca ccggtctgag gaatgtccca   1020
caaagagaaa ctagaggact gtttggcgcc attgctggat cattgaagg aggctggcaa   1080
ggcatggttg atggatggta tggctatcat cactccaacg aacaaggctc tggctatgca   1140
gctgacaaag agtccacaca gaaagccata gatggaatca ccaacaaagt gaacagtatc   1200
atagacaaga tgaacactca gtttgaagct gttgggaaag agttcaacaa cttggaacga   1260
aggattgaga acctcaacaa aaagatggaa gatgggtttc ttgatgtctg gacatacaat   1320
gctgaactcc ttgttctcat ggagaatgag aggacacttg acttccacga ttcctatgtc   1380
aagaacctct atgacaaagt cgtctccag ttgagagaca atgcaaagga gcttggcaat   1440
gggtgctttg agttctacca caagtgtgac aatgagtgca tggaaagtgt gaggaatggc   1500
acctatgact accctcagta ctcagaggaa tctcgtttga acagagaaga gatagatggt   1560
gtgaaactgg aatctatggg aacttaccag attctgagca tctactcaac tgttgcatct   1620
tccttggcat tggcaatcat ggttgctgga ctgagtttct ggatgtgttc caatgggagc   1680
cttcaatgca gaatctgcat ttgagtagtt agcttaatca cctagagctc cgtcaccaga   1740
tctctcgag                                                           1749

<210> SEQ ID NO 8
<211> LENGTH: 564
<212> TYPE: PRT
<213> ORGANISM: Avian influenza

<400> SEQUENCE: 8

Met Glu Arg Ile Val Ile Ala Leu Ala Ile Ile Ser Val Val Lys Gly
  1               5                  10                  15

Asp Gln Ile Cys Ile Gly Tyr His Ala Asn Asn Ser Thr Glu Gln Val
                 20                  25                  30

Asp Thr Ile Met Glu Lys Asn Val Thr Val Thr His Ala Gln Asp Ile
             35                  40                  45

Leu Glu Lys Thr His Asn Gly Lys Leu Cys Ser Leu Asn Gly Val Lys
         50                  55                  60

Pro Leu Ile Leu Arg Asp Cys Ser Val Ala Gly Trp Leu Leu Gly Asn
 65                  70                  75                  80

Pro Met Cys Asp Glu Phe Leu Asn Val Pro Glu Trp Ser Tyr Ile Val
                 85                  90                  95

Glu Lys Ala Asn Pro Val Asn Ser Leu Cys Tyr Pro Gly Asp Phe Asn
            100                 105                 110

Asp Tyr Glu Glu Leu Lys His Leu Leu Ser Ser Thr Asn His Phe Glu
        115                 120                 125

Lys Ile Gln Ile Ile Pro Arg Ser Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
    210                 215                 220
```

```
Ser Ile Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Val Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Tyr Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
            500                 505                 510

Glu Glu Ile Asp Gly Val Lys Leu Glu Ser Met Gly Thr Tyr Gln Ile
        515                 520                 525

Leu Ser Ile Tyr Ser Thr Val Ala Ser Ser Leu Ala Leu Ala Ile Met
530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 9
<211> LENGTH: 1749
<212> TYPE: DNA
<213> ORGANISM: Avian influenza

<400> SEQUENCE: 9
gaagacctca tggagaggat tgtgatagca cttgccatca tttctgtggt caaaggtgat      60
cagatctgca ttggctacca tgccaacaat tccaccgaac aagtggacac aatcatggag     120
aagaatgtga cagtcactca tgctcaagac attcttgaaa agactcacaa tgggaaactc     180
tgcagcctca acgtgtgaa acctctgata ctgagagatt gcagtgtggc tgggtggctt     240
```

```
cttggcaacc caatgtgtga tgagtttctg aatgtccctg aatggtccta cattgttgag      300
aaagccaatc ccgtcaattc gctctgctac cctggtgact tcaatgacta tgaagagttg      360
aagcacctcc tgtcaagcac aaaccacttt gagaagattc agatcattcc gaggagcagt      420
tggtcaaacc atgatgcttc ttctggagtc tcctcagctt gtccgtacaa tggtcgaagt      480
agcttctttc gaaatgtggt ttggctgatc aagaaaaaca atgcctaccc aactatcaag      540
agatcataca acaataccaa tcaagaggac ttgttgatac tttggggaat ccaccatccg      600
aatgatgctg cagaacaaac taaactctat cagaacccca ccacctatgt gagtgttggc      660
acttcaacct tgaaccagcg tagcattcca gagattgcca ctcgtcccaa ggtcaatggt      720
caaaacggga ggatggagtt cttttggaca atcctcaaac cgaatgatgc catcaacttt      780
gaatccaatg ggaacttcat tgctccagag tatgcctaca agatagtgaa gaaaggagat      840
tctgcaatca tgaagtctga acttgagtat ggcaactgta acacaaagtg tcaaacacct      900
gttggtgcca tcaacagctc aatgcctttc acaatattc atccacttac cataggagag      960
tgtcccaagt atgtcaagtc agaccgattg gttcttgcca ccggtctgag gaatgtccca     1020
caaagagaaa ctagaggact gtttggcgcc attgctggat tcattgaagg aggctggcaa     1080
ggcatggttg atggatggta tggctatcat cactccaacg aacaaggctc tggctatgca     1140
gctgacaaag agtccacaca gaaagccata gatggaatca ccaacaaagt gaacagtatc     1200
atagacaaga tgaacactca gtttgaagct gttgggaaag agttcaacaa cttggaacga     1260
aggattgaga acctcaacaa aaagatggaa gatgggtttc ttgatgtctg gacatacaat     1320
gctgaactcc ttgttctcat ggagaatgag aggacacttg acttccacga ttcctatgtc     1380
aagaacctct atgacaaagt tcgtctccag ttgagagaca atgcaaagga gcttggcaat     1440
gggtgctttg agttctacca caagtgtgac aatgagtgca tggaaagtgt gaggaatggc     1500
acctatgact acccctcagta ctcagaggaa tctcgtttga acagagaaga gatagatggt     1560
gtgaaactgg aatctatggg aacttaccag attctgagca tctactcaac tgttgcatct     1620
tccttggcat tggcaatcat ggttgctgga ctgagtttct ggatgtgttc caatgggagc     1680
cttcaatgca gaatctgcat ttgagtagtt agcttaatca cctagagctc cgtcaccaga     1740
tctctcgag                                                             1749
```

<210> SEQ ID NO 10
<211> LENGTH: 564
<212> TYPE: PRT
<213> ORGANISM: Avian influenza

<400> SEQUENCE: 10

```
Met Glu Arg Ile Val Ile Ala Leu Ala Ile Ile Ser Val Val Lys Gly
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ala Asn Pro Val Asn Ser Leu Cys Tyr Pro Gly Asp Phe Asn
```

-continued

```
                100                 105                 110
Asp Tyr Glu Glu Leu Lys His Leu Leu Ser Ser Thr Asn His Phe Glu
            115                 120                 125

Lys Ile Gln Ile Ile Pro Arg Ser Ser Trp Ser Asn His Asp Ala Ser
            130                 135                 140

Ser Gly Val Ser Ser Ala Cys Pro Tyr Asn Gly Arg Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
            195                 200                 205

Asn Pro Thr Thr Tyr Val Ser Val Gly Thr Ser Thr Leu Asn Gln Arg
            210                 215                 220

Ser Ile Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Val Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
            355                 360                 365

Ser Asn Glu Gln Gly Ser Gly Tyr Ala Ala Asp Lys Glu Ser Thr Gln
370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
            435                 440                 445

Thr Leu Asp Phe His Asp Ser Tyr Val Lys Asn Leu Tyr Asp Lys Val
            450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
                500                 505                 510

Glu Glu Ile Asp Gly Val Lys Leu Glu Ser Met Gly Thr Tyr Gln Ile
            515                 520                 525
```

Leu Ser Ile Tyr Ser Thr Val Ala Ser Ser Leu Ala Leu Ala Ile Met
            530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 11
<211> LENGTH: 1749
<212> TYPE: DNA
<213> ORGANISM: Avian influenza

<400> SEQUENCE: 11

```
gaagacctca tggagaggat tgtgatagca cttgccatca tttctgtggt caaaggtgat     60
cagatctgca ttggctacca tgccaacaat tccaccgaac aagtggacac aatcatggag    120
aagaatgtga cagtcactca tgctcaagac attcttgaaa agactcacaa tgggaaactc    180
tgcagcctca cggtgtgaa acctctgata ctgagagatt gcagtgtggc tgggtggctt    240
cttggcaacc caatgtgtga tgagtttctg aatgtccctg aatggtccta cattgttgag    300
aaagccaatc ccgtcaattc gctctgctac cctggtgact tcaatgacta tgaagagttg    360
aagcacctcc tgtcaagcac aaaccacttt gagaagattc agatcattcc gaggagcagt    420
tggtcaaacc atgatgcttc ttctggagtc cctcagcttg tccgtacaa tggtcgaagt    480
agcttctttc gaaatgtggt ttggctgatc aagaaaaact ctacctaccc aactatcaag    540
agatcataca caataccaa tcaagaggac ttgttgatac tttggggaat ccaccatccg    600
aatgatgctg cagaacaaac taaactctat cagaaccca ccacctatgt gagtgttggc    660
acttcaacct tgaaccagcg tagcattcca gagattgcca ctcgtcccaa ggtcaatggt    720
caaaacggga ggatggagtt cttttggaca atcctcaaac cgaatgatgc catcaacttt    780
gaatccaatg gaacttcat tgctccagag tatgcctaca aatagtgaa gaaaggagat    840
tctgcaatca tgaagtctga acttgagtat ggcaactgta acacaaagtg tcaaacacct    900
gttggtgcca tcaacagctc aatgcctttc acaatattc atccacttac cataggagag    960
tgtcccaagt atgtcaagtc agaccgattg gttcttgcca ccggtctgag gaatgtccca   1020
caaagagaaa ctagaggact gtttggcgcc attgctggat tcattgaagg aggctggcaa   1080
ggcatggttg atggatggta tggctatcat cactccaacg aacaaggctc tggctatgca   1140
gctgacaaag agtccacaca gaaagccata gatggaatca ccaacaaagt gaacagtatc   1200
atagacaaga tgaacactca gtttgaagct gttgggaaag agttcaacaa cttggaacga   1260
aggattgaga acctcaacaa aaagatggaa gatgggtttc ttgatgtctg gacatacaat   1320
gctgaactcc ttgttctcat ggagaatgag aggacacttg acttccacga ttcctatgtc   1380
aagaacctct atgacaaagt tcgtctccag ttgagagaca tgcaaagga gcttggcaat   1440
gggtgctttg agttctacca caagtgtgac aatgagtgca tggaaagtgt gaggaatggc   1500
acctatgact accctcagta ctcagaggaa tctcgtttga cagagaaga gatagatggt   1560
gtgaaactgg aatctatggg aacttaccag attctgagca tctactcaac tgttgcatct   1620
tccttggcat tggcaatcat ggttgctgga ctgagtttct ggatgtgttc aatgggagc   1680
cttcaatgca gaatctgcat ttgagtagtt agcttaatca cctagagctc cgtcaccaga   1740
tctctcgag                                                          1749
```

<210> SEQ ID NO 12
<211> LENGTH: 553
<212> TYPE: PRT

<213> ORGANISM: Avian influenza

<400> SEQUENCE: 12

```
Met Glu Arg Ile Val Ile Ala Leu Ala Ile Ile Ser Val Val Lys Gly
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ala Asn Pro Val Asn Ser Leu Cys Tyr Pro Gly Asp Phe Asn
            100                 105                 110

Asp Tyr Glu Glu Leu Lys His Leu Leu Ser Ser Thr Asn His Phe Glu
        115                 120                 125

Lys Ile Gln Ile Ile Pro Arg Ser Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
    210                 215                 220

Ser Ile Pro Glu Ile Ala Thr Arg Pro Lys Val Asn Gly Gln Asn Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Val Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
```

```
                           405                 410                 415
Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Tyr Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
            500                 505                 510

Glu Glu Ile Asp Gly Val Lys Leu Glu Ser Met Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Phe Trp Met Cys
545                 550

<210> SEQ ID NO 13
<211> LENGTH: 1692
<212> TYPE: DNA
<213> ORGANISM: Artificial sequence
<220> FEATURE:
<223> OTHER INFORMATION: Avian influenza hemagglutinin sequence
<220> FEATURE:
<221> NAME/KEY: CDS
<222> LOCATION: (1)..(1692)

<400> SEQUENCE: 13 atg gag agg att gtg ata gca ctt gcc atc att tct gtg gtc aaa ggt     48
Met Glu Arg Ile Val Ile Ala Leu Ala Ile Ile Ser Val Val Lys Gly
1               5                   10                  15 gat cag atc tgc att ggc tac cat gcc aac aat tcc acc gaa caa gtg     96
Asp Gln Ile Cys Ile Gly Tyr His Ala Asn Asn Ser Thr Glu Gln Val
            20                  25                  30 gac aca atc atg gag aag aat gtg aca gtc act cat gct caa gac att    144
Asp Thr Ile Met Glu Lys Asn Val Thr Val Thr His Ala Gln Asp Ile
        35                  40                  45 ctt gaa aag act cac aat ggg aaa ctc tgc agc ctc aac ggt gtg aaa    192
Leu Glu Lys Thr His Asn Gly Lys Leu Cys Ser Leu Asn Gly Val Lys
    50                  55                  60 cct ctg ata ctg aga gat tgc agt gtg gct ggg tgg ctt ctt ggc aac    240
Pro Leu Ile Leu Arg Asp Cys Ser Val Ala Gly Trp Leu Leu Gly Asn
65                  70                  75                  80 cca atg tgt gat gag ttt ctg aat gtc cct gaa tgg tcc tac att gtt    288
Pro Met Cys Asp Glu Phe Leu Asn Val Pro Glu Trp Ser Tyr Ile Val
                85                  90                  95 gag aaa gac aat ccc atc aat tcg ctc tgc tac cct ggt gac ttc aat    336
Glu Lys Asp Asn Pro Ile Asn Ser Leu Cys Tyr Pro Gly Asp Phe Asn
            100                 105                 110 gac tat gaa gag ttg aag cac ctc ctg tca agc aca aac cac ttt gag    384
Asp Tyr Glu Glu Leu Lys His Leu Leu Ser Ser Thr Asn His Phe Glu
        115                 120                 125 aag att cag atc att ccg agg agc agt tgg tca aac cat gat gct tct    432
Lys Ile Gln Ile Ile Pro Arg Ser Ser Trp Ser Asn His Asp Ala Ser
    130                 135                 140 tct gga gtc tcc tca gct tgt ccg tac aat ggt cga agt agc ttc ttt    480
Ser Gly Val Ser Ser Ala Cys Pro Tyr Asn Gly Arg Ser Ser Phe Phe
```

```
                 145                 150                 155                 160
cga aat gtg gtt tgg ctg atc aag aaa aac aat gcc tac cca act atc         528
Arg Asn Val Val Trp Leu Ile Lys Lys Asn Asn Ala Tyr Pro Thr Ile
            165                 170                 175 aag aga tca tac aac aat acc aat caa gag gac ttg ttg ata ctt tgg         576
Lys Arg Ser Tyr Asn Asn Thr Asn Gln Glu Asp Leu Leu Ile Leu Trp
            180                 185                 190 gga atc cac cat ccg aat gat gct gca gaa caa act aaa ctc tat cag         624
Gly Ile His His Pro Asn Asp Ala Ala Glu Gln Thr Lys Leu Tyr Gln
            195                 200                 205 aac ccc acc acc tat gtg agt gtt ggc act tca acc ttg aac cag cgt         672
Asn Pro Thr Thr Tyr Val Ser Val Gly Thr Ser Thr Leu Asn Gln Arg
    210                 215                 220 agc att cca gag att gcc act cgt ccc aag gtc aat ggt caa tct ggg         720
Ser Ile Pro Glu Ile Ala Thr Arg Pro Lys Val Asn Gly Gln Ser Gly
225                 230                 235                 240 agg atg gag ttc ttt tgg aca atc ctc aaa ccg aat gat gcc atc aac         768
Arg Met Glu Phe Phe Trp Thr Ile Leu Lys Pro Asn Asp Ala Ile Asn
                245                 250                 255 ttt gaa tcc aat ggg aac ttc att gct cca gag tat gcc tac aag ata         816
Phe Glu Ser Asn Gly Asn Phe Ile Ala Pro Glu Tyr Ala Tyr Lys Ile
            260                 265                 270 gtg aag aaa gga gat tct gca atc atg aag tct gaa ctt gag tat ggc         864
Val Lys Lys Gly Asp Ser Ala Ile Met Lys Ser Glu Leu Glu Tyr Gly
        275                 280                 285 aac tgt aac aca aag tgt caa aca cct gtt ggt gcc atc aac agc tca         912
Asn Cys Asn Thr Lys Cys Gln Thr Pro Val Gly Ala Ile Asn Ser Ser
    290                 295                 300 atg cct ttc cac aat att cat cca ctt acc ata gga gag tgt ccc aag         960
Met Pro Phe His Asn Ile His Pro Leu Thr Ile Gly Glu Cys Pro Lys
305                 310                 315                 320 tat gtc aag tca gac cga ttg gtt ctt gcc acc ggt ctg agg aat gtc        1008
Tyr Val Lys Ser Asp Arg Leu Val Leu Ala Thr Gly Leu Arg Asn Val
                325                 330                 335 cca caa aga gaa act aga gga ctg ttt ggc gcc att gct gga ttc att        1056
Pro Gln Arg Glu Thr Arg Gly Leu Phe Gly Ala Ile Ala Gly Phe Ile
            340                 345                 350 gaa gga ggc tgg caa ggc atg gtt gat gga tgg tat ggc tat cat cac        1104
Glu Gly Gly Trp Gln Gly Met Val Asp Gly Trp Tyr Gly Tyr His His
        355                 360                 365 tcc aac gaa caa ggc tct ggc tat gca gct gac aaa gag tcc aca cag        1152
Ser Asn Glu Gln Gly Ser Gly Tyr Ala Ala Asp Lys Glu Ser Thr Gln
    370                 375                 380 aaa gcc ata gat gga atc acc aac aaa gtg aac agt atc ata gac aag        1200
Lys Ala Ile Asp Gly Ile Thr Asn Lys Val Asn Ser Ile Ile Asp Lys
385                 390                 395                 400 atg aac act cag ttt gaa gct gtt ggg aaa gag ttc aac aac ttg gaa        1248
Met Asn Thr Gln Phe Glu Ala Val Gly Lys Glu Phe Asn Asn Leu Glu
                405                 410                 415 cga agg att gag aac ctc aac aaa aag atg gaa gat ggg ttt cta gat        1296
Arg Arg Ile Glu Asn Leu Asn Lys Lys Met Glu Asp Gly Phe Leu Asp
            420                 425                 430 gtc tgg aca tac aat gct gaa ctc ctt gtt ctc atg gag aat gag agg        1344
Val Trp Thr Tyr Asn Ala Glu Leu Leu Val Leu Met Glu Asn Glu Arg
        435                 440                 445 aca ctt gac ttc cac gat tcc tat gtc aag aac ctc tat gac aaa gtt        1392
Thr Leu Asp Phe His Asp Ser Tyr Val Lys Asn Leu Tyr Asp Lys Val
    450                 455                 460 cgt ctc cag ttg aga gac aat gca aag gag ctt ggc aat ggg tgc ttt        1440
Arg Leu Gln Leu Arg Asp Asn Ala Lys Glu Leu Gly Asn Gly Cys Phe
```

```
                465                 470                 475                 480
gag ttc tac cac aag tgt gac aat gag tgc atg gaa agt gtg agg aat    1488
Glu Phe Tyr His Lys Cys Asp Asn Glu Cys Met Glu Ser Val Arg Asn
                485                 490                 495 ggc acc tat gac tac cct cag tac tca gag gaa tct cgt ttg aac aga    1536
Gly Thr Tyr Asp Tyr Pro Gln Tyr Ser Glu Glu Ser Arg Leu Asn Arg
            500                 505                 510 gaa gag ata gat ggt gtg aaa ctg gaa tct atg gga act tac cag att    1584
Glu Glu Ile Asp Gly Val Lys Leu Glu Ser Met Gly Thr Tyr Gln Ile
        515                 520                 525 ctg agc atc tac tca act gtt gca tct tcc ttg gca ttg gca atc atg    1632
Leu Ser Ile Tyr Ser Thr Val Ala Ser Ser Leu Ala Leu Ala Ile Met
    530                 535                 540 gtt gct gga ctg agt ttc tgg atg tgt tcc aat ggg agc ctt caa tgc    1680
Val Ala Gly Leu Ser Phe Trp Met Cys Ser Asn Gly Ser Leu Gln Cys
545                 550                 555                 560 aga atc tgc att                                                    1692
Arg Ile Cys Ile <210> SEQ ID NO 14
<211> LENGTH: 564
<212> TYPE: PRT
<213> ORGANISM: Artificial sequence
<220> FEATURE:
<223> OTHER INFORMATION: Synthetic Construct

<400> SEQUENCE: 14

Met Glu Arg Ile Val Ile Ala Leu Ala Ile Ile Ser Val Val Lys Gly
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Ile Asn Ser Leu Cys Tyr Pro Gly Asp Phe Asn
            100                 105                 110

Asp Tyr Glu Glu Leu Lys His Leu Leu Ser Ser Thr Asn His Phe Glu
        115                 120                 125

Lys Ile Gln Ile Ile Pro Arg Ser Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Ala Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
    210                 215                 220

Ser Ile Pro Glu Ile Ala Thr Arg Pro Lys Val Asn Gly Gln Ser Gly
225                 230                 235                 240
```

```
Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Val Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Tyr Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
            500                 505                 510

Glu Glu Ile Asp Gly Val Lys Leu Glu Ser Met Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 15
<211> LENGTH: 32
<212> TYPE: DNA
<213> ORGANISM: Artificial sequence
<220> FEATURE:
<223> OTHER INFORMATION: Primers AI 11 for amplification of HA genes

<400> SEQUENCE: 15
gctagcggcc gcaatgcaga ttctgcattg aa                             32

<210> SEQ ID NO 16
<211> LENGTH: 29
<212> TYPE: DNA
<213> ORGANISM: Artificial sequence
<220> FEATURE:
```

```
<223> OTHER INFORMATION: Primers AI 12 for amplification of HA genes

<400> SEQUENCE: 16
gcataagctt ccatggagag gattgtgat                                        29

<210> SEQ ID NO 17
<211> LENGTH: 5
<212> TYPE: PRT
<213> ORGANISM: Artificial Sequence
<220> FEATURE:
<223> OTHER INFORMATION: peptide linker sequence

<400> SEQUENCE: 17

Ser Gly Gly Gly Gly
1               5

<210> SEQ ID NO 18
<211> LENGTH: 7
<212> TYPE: PRT
<213> ORGANISM: Artificial Sequence
<220> FEATURE:
<223> OTHER INFORMATION: peptide linker sequence

<400> SEQUENCE: 18

Ser Gly Gly Gly Gly Ser Pro
1               5

<210> SEQ ID NO 19
<211> LENGTH: 5
<212> TYPE: PRT
<213> ORGANISM: Artificial Sequence
<220> FEATURE:
<223> OTHER INFORMATION: peptide linker sequence

<400> SEQUENCE: 19

Ser Ser Ser Ser Gly
1               5

<210> SEQ ID NO 20
<211> LENGTH: 7
<212> TYPE: PRT
<213> ORGANISM: Artificial Sequence
<220> FEATURE:
<223> OTHER INFORMATION: peptide linker sequence

<400> SEQUENCE: 20

Ser Ser Ser Ser Gly Ser Pro
1               5

<210> SEQ ID NO 21
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 21

Lys Gly Asp Gln Ile Cys Ile
1               5

<210> SEQ ID NO 22
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 22
```

```
Ile Gly Glu Cys Pro Lys Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: Avian influenza hemagglutinin sequence

<400> SEQUENCE: 23

Ile Pro Glu Ile Ala Thr Arg Pro
1               5

<210> SEQ ID NO 24
<211> LENGTH: 6
<212> TYPE: PRT
<213> ORGANISM: Artificial Sequence
<220> FEATURE:
<223> OTHER INFORMATION: Avian influenza hemagglutinin sequence

<400> SEQUENCE: 24

Ala Ala Glu Gln Thr Lys
1               5

<210> SEQ ID NO 25
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 25

Phe Ile Ala Pro Glu Tyr Ala
1               5

<210> SEQ ID NO 26
<211> LENGTH: 6
<212> TYPE: PRT
<213> ORGANISM: Artificial Sequence
<220> FEATURE:
<223> OTHER INFORMATION: Avian influenza hemagglutinin sequence

<400> SEQUENCE: 26

Pro Met Cys Asp Glu Phe
1               5

<210> SEQ ID NO 27
<211> LENGTH: 6
<212> TYPE: PRT
<213> ORGANISM: Artificial Sequence
<220> FEATURE:
<223> OTHER INFORMATION: Avian influenza hemagglutinin sequence

<400> SEQUENCE: 27

Pro Lys Tyr Val Lys Ser
1               5

<210> SEQ ID NO 28
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 28

Pro Leu Ile Leu Arg Asp Cys
```

<210> SEQ ID NO 29
<211> LENGTH: 6
<212> TYPE: PRT
<213> ORGANISM: Artificial Sequence
<220> FEATURE:
<223> OTHER INFORMATION: Avian influenza hemagglutinin sequence

<400> SEQUENCE: 29

Gly Lys Leu Cys Ser Leu
1               5

<210> SEQ ID NO 30
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 30

Lys Ile Val Lys Lys Gly Asp
1               5

<210> SEQ ID NO 31
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 31

Thr Ile Gly Glu Cys Pro Lys
1               5

<210> SEQ ID NO 32
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 32

Thr Ile Met Glu Lys Asn Val
1               5

<210> SEQ ID NO 33
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 33

Val Leu Ala Thr Gly Leu Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 34

Tyr Ile Val Glu Lys Asp Asn
1               5

```
<210> SEQ ID NO 35
<211> LENGTH: 6
<212> TYPE: PRT
<213> ORGANISM: Artificial Sequence
<220> FEATURE:
<223> OTHER INFORMATION: Avian influenza hemagglutinin sequence

<400> SEQUENCE: 35

Tyr Val Ser Val Gly Thr
1               5

<210> SEQ ID NO 36
<211> LENGTH: 6
<212> TYPE: PRT
<213> ORGANISM: Artificial Sequence
<220> FEATURE:
<223> OTHER INFORMATION: Avian influenza hemagglutinin sequence

<400> SEQUENCE: 36

Asn Val Pro Glu Trp Ser
1               5

<210> SEQ ID NO 37
<211> LENGTH: 6
<212> TYPE: PRT
<213> ORGANISM: Artificial Sequence
<220> FEATURE:
<223> OTHER INFORMATION: Avian influenza hemagglutinin sequence

<400> SEQUENCE: 37

Arg Met Glu Phe Phe Trp
1               5

<210> SEQ ID NO 38
<211> LENGTH: 8
<212> TYPE: PRT
<213> ORGANISM: Artificial Sequence
<220> FEATURE:
<223> OTHER INFORMATION: Avian influenza hemagglutinin sequence

<400> SEQUENCE: 38

Val Ile Ala Leu Ala Ile Ile Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 39

Ile Val Ile Ala Leu Ala Ile Ile Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 40

Phe Glu Lys Ile Gln Ile Ile Pro Arg
1               5

<210> SEQ ID NO 41
```

```
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 41

Phe Phe Arg Asn Val Val Trp Leu Ile
1               5

<210> SEQ ID NO 42
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 42

Phe His Asn Ile His Pro Leu Thr Ile
1               5

<210> SEQ ID NO 43
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 43

Phe Arg Asn Val Val Trp Leu Ile Lys
1               5

<210> SEQ ID NO 44
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 44

Phe Trp Thr Ile Leu Lys Pro Asn Asp
1               5

<210> SEQ ID NO 45
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 45

Ile Ala Pro Glu Tyr Ala Tyr Lys Ile
1               5

<210> SEQ ID NO 46
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 46

Ile Ala Thr Arg Pro Lys Val Asn Gly
1               5

<210> SEQ ID NO 47
<211> LENGTH: 9
<212> TYPE: PRT
```

```
<213> ORGANISM: Artificial Sequence
<220> FEATURE:
<223> OTHER INFORMATION: Avian influenza hemagglutinin sequence

<400> SEQUENCE: 47

Ile Gly Tyr His Ala Asn Asn Ser Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 48

Ile His Pro Leu Thr Ile Gly Glu Cys
1               5

<210> SEQ ID NO 49
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 49

Ile Ile Pro Arg Ser Ser Trp Ser Asn
1               5

<210> SEQ ID NO 50
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 50

Ile Ile Ser Val Val Lys Gly Asp Gln
1               5

<210> SEQ ID NO 51
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 51

Ile Lys Lys Asn Asn Ala Tyr Pro Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 52

Ile Lys Arg Ser Tyr Asn Asn Thr Asn
1               5

<210> SEQ ID NO 53
<211> LENGTH: 9
<212> TYPE: PRT
<213> ORGANISM: Artificial Sequence
<220> FEATURE:
```

<223> OTHER INFORMATION: Avian influenza hemagglutinin sequence

<400> SEQUENCE: 53

Ile Leu Arg Asp Cys Ser Val Ala Gly
1               5

<210> SEQ ID NO 54
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 54

Ile Asn Phe Glu Ser Asn Gly Asn Phe
1               5

<210> SEQ ID NO 55
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 55

Ile Gln Ile Ile Pro Arg Ser Ser Trp
1               5

<210> SEQ ID NO 56
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 56

Leu Ala Ile Ile Ser Val Val Lys Gly
1               5

<210> SEQ ID NO 57
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 57

Leu Ile Leu Arg Asp Cys Ser Val Ala
1               5

<210> SEQ ID NO 58
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 58

Leu Ile Leu Trp Gly Ile His His Pro
1               5

<210> SEQ ID NO 59
<211> LENGTH: 9
<212> TYPE: PRT
<213> ORGANISM: Artificial Sequence
<220> FEATURE:
<223> OTHER INFORMATION: Avian influenza hemagglutinin sequence

```
<400> SEQUENCE: 59

Leu Lys His Leu Leu Ser Ser Thr Asn
1               5

<210> SEQ ID NO 60
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 60

Leu Lys Pro Asn Asp Ala Ile Asn Phe
1               5

<210> SEQ ID NO 61
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 61

Leu Leu Ile Leu Trp Gly Ile His His
1               5

<210> SEQ ID NO 62
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 62

Leu Leu Ser Ser Thr Asn His Phe Glu
1               5

<210> SEQ ID NO 63
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 63

Leu Asn Gly Val Lys Pro Leu Ile Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 64

Leu Asn Gln Arg Ser Ile Pro Glu Ile
1               5

<210> SEQ ID NO 65
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 65
```

```
Leu Arg Asn Val Pro Gln Arg Glu Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 66

Leu Thr Ile Gly Glu Cys Pro Lys Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 67

Leu Val Leu Ala Thr Gly Leu Arg Asn
1               5

<210> SEQ ID NO 68
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 68

Leu Tyr Gln Asn Pro Thr Thr Tyr Val
1               5

<210> SEQ ID NO 69
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 69

Met Glu Phe Phe Trp Thr Ile Leu Lys
1               5

<210> SEQ ID NO 70
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 70

Met Glu Lys Asn Val Thr Val Thr His
1               5

<210> SEQ ID NO 71
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 71

Met Glu Arg Ile Val Ile Ala Leu Ala
1               5
```

```
<210> SEQ ID NO 72
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 72

Met Pro Phe His Asn Ile His Pro Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 73

Val Glu Lys Asp Asn Pro Ile Asn Ser
1               5

<210> SEQ ID NO 74
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 74

Val Ile Ala Leu Ala Ile Ile Ser Val
1               5

<210> SEQ ID NO 75
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 75

Val Lys Gly Asp Gln Ile Cys Ile Gly
1               5

<210> SEQ ID NO 76
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 76

Val Lys Pro Leu Ile Leu Arg Asp Cys
1               5

<210> SEQ ID NO 77
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 77

Val Lys Ser Asp Arg Leu Val Leu Ala
1               5
```

```
<210> SEQ ID NO 78
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 78

Val Asn Gly Gln Ser Gly Arg Met Glu
1               5

<210> SEQ ID NO 79
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 79

Val Pro Gln Arg Glu Thr Arg Arg Gln
1               5

<210> SEQ ID NO 80
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 80

Val Thr Val Thr His Ala Gln Asp Ile
1               5

<210> SEQ ID NO 81
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 81

Val Val Lys Gly Asp Gln Ile Cys Ile
1               5

<210> SEQ ID NO 82
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 82

Val Val Trp Leu Ile Lys Lys Asn Asn
1               5

<210> SEQ ID NO 83
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 83

Val Trp Leu Ile Lys Lys Asn Asn Ala
1               5

<210> SEQ ID NO 84
<211> LENGTH: 9
```

```
<212> TYPE: PRT
<213> ORGANISM: Artificial Sequence
<220> FEATURE:
<223> OTHER INFORMATION: Avian influenza hemagglutinin sequence

<400> SEQUENCE: 84

Trp Gly Ile His His Pro Asn Asp Ala
1               5

<210> SEQ ID NO 85
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 85

Trp Leu Ile Lys Lys Asn Asn Ala Tyr
1               5

<210> SEQ ID NO 86
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 86

Trp Leu Leu Gly Asn Pro Met Cys Asp
1               5

<210> SEQ ID NO 87
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 87

Trp Thr Ile Leu Lys Pro Asn Asp Ala
1               5

<210> SEQ ID NO 88
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 88

Tyr Ala Tyr Lys Ile Val Lys Lys Gly
1               5

<210> SEQ ID NO 89
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 89

Tyr Glu Glu Leu Lys His Leu Leu Ser
1               5

<210> SEQ ID NO 90
<211> LENGTH: 9
<212> TYPE: PRT
<213> ORGANISM: Artificial Sequence
```

```
<220> FEATURE:
<223> OTHER INFORMATION: Avian influenza hemagglutinin sequence

<400> SEQUENCE: 90

Tyr Gly Asn Cys Asn Thr Lys Cys Gln
1               5

<210> SEQ ID NO 91
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 91

Tyr His Ala Asn Asn Ser Thr Glu Gln
1               5

<210> SEQ ID NO 92
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 92

Tyr Ile Val Glu Lys Asp Asn Pro Ile
1               5

<210> SEQ ID NO 93
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 93

Tyr Lys Ile Val Lys Lys Gly Asp Ser
1               5

<210> SEQ ID NO 94
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 94

Tyr Asn Gly Arg Ser Ser Phe Phe Arg
1               5

<210> SEQ ID NO 95
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 95

Tyr Asn Asn Thr Asn Gln Glu Asp Leu
1               5

<210> SEQ ID NO 96
<211> LENGTH: 9
<212> TYPE: PRT
<213> ORGANISM: Artificial Sequence
<220> FEATURE:
<223> OTHER INFORMATION: Avian influenza hemagglutinin sequence
```

```
<400> SEQUENCE: 96

Tyr Gln Asn Pro Thr Thr Tyr Val Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 97

Tyr Val Lys Ser Asp Arg Leu Val Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 98

Tyr Val Ser Val Gly Thr Ser Thr Leu
1               5

<210> SEQ ID NO 99
<211> LENGTH: 8
<212> TYPE: PRT
<213> ORGANISM: Artificial Sequence
<220> FEATURE:
<223> OTHER INFORMATION: Avian influenza hemagglutinin sequence

<400> SEQUENCE: 99

His Ala Asn Asn Ser Thr Glu Gln
1               5

<210> SEQ ID NO 100
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 100

Gly Asp Phe Asn Asp Tyr Glu Glu Leu
1               5

<210> SEQ ID NO 101
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 101

Ser Ser Trp Ser Asn His Asp
1               5

<210> SEQ ID NO 102
<211> LENGTH: 13
<212> TYPE: PRT
<213> ORGANISM: Artificial Sequence
<220> FEATURE:
<223> OTHER INFORMATION: Avian influenza hemagglutinin sequence

<400> SEQUENCE: 102
```

```
Pro Thr Ile Lys Arg Ser Tyr Asn Asn Thr Asn Gln Glu
1               5                   10
```

<210> SEQ ID NO 103
<211> LENGTH: 17
<212> TYPE: PRT
<213> ORGANISM: Artificial Sequence
<220> FEATURE:
<223> OTHER INFORMATION: Avian influenza hemagglutinin sequence

<400> SEQUENCE: 103

```
His Pro Asn Asp Ala Ala Glu Gln Thr Lys Leu Tyr Gln Asn Pro Thr
1               5                   10                  15

Thr
```

<210> SEQ ID NO 104
<211> LENGTH: 8
<212> TYPE: PRT
<213> ORGANISM: Artificial Sequence
<220> FEATURE:
<223> OTHER INFORMATION: Avian influenza hemagglutinin sequence

<400> SEQUENCE: 104

```
Ile Ala Thr Arg Pro Lys Val Asn
1               5
```

<210> SEQ ID NO 105
<211> LENGTH: 11
<212> TYPE: PRT
<213> ORGANISM: Artificial Sequence
<220> FEATURE:
<223> OTHER INFORMATION: Avian influenza hemagglutinin sequence

<400> SEQUENCE: 105

```
Asn Val Pro Gln Arg Glu Thr Arg Arg Gln Lys
1               5                   10
```

<210> SEQ ID NO 106
<211> LENGTH: 20
<212> TYPE: PRT
<213> ORGANISM: Artificial Sequence
<220> FEATURE:
<223> OTHER INFORMATION: Avian influenza hemagglutinin sequence

<400> SEQUENCE: 106

```
Ile Val Ile Ala Leu Ala Ile Ile Ser Val Val Lys Gly Asp Gln Ile
1               5                   10                  15

Cys Ile Gly Tyr
            20
```

<210> SEQ ID NO 107
<211> LENGTH: 10
<212> TYPE: PRT
<213> ORGANISM: Artificial Sequence
<220> FEATURE:
<223> OTHER INFORMATION: Avian influenza hemagglutinin sequence

<400> SEQUENCE: 107

```
Asn Val Thr Val Thr His Ala Gln Asp Ile
1               5                   10
```

<210> SEQ ID NO 108
<211> LENGTH: 22
<212> TYPE: PRT
<213> ORGANISM: Artificial Sequence
<220> FEATURE:

<223> OTHER INFORMATION: Avian influenza hemagglutinin sequence

<400> SEQUENCE: 108

Gly Lys Leu Cys Ser Leu Asn Gly Val Lys Pro Leu Ile Leu Arg Asp
1               5                   10                  15

Cys Ser Val Ala Gly Trp
            20

<210> SEQ ID NO 109
<211> LENGTH: 16
<212> TYPE: PRT
<213> ORGANISM: Artificial Sequence
<220> FEATURE:
<223> OTHER INFORMATION: Avian influenza hemagglutinin sequence

<400> SEQUENCE: 109

Asp Glu Phe Leu Asn Val Pro Glu Trp Ser Tyr Ile Val Glu Lys Asp
1               5                   10                  15

<210> SEQ ID NO 110
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 110

Asn Ser Leu Cys Tyr Pro Gly
1               5

<210> SEQ ID NO 111
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 111

Glu Leu Lys His Leu Leu Ser Ser Thr
1               5

<210> SEQ ID NO 112
<211> LENGTH: 8
<212> TYPE: PRT
<213> ORGANISM: Artificial Sequence
<220> FEATURE:
<223> OTHER INFORMATION: Avian influenza hemagglutinin sequence

<400> SEQUENCE: 112

Lys Ile Gln Ile Ile Pro Arg Ser
1               5

<210> SEQ ID NO 113
<211> LENGTH: 11
<212> TYPE: PRT
<213> ORGANISM: Artificial Sequence
<220> FEATURE:
<223> OTHER INFORMATION: Avian influenza hemagglutinin sequence

<400> SEQUENCE: 113

Ser Ser Gly Val Ser Ser Ala Cys Pro Tyr Asn
1               5                   10

<210> SEQ ID NO 114
<211> LENGTH: 8
<212> TYPE: PRT
<213> ORGANISM: Artificial Sequence -continued

```
<220> FEATURE:
<223> OTHER INFORMATION: Avian influenza hemagglutinin sequence

<400> SEQUENCE: 114

Phe Arg Asn Val Val Trp Leu Ile
1               5

<210> SEQ ID NO 115
<211> LENGTH: 8
<212> TYPE: PRT
<213> ORGANISM: Artificial Sequence
<220> FEATURE:
<223> OTHER INFORMATION: Avian influenza hemagglutinin sequence

<400> SEQUENCE: 115

Asp Leu Leu Ile Leu Trp Gly Ile
1               5

<210> SEQ ID NO 116
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 116

Gln Thr Lys Leu Tyr Gln Asn
1               5

<210> SEQ ID NO 117
<211> LENGTH: 9
<212> TYPE: PRT
<213> ORGANISM: Artificial Sequence
<220> FEATURE:
<223> OTHER INFORMATION: Avian influenza hemagglutinin sequence

<400> SEQUENCE: 117

Thr Thr Tyr Val Ser Val Gly Thr Ser
1               5

<210> SEQ ID NO 118
<211> LENGTH: 12
<212> TYPE: PRT
<213> ORGANISM: Artificial Sequence
<220> FEATURE:
<223> OTHER INFORMATION: Avian influenza hemagglutinin sequence

<400> SEQUENCE: 118

Ala Pro Glu Tyr Ala Tyr Lys Ile Val Lys Lys Gly
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Avian influenza hemagglutinin sequence

<400> SEQUENCE: 119

Asn Thr Lys Cys Gln Thr Pro Val Gly Ala Ile
1               5                   10

<210> SEQ ID NO 120
<211> LENGTH: 25
<212> TYPE: PRT
<213> ORGANISM: Artificial Sequence
<220> FEATURE:
<223> OTHER INFORMATION: Avian influenza hemagglutinin sequence
```

```
<400> SEQUENCE: 120

Phe His Asn Ile His Pro Leu Thr Ile Gly Glu Cys Pro Lys Tyr Val
1               5                   10                  15

Lys Ser Asp Arg Leu Val Leu Ala Thr
            20              25

<210> SEQ ID NO 121
<211> LENGTH: 7
<212> TYPE: PRT
<213> ORGANISM: Artificial Sequence
<220> FEATURE:
<223> OTHER INFORMATION: Avian influenza hemagglutinin sequence

<400> SEQUENCE: 121

Phe Gly Ala Ile Ala Gly Phe
1               5
```

DNA SEQUENCES, VECTORS AND PROTEINS OF AVIAN INFLUENZA HEMAGGLUTININ

CROSS-REFERENCE TO RELATED APPLICATION

This application is the U.S. national stage application of International Patent Application No. PCT/US2007/070755, filed Jun. 8, 2007, which claims the benefit of U.S. Provisional Patent Application No. 60/814,241, filed Jun. 16, 2006, the disclosures of which are hereby incorporated by reference in their entireties, including all figures, tables and amino acid or nucleic acid sequences.

The Sequence Listing for this application is labeled "Seq-List-replace.txt" which was created on Jan. 27, 2011 and is 79 KB. The entire contents of the sequence listing is incorporated herein by reference in its entirety.

BACKGROUND OF THE INVENTION

The avian influenza A (H5N1) outbreak in Asia and parts of Europe, the Near East, and Africa is of concern to the general population, and scientists do not expect the disease to diminish significantly in the short term. Additionally, the H5N1 infection among birds has, likely, become endemic in certain areas and human infections resulting from direct contact with infected poultry will continue to occur. H5N1 virus transmission from person-to-person has been rare and has not continued beyond one person and no evidence for genetic reassortment between human and avian influenza A virus genes has been found; however, avian influenza is still considered to pose an important public health threat.

Research suggests that currently circulating strains of H5N1 viruses are becoming more pathogenic in animals than were earlier H5N1 viruses. Animals, such as ducks, have been found to be shedding more viruses for longer periods without showing symptoms of illness. This finding has implications for the role of ducks in transmitting disease to other birds and possibly to humans as well. H5N1 infection among pigs in China and H5N1 infection in felines has also been documented. Germany has also reported a H5N1 infection in a stone marten.

The human population has little pre-existing natural immunity to H5N1 infection. Thus, if H5N1 viruses gain the ability for efficient and sustained transmission among humans, an influenza pandemic could result. Such a pandemic has the potential for high rates of illness and death. Added into the equation is the finding that influenza A (H5N1) viruses can show resistance to antiviral medications such as amantadine and rimantadine. These two medications are commonly used for treatment of influenza. Accordingly, there is a need to produce vaccine candidates that would be effective against avian influenza A (H5N1) viruses.

BRIEF SUMMARY OF THE INVENTION

The subject invention provides novel amino acid sequences (including a consensus sequence) of the Avian Influenza A virus hemagglutinin (HA) protein. These newly constructed genes are designed to provide a broader spectrum of activity across the serotype family thus providing a basis for a vaccine that has broad heterologous disease protection. The novel genes have been further improved by the addition of strategic glycosylation sites into the amino acids sequences that they encode. These genes can also, optionally, be codon optimized for plant expression, inserted into the appropriate vector and cloned into plants for expression. Polypeptides produced by recombinant host cells or transgenic plants can also be used as source of antigen for the formulation of vaccines for the control of influenza in susceptible individuals. Additionally, transgenic plant material may also be used as source of antigen for the formulation of vaccines for the control of influenza in susceptible individuals.

BRIEF DESCRIPTION OF THE FIGURES

FIGS. 1-3 provide various peptide fragments of SEQ ID NO: 14 that are predicted to interact with MHC I and CTL (cytotoxic T lymphocytes) (FIG. 1), MHC Class II (FIG. 2), or antibody molecules (FIG. 3).

BRIEF DESCRIPTION OF THE SEQUENCES

Figure 4:
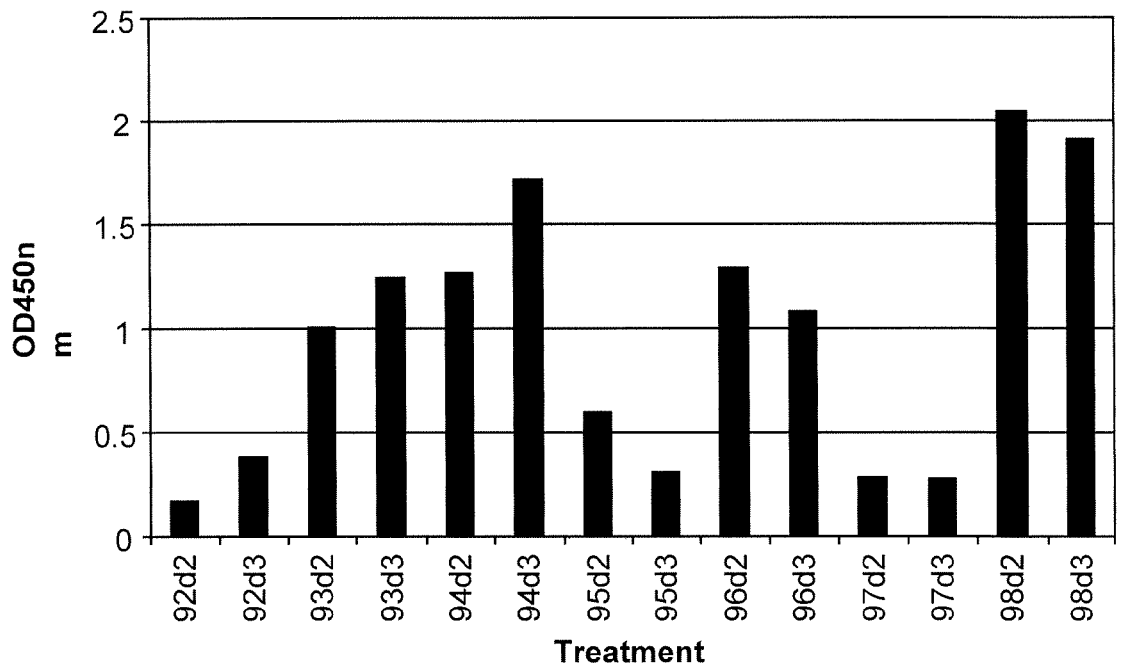
FIG. 4 demonstrates transient expression of synthetic HA genes in plants (observed using binary vectors pDAB4492-pDAB4498). The bars represent the average OD of two repetitions of crude extracts made from 7 pooled samples taken 2 or 3 days after inoculation. The ODs of wild type plant leaves were subtracted from the transgenic sample ODs after averaging. "92" represents pDAB4492; "93", pDAB4493; "94", pDAB4494, "95", pDAB4405; "96", pDAB4496; "97", pDAB4497; "98", pDAB4498; "d2", day 2 and "d3", day 3.

SEQ ID NO: 1 provides a polynucleotide sequence encoding hemagglutinin V1 (HA original turkey Wisconsin 68 minus cleavage site).

SEQ ID NO: 2 corresponds to the polypeptide encoded by SEQ ID NO: 1.

SEQ ID NO: 3 illustrates hemagglutinin V2 (containing a glycosylation site at amino acid 239).

SEQ ID NO: 4 is the amino acid sequence encoded by SEQ ID NO: 3.

SEQ ID NO: 5 provides a polynucleotide sequence encoding hemagglutinin V3 (including the RQKR cleavage site of the native turkey Wisconsin 68 hemagglutinin protein).

SEQ ID NO: 6 corresponds to the polypeptide encoded by SEQ ID NO: 5.

SEQ ID NO: 7 illustrates hemagglutinin V4 (providing amino acid modifications at positions 99, 102, and 170).

SEQ ID NO: 8 is the amino acid sequence encoded by SEQ ID NO: 7.

SEQ ID NO: 9 provides a polynucleotide sequence encoding hemagglutinin V5 (providing amino acid modifications at positions 99, 102, and 239.

SEQ ID NO: 10 corresponds to the polypeptide encoded by SEQ ID NO: 9.

SEQ ID NO: 11 illustrates DNA encoding hemagglutinin V6 (containing amino acid modifications at positions 99, 102, 170, and 239).

SEQ ID NO: 12 is the amino acid sequence encoded by SEQ ID NO: 11.

SEQ ID NO: 13 is a plant optimized nucleic acid sequence encoding an "ancestral" HA polypeptide of the subject invention. The term "ancestral HA polypeptide" refers to hemagglutinin polypeptide deduced using bioinformatics.

SEQ ID NO: 14 is an "ancestral" sequence provided by the subject invention. The term "ancestral HA polypeptide" refers to hemagglutinin polypeptide deduced using bioinformatics.

SEQ ID NO: 15 is a primer for amplification of HA genes.

SEQ ID NO: 16 is a primer for amplification of HA genes.

BRIEF DESCRIPTION OF THE TABLES

Tables 1a-1b specify the N-terminal and C-terminal amino acid positions for fragments of SEQ ID NOs: 2, 4, 8, 10 and 14. The fragment can be any number (integer) of consecutive amino acids between, and including, 5 and 563, the N-terminal amino acid can be any integer between, and including, 1 and 560 (see Table 1a) and the C-terminal amino acid can be any position selected from any integer identified in Table 1b (i.e., 5 through 564).

Tables 2a-2b specify the N-terminal and C-terminal amino acid positions for fragments of SEQ ID NO: 6. The fragment can be any number (integer) of consecutive amino acids between, and including, 5 and 567, the N-terminal amino acid can be any integer between, and including, 1 and 564 (see Table 2a) and the C-terminal amino acid can be any position selected from any integer identified in Table 2b (i.e., 5 through 568).

Tables 3a-3b specify the N-terminal and C-terminal amino acid positions for fragments of SEQ ID NO: 12. The fragment can be any number (integer) of consecutive amino acids between, and including, 5 and 552, the N-terminal amino acid can be any integer between, and including, 1 and 549 (see Table 3a) and the C-terminal amino acid can be any position selected from any integer identified in Table 3b (i.e., 5 through 553).

Table 4. Stable expression of AIV HA in NT1 plant cell cultures. The first two digits of the line number indicate the plasmid construct (pDAB44xx).

DETAILED DESCRIPTION OF THE INVENTION

The subject application provides the following non-limiting compositions of matter as well as methods of using these compositions of matter in the production of immunogenic polypeptides and methods of inducing immune responses in individuals. Thus, the subject invention provides various compositions of matter comprising:

a) isolated, purified, and/or recombinant polypeptides comprising SEQ ID NO: 2, 4, 6, 8, 10, 12 or 14;

b) variant polypeptides having at least about 20% to 99.99% identity, preferably at least 60 to 99.99% identity to the polypeptide of SEQ ID NO: 2, 4, 6, 8, 10, 12 or 14 and which has at least one of the biological activities associated with the polypeptide of SEQ ID NO: 2, 4, 6, 8, 10, 12 or 14;

c) a fragment of the polypeptide (or variant polypeptide) of SEQ ID NO: 2, 4, 6, 8, 10, 12 or 14, a fragment of SEQ ID NO: 2, 4, 6, 8, 10, 12 or 14 that is "from Y to Z", wherein Y is the N-terminal amino acid of the specified sequence and Z is the C-terminal amino acid of the specified sequence, the fragment is at least 5 amino acids in length, and Y and Z are any integer specified (or selected from) those integers identified in Tables 1 through 3 for a specified SEQ ID NO:, or a polypeptide fragment or as illustrated in FIG. 1, 2 or 3, wherein said polypeptide fragment or fragment of said variant polypeptide has at least one biological activity that is substantially the same as the corresponding biological activity of the polypeptide of SEQ ID NO: 2, 4, 6, 8, 10, 12 or 14 (additional exemplary fragments within the context of the invention include a leader sequence spanning amino acids 1 to 16 of each of SEQ ID NO: 2, 4, 6, 8, 10, 12 or 14, the span of amino acids comprising or consisting of position 17 to position 342 (corresponding to the H1 region of the hemagglutinin polypeptide) of each of SEQ ID NO: 2, 4, 6 8, 10, 12 or 14 and the H2 region of the hemagglutinin polypeptide comprising or consisting of: the span of amino acids corresponding to position 343 to position 364 for SEQ ID NO: 2, 4, 8, 10 or 14; the span of amino acids corresponding to position 343 to position 568 for SEQ ID NO: 6; or the span of amino acids from position 343 to position 553 of SEQ ID NO: 12);

d) an epitope of a polypeptide (or a variant polypeptide) selected from the group consisting SEQ ID NO: 2, 4, 6, 8, 10, 12 and 14;

e) a multi-epitope construct comprising at least one epitope as set forth herein; or f) a polypeptide according to any one of embodiments a), b), c), d) or e) that further comprises a heterologous polypeptide sequence;

g) a plant-derived polypeptide according to any one of embodiments a), b), c), d), e) or f);

h) a composition comprising a carrier and a polypeptide as set forth in any one of a), b), c), d), e), f) or g), wherein said carrier is an adjuvant or a pharmaceutically acceptable excipient;

i) a polynucleotide sequence encoding a polypeptide comprising SEQ ID NO: 2, 4, 6, 8, 10, 12 or 14 or encoding one or more polypeptide fragment of SEQ ID NOs: 2, 4, 6, 8, 10, 12 or 14 as set forth in (c);

j) a polynucleotide sequence encoding a polypeptide having between 20% to 99.99% sequence homology or identity to a polypeptide comprising SEQ ID NO: 2, 4, 6, 8, 10, 12 or 14 or one or more polypeptide fragment of SEQ ID NOs: 2, 4, 6, 8, 10, 12 or 14, wherein said polypeptide has at least one of the biological activities associated with comprising SEQ ID NO: 2, 4, 6, 8, 10, 12 or 14 or one or more polypeptide fragment of SEQ ID NOs: 2, 4, 6, 8, 10, 12 or 14;

k) a polynucleotide sequence having at least about 20% to 99.99% identity to a polynucleotide sequence comprising SEQ ID NO: 1, 3, 5, 7, 9, 11 or 13;

l) a polynucleotide sequence comprising SEQ ID NO: 1, 3, 5, 7, 9, 11 or 13 or a fragment of at least 8 consecutive nucleotides of SEQ ID NO: 1, 3, 5, 7, 9, 11 or 13;

m) a polynucleotide that is complementary to the polynucleotides set forth in (i), (j), (k), or (l);

n) a polynucleotide that hybridizes under low, intermediate or high stringency with a polynucleotide sequence as set forth in (i), (j), (k), (l) or (m);

o) a genetic construct comprising a polynucleotide sequence as set forth in (i), (j), (k), (l) or (m);

p) a vector comprising a polynucleotide or genetic construct as set forth in (i), (j), (k), (l), (m) or (n);

q) a host cell comprising a vector as set forth in (p), a genetic construct as set forth in (o), or a polynucleotide as set forth in any one of (i), (j), (k), (l) or (m);

r) a transgenic plant, plant cell, or plant part comprising a vector as set forth in (p), a genetic construct as set forth in (o) or a polynucleotide as set forth in any one of (i), (j), (k), (l) or (m); or s) a probe comprising a polynucleotide according to (i), (j), (k), (l), (m) or (n) and, optionally, a label or marker.

In the context of the instant invention, the terms "oligopeptide", "polypeptide", "peptide" and "protein" can be used interchangeably; however, it should be understood that the invention does not relate to the polypeptides in natural form, that is to say that they are not in their natural environment but that the polypeptides may have been isolated or obtained by purification from natural sources or obtained from host cells prepared by genetic manipulation (e.g., the polypeptides, or fragments thereof, are recombinantly produced by host cells, or by chemical synthesis). Polypeptides according to the instant invention may also contain non-natural amino acids, as will be described below. The terms "oligopeptide", "polypeptide", "peptide" and "protein" are also used, in the instant specification, to designate a series of residues, typically L-amino acids, connected one to the other, typically by peptide bonds between the α-amino and carboxyl groups of adjacent amino acids. Linker elements can be joined to the polypeptides of the subject invention through peptide bonds or via chemical bonds (e.g., heterobifunctional chemical linker elements) as set forth below. Additionally, the terms "amino acid(s)" and "residue(s)" can be used interchangeably.

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods. The terms "polynucleotide vaccine" and "DNA vaccine" can also be used interchangeably herein.

The terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment. "Link" or "join" refers to any method known in the art for functionally connecting peptides, including, without limitation, recombinant fusion, covalent bonding, disulfide bonding, ionic bonding, hydrogen bonding, and electrostatic bonding.

Thus, the subject invention provides hemagglutinin polypeptides comprising SEQ ID NOs: 2, 4, 6, 8, 10, 12 or 14 and/or polypeptide fragments of SEQ ID NOs: 2, 4, 6, 8, 10, 12 or 14 (such as those illustrated in FIG. 1, 2 or 3). In some embodiments of the subject invention, polypeptide fragments of the subject invention that are bound by antibodies or T-cell receptors are designated "epitopes"; in the context of the subject invention, "epitopes" are considered to be a subset of the invention designated as "fragments of SEQ ID NOs: 2, 4, 6, 8, 10, 12 or 14".

Polypeptide fragments (and/or epitopes), according to the subject invention comprise a contiguous span of at least 5 consecutive amino acids of SEQ ID NOs: 2, 4, 6, 8, 10, 12 or 14. Polypeptide fragments according to the subject invention can be any integer in length from at least 5 consecutive amino acids to 1 amino acid less than a full length polypeptide of SEQ ID NO: 2, 4, 6, 8, 10, 12 or 14. Thus, for SEQ ID NO: 2, 4, 8, 10 or 14, a polypeptide fragment is any number (integer) of consecutive amino acids between, and including, 5 and 563. For SEQ ID NO: 6, a polypeptide fragment is any number (integer) of consecutive amino acids between, and including, 5 and 567. For SEQ ID NO: 12, a polypeptide fragment is any number (integer) of consecutive amino acids between, and including 5 and 552 amino acids. Additional exemplary fragments within the context of the invention include a leader sequence spanning amino acids 1 to 16 of each of SEQ ID NO: 2, 4, 6, 8, 10, 12 or 14, the span of amino acids comprising or consisting of position 17 to position 342 (corresponding to the H1 region of the hemagglutinin polypeptide) of each of SEQ ID NO: 2, 4, 6 8, 10, 12 or 14 and the H2 region of the hemagglutinin polypeptide comprising or consisting of: the span of amino acids corresponding to position 343 to position 364 for SEQ ID NO: 2, 4, 8, 10 or 14; the span of amino acids corresponding to position 343 to position 568 for SEQ ID NO: 6; or the span of amino acids from position 343 to position 553 of SEQ ID NO: 12).

Each polypeptide fragment of the subject invention can also be described in terms of its N-terminal and C-terminal positions. For example, combinations of N-terminal to C-terminal fragments of 6 contiguous amino acids to 1 amino acid less than the full length polypeptide of SEQ ID No: 2 are included in the present invention. Thus, a 6 consecutive amino acid fragment could occupy positions selected from the group consisting of 1-6, 2-7, 3-8, 4-9, 5-10, etc. Additionally, polypeptide fragments embodiments described herein may be "at least", "equal to", "equal to or less than", "less than", "at least _____ but not greater than _____" or "from Y to Z", wherein Y is the N-terminal amino acid of the specified sequence and Z is the C-terminal amino acid of the specified sequence, the fragment is at least 5 amino acids in length, and Y and Z are any integer specified (or selected from) those integers identified in Tables 1 through 3. As is apparent from Table 1, the N-terminal amino acid (specified in Table 1a) for fragments of SEQ ID NOs: 2, 4, 8, 10 or 14 can be any integer between 1 and 560 and the C-terminal amino acid (specified in Table 1b) is any integer from 5 to 564

(depending on the fragment length which is to be is any number (integer) of consecutive amino acids between, and including, 5 and 563). For fragments of SEQ ID NO: 6, the N-terminal amino acid can be any integer between 1 and 564 (as specified in Table 2a) and the C-terminal amino acid (as specified in Table 2b) is any integer from 5 to 568 (depending on the fragment length which is to be any number (integer) of consecutive amino acids between, and including, 5 and 567). With respect to fragments of SEQ ID NO: 12, the N-terminal amino acid can be any integer between 1 and 549 (as indicated in Table 3a) and the C-terminal amino acid (indicated in Table 3b) is any integer from 5 to 553 (depending on the fragment length which is any number (integer) of consecutive amino acids between, and including, 5 and 552 amino acids). It is noted that all ranges used to describe any embodiment of the present invention are inclusive unless specifically set forth otherwise and that fragments of a given polypeptide can be any integer in length, provided that the length of the polypeptide fragment is at least one amino acid shorter than the polypeptide identified in SEQ ID NO: 2, 4, 6, 8, 10, 12 or 14.

The subject invention also provides for various peptide fragments (comprising contiguous spans or consecutive spans of at least five consecutive amino acids) that span particular residues of SEQ ID NO: 2, 4, 6, 8, 10, 12 or 14. For SEQ ID NO: 2, preferred fragments include those of at least five consecutive amino acids that contain or span amino acid number 99 of SEQ ID NO: 2. With respect to SEQ ID NO: 4, preferred fragments comprise spans of at least five consecutive amino acids that contain amino acid 239 of SEQ ID NO: 4. Preferred fragments spanning at least five consecutive amino acids of SEQ ID NO: 6 include those containing or spanning: amino acid 326; amino acid 327; amino acid 328; amino acid 329; amino acids 326 and 327; amino acids 327 and 328; amino acids 328 and 329; amino acids 326, 327 and 328; amino acids 327, 328 and 329; or amino acids 326, 327, 328 and 329. For SEQ ID NO: 8, preferred fragments (spanning at least five consecutive amino acids of SEQ ID NO: 8) are those that contain or span: amino acid 99; amino acid 102; amino acid 170; amino acids 99 and 102; amino acids 102 and 170; or amino acids 99, 102 and 170. Preferred fragments of SEQ ID NO: 10 are those spans of at least five consecutive amino acids that include or contain: amino acid 99; amino acid 102; amino acid 239; amino acids 99 and 102; amino acids 102 and 239; or amino acids 99, 102 and 239. As relates to SEQ ID NO: 12, preferred fragments are those that comprise spans of at least 5 consecutive amino acids that include: amino acid 99; amino acid 102; amino acid 170; amino acid 239; amino acids 99 and 102; amino acids 102 and 170; amino acids 170 and 239; amino acids 99, 102 and 170; amino acids 102, 170 and 239; or amino acids 99, 102, 170, and 239.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector according to the invention. The transformed host cells contain a nucleic acid, allowing the expression of these fragments, under the control of appropriate elements for regulation and/or expression of the polypeptide fragments.

In certain preferred embodiments, fragments of the polypeptides disclosed herein retain at least one property or activity of the full-length polypeptide from which the fragments are derived. Thus, both full length polypeptides and fragments of the polypeptides provided by SEQ ID NO: 2, 4, 6, 8, 10, 12 or 14 have one or more of the following properties or biological activities: the ability to: 1) specifically bind to antibodies specific for SEQ ID NO: 2, 4, 6, 8, 10, 12 or 14; 2) specifically bind antibodies found in an animal or human infected with an avian influenza virus; the ability to bind to, and activate T-cell receptors (CTL (cytotoxic T-lymphocyte) and/or HTL (helper T-lymphocyte receptors)) in the context of MHC Class I or Class II antigen that are isolated or derived from an animal or human infected with an avian influenza virus; 3) the ability to induce an immune response in an animal or human against an avian influenza virus; 4) the ability to induce a protective immune response in an animal or human against an avian influenza virus. In certain aspects of the invention, the properties or biological activities are directed to avian influenza viruses of the H5 serotype or avian influenza A.

Where plant expression systems are used for the production of polypeptides, variant polypeptides or fragments of the polypeptides or variant polypeptides provided by this application, a composition comprising the purified polypeptide can include plant cell components (e.g., cell walls, the cellular matrix of plant cell membranes and carbohydrates, etc.) or plant cell matrix components. Likewise, where eukaryotic or prokaryotic expression systems are used for the production of polypeptides, variant polypeptides or fragments of the polypeptides or variant polypeptides provided by this application, cell membrane or cell wall components of each respective expression system may be present in a composition comprising partially purified polypeptides.

The polypeptides (or fragments thereof) of the invention may be monomeric or multimeric (e.g., dimers, trimers, tetramers and higher multimers). Accordingly, the present invention relates to monomers and multimers of the polypeptides of the invention, their preparation, and compositions containing them. Multimeric polypeptides of the subject invention can be derived from the same polypeptide sequence ("homomultimers") or derived from different sequences disclosed herein ("heteromultimers"). A homomultimer may contain polypeptides having identical or different amino acid sequences; however these sequences are derived from the same original polypeptide (i.e., SEQ ID NO: 2, 4, 6, 8, 10, 12 or 14). A heteromultimer refers to a multimeric polypeptide containing one or more heterologous polypeptides (i.e., polypeptides of different proteins) in addition to the polypeptides of the invention. Thus, a heteromultimer, in the context of the subject invention can refer to a multimeric polypeptide that contains any combination of SEQ ID NOs: 2, 4, 6, 8, 10, 12 or 14 (or fragments thereof). Alternatively, a heteromultimeric polypeptide may comprise any one of SEQ ID NOs: 2, 4, 6, 8, 10, 12 or 14 fused to a polypeptide or other element that forms a hydrophobic, hydrophilic, ionic and/or covalent association.

Multimeric polypeptides, as set forth herein, may be formed by hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. One non-limiting example of such a covalent association is the formation disulfide bonds between immunoglobulin heavy chains as provided by a fusion protein of the invention that comprises a polypeptide comprising SEQ ID NO: 2, 4, 6, 8, 10, 12 or 14 (or fragments thereof) fused to an Ig heavy chain (see, e.g., U.S. Pat. No. 5,478,925, which disclosure is hereby incorporated by reference in its entirety). Another example of a fusion protein capable of forming covalently associated multimers is osteoprotegerin (see, e.g., International Publication No: WO 98/49305, the contents of which is incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Other multimeric polypeptides can be formed by fusing the polypeptides of the invention to a leucine zipper or isoleucine zipper polypeptide sequence. Leucine zipper and isoleucine zipper domains are polypeptides that promote multimerization of the proteins in which they are found. Non-limiting examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Multimeric polypeptides can also be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimeric polypeptides can be generated by introducing disulfide bonds between the cysteine residues located within the sequence of the polypeptides that are being used to construct the multimeric polypeptide (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478, 925, which is herein incorporated by reference in its entirety). Additionally, other techniques known in the art may be applied to generate liposomes containing the polypeptide components desired to be contained in the multimer of the invention (see, e.g., U.S. Pat. No. 5,478,925, which is herein incorporated by reference in its entirety).

The polypeptides provided herein, as well as the fragments thereof, may further comprise linker elements (L) that facilitate the attachment of the fragments to other molecules, amino acids, or polypeptide sequences. The linkers can also be used to attach the polypeptides, or fragments thereof, to solid support matrices for use in affinity purification protocols. Non-limiting examples of "linkers" suitable for the practice of the invention include chemical linkers (such as those sold by Pierce, Rockford, Ill.), or peptides that allow for the connection combinations of polypeptides (see, for example, linkers such as those disclosed in U.S. Pat. Nos. 6,121,424, 5,843,464, 5,750,352, and 5,990,275, hereby incorporated by reference in their entirety).

In other embodiments, the linker element (L) can be an amino acid sequence (a peptide linker). In some embodiments, the peptide linker has one or more of the following characteristics: a) it allows for the free rotation of the polypeptides that it links (relative to each other); b) it is resistant or susceptible to digestion (cleavage) by proteases; and c) it does not interact with the polypeptides it joins together. In various embodiments, a multimeric construct according to the subject invention includes a peptide linker and the peptide linker is 5 to 60 amino acids in length. More preferably, the peptide linker is 10 to 30, amino acids in length; even more preferably, the peptide linker is 10 to 20 amino acids in length. In some embodiments, the peptide linker is 17 amino acids in length.

Peptide linkers suitable for use in the subject invention are made up of amino acids selected from the group consisting of Gly, Ser, Asn, Thr and Ala. Preferably, the peptide linker includes a Gly-Ser element. In a preferred embodiment, the peptide linker comprises (Ser-Gly-Gly-Gly-Gly)$_y$ (SEQ ID NO: 17) wherein y is 1, 2, 3, 4, 5, 6, 7, or 8. Other embodiments provide for a peptide linker comprising ((Ser-Gly-Gly-Gly-Gly)$_y$-Ser-Pro) (SEQ ID NO: 18). In certain preferred embodiments, y is a value of 3, 4, or 5. In other preferred embodiment, the peptide linker comprises (Ser-Ser-Ser-Ser-Gly)$_y$ (SEQ ID NO: 19) or ((Ser-Ser-Ser-Ser-Gly)$_y$-Ser-Pro) (SEQ ID NO: 20), wherein y is 1, 2, 3, 4, 5, 6, 7, or 8. In certain preferred embodiments, y is a value of 3, 4, or 5. Where cleavable linker elements are desired, one or more cleavable linker sequences such as Factor Xa or enterokinase (Invitrogen, San Diego Calif.) can be used alone or in combination with the aforementioned linkers.

Multimeric constructs of the subject invention can also comprise a series of repeating elements, optionally interspersed with other elements. As would be appreciated by one skilled in the art, the order in which the repeating elements occur in the multimeric polypeptide is not critical and any arrangement of the repeating elements as set forth herein can be provided by the subject invention. Thus, a "multimeric construct" according to the subject invention can provide a multimeric polypeptide comprising a series of polypeptides, polypeptide fragments, or epitopes that are, optionally, joined together by linker elements (either chemical linker elements or amino acid linker elements).

A "variant polypeptide" (or polypeptide variant) is to be understood to designate polypeptides exhibiting, in relation to the natural polypeptide, certain modifications. These modifications can include a deletion, addition, or substitution of at least one amino acid, a truncation, an extension, a chimeric fusion (fusion protein), a mutation, or polypeptides exhibiting post-translational modifications. Among these homologous variant polypeptides, are those comprising amino acid sequences exhibiting between at least (or at least about) 20.00% to 99.99% (inclusive) identity to the full length, native, or naturally occurring polypeptide are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length. Thus, variant polypeptides can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polypeptide sequences of the instant invention. In a preferred embodiment, a variant or modified polypeptide exhibits at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to SEQ ID NO: 2, 4, 6, 8, 10, 12 or 14. The percent identity is calculated with reference to the full-length polypeptide or the length of the fragment of a particular SEQ ID NO: that is identified (e.g., those polypeptides set forth in SEQ ID NO: 2, 4, 6, 8, 10, 12, 14 or fragments thereof). In all instances, variant polypeptides retain at least one of the biological activities associated with the polypeptide set forth in SEQ ID NOs: 2, 4, 6, 8, 10, 12 or 14 (for example, the ability to induce an immune response in an individual or the ability to induce a protective immune response in an individual). Specifically excluded from the definition of "variant polypeptides" and "fragments of variant polypeptides" are those influenza hemagglutinin polypeptides provided in publicly available databases. For example, Influenza A virus (A/duck/ Hong Kong/698/79(H5N3)), Accession No. AAD13571 (AF082039) is specifically excluded as a variant polypeptide.

Fusion proteins according to the subject invention comprise one or more heterologous polypeptide sequences (e.g., tags that facilitate purification of the polypeptides of the invention (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli*," *J. of Experimental* Biology 203:19-28, The Co. of Biologists, Ltd., G. B.; Baneyx [1999] "Recombinant Protein Expression in *Escherichia coli*," Biotechnology 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. "Current Trends in Molecular Recognition and Bioseparation," *J. of Chromatography A.* 707:3-22, Elsevier Science B.V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: the Strep-tag", *Biomolecular Engineering* 16:79-86, Elsevier Science, B.V.; Smith [1998] "Cookbook for Eukaryotic Protein Expression: Yeast, Insect, and Plant Expression Systems," *The* Scientist 12(22):20; Smyth et al. [2000] "Eukaryotic Expression and Purification of Recombinant Extracellular Matrix Proteins Carrying the Strep II Tag", *Methods in Molecular Biology,* 139:49-57; Unger [1997] "Show Me the Money: Prokaryotic Expression Vectors and Purification Systems," *The Scientist* 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.).

In other embodiments, polypeptides of the subject invention (e.g., SEQ ID NOs: 2, 4, 6, 8, 10, 12 and/or 14 or fragments thereof) can be fused to heterologous polypeptide sequences that have adjuvant activity (a polypeptide adjuvant). Non-limiting examples of such polypeptides include heat shock proteins (hsp) (see, for example, U.S. Pat. No. 6,524,825, the disclosure of which is hereby incorporated by reference in its entirety).

Also included within the scope of the subject invention are at least one or more polypeptide fragments of SEQ ID NO: 2, 4, 6, 8, 10, 12 or 14 that are an "epitope". In the context of the subject invention, an the term "epitope" is used to designate a series of residues, typically L-amino acids, connected one to the other, typically by peptide bonds between the α-amino and carboxyl groups of adjacent amino acids. The preferred CTL (or CD8$^+$ T cell)-inducing peptides of the invention are 13 residues or less in length and usually consist of between about 8 and about 11 residues (e.g., 8, 9, 10 or 11 residues), preferably 9 or 10 residues. The preferred HTL (or CD4$^+$ T cell)-inducing peptides are less than about 50 residues in length and usually consist of between about 6 and about 30 residues, more usually between about 12 and 25 (e.g., 12, 13, 14, 15, 16, 17, 18, 19, 20, 21, 22, 23, 24 or 25), and often between about 15 and 20 residues (e.g., 15, 16, 17, 18, 19 or 20).

The subject invention also provides biologically active fragments (epitopes) of a polypeptide according to the invention and includes those peptides capable of eliciting an immune response directed against an H5 serotype influenza virus, said immune response providing components (B-cells, antibodies, and/or or components of the cellular immune response (e.g., helper, cytotoxic, and/or suppressor T-cells)) reactive with the fragment of said polypeptide; the intact, full length, unmodified polypeptide disclosed herein; or both a fragment of a polypeptide and the intact, full length, unmodified polypeptides disclosed herein.

The subject application also provides a composition comprising at least one isolated, recombinant, or purified polypeptide comprising SEQ ID NO: 2, 4, 6, 8, 10, 12 or 14 (or a fragment thereof) and at least one additional component. In various aspects of the invention, the additional component is a solid support (for example, microtiter wells, magnetic beads, non-magnetic beads, agarose beads, glass, cellulose, plastics, polyethylene, polypropylene, polyester, nitrocellulose, nylon, or polysulfone). The additional component can also be a pharmaceutically acceptable excipient or adjuvant known to those skilled in the art. In some aspects of the invention, the solid support provides an array of polypeptides of the subject invention or an array of polypeptides comprising combinations of various polypeptides of the subject invention.

The subject invention also provides methods for eliciting an immune response in an individual comprising the administration of compositions comprising polypeptides according to the subject invention to an individual in amounts sufficient to induce an immune response in the individual. In some embodiments, a "protective" or "therapeutic immune response" is induced in the individual. A "protective immune response" or "therapeutic immune response" refers to a CTL (or CD8$^+$ T cell) and/or an HTL (or CD4$^+$ T cell), and/or an antibody response that prevents, reduces or at least partially arrests disease symptoms, side effects or progression the individuals. For example, individuals in which a protective immune response has been induced can exhibit reduced mortality and/or exhibit reduced viral shedding as compared to non-immunized control individuals. The protective immune response may also include an antibody response that has been facilitated by the stimulation of helper T cells (or CD4$^+$ T cells). Additional methods of inducing an immune response in an individual are taught in U.S. Pat. No. 6,419,931, hereby incorporated by reference in its entirety. The term CTL can be used interchangeably with CD8+ T-cell(s) and the term HTL can be used interchangeably with CD4+ T-cell(s) throughout the subject application.

Individuals, in the context of this application, refer to birds and/or mammals such as, but not limited to, apes, chimpanzees, orangutans, humans, monkeys or domesticated animals (pets) such as dogs, cats, guinea pigs, hamsters, rabbits, ferrets, cows, horses, goats and sheep. Avian or bird is herein defined as any warm-blooded vertebrate member of the class Aves typically having forelimbs modified into wings, scaly legs, a beak, and bearing young in hard-shelled eggs. For purposes of this specification, preferred groups of birds are domesticated chickens, turkeys, ostriches, ducks, geese, swan, and cornish game hens. A more preferred group is domesticated chickens and turkeys.

Administering or administer is defined as the introduction of a substance into the body of an individual and includes oral, nasal, ocular, rectal, vaginal and parenteral routes. Compositions may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN), or orally.

The composition administered to the individual may, optionally, contain an adjuvant and may be delivered in any manner known in the art for the delivery of immunogen to a subject. Compositions may also be formulated in any carriers, including for example, pharmaceutically acceptable carriers such as those described in E. W. Martin's *Remingion's Pharmaceutical Science*, Mack Publishing Company, Easton, Pa. In preferred embodiments, compositions may be formulated in incomplete Freund's adjuvant, complete Freund's adjuvant, or alum.

In other embodiments, the subject invention provides for diagnostic assays based upon Western blot formats or standard immunoassays known to the skilled artisan and which utilize a polypeptide comprising, consisting essentially of, or consisting of SEQ ID NO: 2, 4, 6, 8, 10, 12 or 14. For example, antibody-based assays such as enzyme linked immunosorbent assays (ELISAs), radioimmunoassays (RIAs), lateral flow assays, reversible flow chromatographic binding assay (see, for example, U.S. Pat. No. 5,726,010, which is hereby incorporated by reference in its entirety), immunochromatographic strip assays, automated flow assays, and assays utilizing peptide-containing biosensors may be employed for the detection of antibodies that bind to the polypeptides (or fragments thereof) that are provided by the subject invention. The assays and methods for conducting the assays are well-known in the art and the methods may test biological samples (e.g., serum, plasma, or blood) qualitatively (presence or absence of antibody) or quantitatively (comparison of a sample against a standard curve prepared using a polypeptide of the subject invention) for the presence of antibodies that bind to polypeptides of the subject invention.

The antibody-based assays can be considered to be of four types: direct binding assays, sandwich assays, competition assays, and displacement assays. In a direct binding assay, either the antibody or antigen is labeled, and there is a means of measuring the number of complexes formed. In a sandwich assay, the formation of a complex of at least three components (e.g., antibody-antigen-antibody) is measured. In a competition assay, labeled antigen and unlabelled antigen compete for binding to the antibody, and either the bound or the free component is measured. In a displacement assay, the labeled antigen is pre-bound to the antibody, and a change in signal is measured as the unlabelled antigen displaces the bound, labeled antigen from the receptor.

Lateral flow assays can be conducted according to the teachings of U.S. Pat. No. 5,712,170 and the references cited therein. U.S. Pat. No. 5,712,170 and the references cited therein are hereby incorporated by reference in their entireties. Displacement assays and flow immunosensors useful for carrying out displacement assays are described in: (1) Kusterbeck et al., "Antibody-Based Biosensor for Continuous Monitoring", in Biosensor Technology, R. P. Buck et al., eds., Marcel Dekker, N.Y. pp. 345-350 (1990); Kusterbeck et al., "A Continuous Flow Immunoassay for Rapid and Sensitive Detection of Small Molecules", Journal of Immunological Methods, vol. 135, pp. 191-197 (1990); Ligler et al., "Drug Detection Using the Flow Immunosensor", in Biosensor Design and Application, J. Findley et al., eds., American Chemical Society Press, pp. 73-80 (1992); and Ogert et al., "Detection of Cocaine Using the Flow Immunosensor", Analytical Letters, vol. 25, pp. 1999-2019 (1992), all of which are incorporated herein by reference in their entireties. Displacement assays and flow immunosensors are also described in U.S. Pat. No. 5,183,740, which is also incorporated herein by reference in its entirety. The displacement immunoassay, unlike most of the competitive immunoassays used to detect small molecules, can generate a positive signal with increasing antigen concentration.

The subject invention also provides methods of binding an antibody to a polypeptide of the subject invention (e.g., SEQ ID NO: 2, 4, 6, 8, 10, 12 or 14, of an antibody binding fragment thereof) comprising contacting a sample containing an antibody with a polypeptide under conditions that allow for the formation of an antibody-antigen complex. These methods can further comprise the step of detecting the formation of said antibody-antigen complex. In various aspects of this method, an immunoassay is conducted for the detection of an H5 serotype influenza virus. Non-limiting examples of such immunoassays include enzyme linked immunosorbent assays (ELISAs), radioimmunoassays (RIAs), lateral flow assays, immunochromatographic strip assays, automated flow assays, Western blots, immunoprecipitation assays, reversible flow chromatographic binding assays, agglutination assays, and biosensors. Additional aspects of the invention provide for the use of an array of polypeptides when conducting the aforementioned methods of detection (the array can contain at least one of the polypeptides set forth in SEQ ID NOs: 2, 4, 6, 8, 10, 12 or 14 (or fragments thereof) and can also contain other polypeptides of the same or different influenza serotype.

The subject invention also concerns antibodies that bind to polypeptides of the invention. Antibodies that are immunospecific for the polypeptides as set forth herein are specifically contemplated. In various embodiments, antibodies that do not cross-react with other hemagglutinin polypeptides are preferred. Particularly preferred antibodies do not cross-react with antibodies produced against hemagglutinin polypeptides derived from H5 serotype influenza viruses. The antibodies of the subject invention can be prepared using standard materials and methods known in the art (see, for example, *Monoclonal Antibodies. Principles and Practice,* 1983*; Monoclonal Hybridoma Antibodies. Techniques and Applications,* 1982*; Selected Methods in Cellular Immunology,* 1980*; Immunological Methods, Vol. II,* 1981*; Practical Immunology*, and Kohler et al. [1975*] Nature* 256:495). These antibodies can further comprise one or more additional components, such as a solid support, a carrier or pharmaceutically acceptable excipient, or a label.

The term "antibody" includes monoclonal antibodies (including full length monoclonal antibodies), polyclonal antibodies, multispecific antibodies (e.g., bispecific antibodies), and antibody fragments so long as they exhibit the desired biological activity, particularly neutralizing activity. "Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multi-specific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. [1975] Nature 256: 495, or may be made by recombinant DNA methods (see, e.g., U.S. Pat. No. 4,816,567). The "monoclonal antibodies" may also be isolated from phage antibody libraries using the techniques described in Clackson et al. [1991] Nature 352: 624-628 and Marks et al. [1991] J. Mol. Biol. 222: 581-597, for example.

The monoclonal antibodies described herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. [1984] Proc. Natl. Acad. Sci. USA 81: 6851-6855). Also included are humanized antibodies that specifically bind to the polypeptides, or fragments thereof, set forth in SEQ ID NO: 2, 4, 6, 8, 10, 12 or 14 (see, for example, U.S. Pat. No. 6,407,213 or 6,417,337, which are hereby incorporated by reference in their entirety, teaching methods of making humanized antibodies).

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies [1994] Vol. 113:269-315, Rosenburg and Moore eds. Springer-Verlag, New York.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). Diabodies are described more fully in, for example, EP 404,097; WO 93/11161; and Hollinger et al. [1993] Proc. Natl. Acad. Sci. USA 90: 6444-6448. The term "linear antibodies" refers to the antibodies described in Zapata et al. [1995] Protein Eng. 8(10):1057-1062.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As discussed above, "nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules).

The range of percent identity, between 20.00% and 99.99%, is to be taken as including, and providing written description and support for, any fractional percentage, in intervals of 0.01%, between 20.00% and, up to, including 99.99%. These percentages are purely statistical and differences between two nucleic acid sequences can be distributed randomly and over the entire sequence length. For example, homologous sequences can exhibit a percent identity of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of the instant invention. Typically, the percent identity is calculated with reference to the full length, native, and/or naturally occurring polynucleotide. The terms "identical" or percent "identity", in the context of two or more polynucleotide or polypeptide sequences, refer to two or more sequences or subsequences that are the same or have a specified percentage of nucleotides or amino acid residues that are the same, when compared and aligned for maximum correspondence over a comparison window, as measured using a sequence comparison algorithm or by manual alignment and visual inspection.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3): 403-410; Thompson et al., 1994, Nucleic Acids Res. 22(2): 4673-4680; Higgins et al., 1996, Methods Enzymol. 266:383-402; Altschul et al., 1990, J. Mol. Biol. 215(3):403-410; Altschul et al., 1993, Nature Genetics 3:266-272). Sequence comparisons are, typically, conducted using default parameters provided by the vendor or using those parameters set forth in the above-identified references, which are hereby incorporated by reference in their entireties.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence".

Sequence homology and sequence identity can also be determined by hybridization studies under high stringency, intermediate stringency, and/or low stringency. Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak [1987] *DNA Probes*, Stockton Press, New York, N.Y., pp. 169-170.

For example, hybridization of immobilized DNA on Southern blots with $^{32}$P-labeled gene-specific probes can be performed by standard methods (Maniatis et al. [1982] *Molecular Cloning. A Laboratory Manual*, Cold Spring Harbor Laboratory, New York). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5×Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$Tm$=81.5° C.+16.6 Log [Na$^+$]+0.41 (% $G$+$C$)−0.61 (% formamide)−600/length of duplex in base pairs.

Washes are typically carried out as follows:

(1) twice at room temperature for 15 minutes in 1×SSPE, 0.1% SDS (low stringency wash);

(2) once at $T_m$ −20° C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$T_m$(° C.)=2(number T/A base pairs)+4(number G/C base pairs) (Suggs et al. [1981] *ICN-UCLA Symp. Dev. Biol. Using Purified Genes*, D. D. Brown [ed.], Academic Press, New York, 23:683-693).

Washes can be carried out as follows:

(1) twice at room temperature for 15 minutes 1×SSPE, 0.1% SDS (low stringency wash);

2) once at the hybridization temperature for 15 minutes in 1×SSPE, 0.1% SDS (intermediate stringency wash).

In general, salt and/or temperature can be altered to change stringency. With a labeled DNA fragment >70 or so bases in length, the following conditions can be used:

| Low: | 1 or 2X SSPE, room temperature |
| Low: | 1 or 2X SSPE, 42° C. |

-continued

| Intermediate: | 0.2X or 1X SSPE, 65° C. |
| High: | 0.1X SSPE, 65° C.. |

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5-20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning. A Laboratory Manual*, Cold Spring Harbor Laboratory, New York; Wei et al. [1983] *J. Biol. Chem.* 258:13006-13512.

The present invention further comprises fragments of the polynucleotide sequences of the instant invention. Representative fragments of the polynucleotide sequences according to the invention will be understood to mean any nucleotide fragment having at least 5 successive nucleotides, preferably at least 12 successive nucleotides, and still more preferably at least 15, 18, or at least 20 successive nucleotides of the sequence from which it is derived. The upper limit for such fragments is the total number of nucleotides found in the full-length sequence encoding a particular polypeptide (e.g. a polypeptide such as that of SEQ ID NO: 2). The term "successive" can be interchanged with the term "consecutive" or the phrase "contiguous span". Thus, in some embodiments, a polynucleotide fragment may be referred to as "a contiguous span of at least X nucleotides, wherein X is any integer value beginning with 5; the upper limit for such fragments is one nucleotide less than the total number of nucleotides found in the full-length sequence encoding a particular polypeptide (e.g., a polypeptide comprising SEQ ID NO: 2).

In some embodiments, the subject invention includes those fragments capable of hybridizing under various conditions of stringency conditions (e.g., high or intermediate or low stringency) with a nucleotide sequence according to the invention; fragments that hybridize with a nucleotide sequence of the subject invention can be, optionally, labeled as set forth below.

The subject invention provides, in one embodiment, methods for the identification of the presence of nucleic acids according to the subject invention in transformed host cells or in cells isolated from an individual suspected of being infected by avian influenza. In these varied embodiments, the invention provides for the detection of nucleic acids in a sample (obtained from the individual or from a cell culture) comprising contacting a sample with a nucleic acid (polynucleotide) of the subject invention (such as an RNA, mRNA, DNA, cDNA, or other nucleic acid). In a preferred embodiment, the polynucleotide is a probe that is, optionally, labeled and used in the detection system. Many methods for detection of nucleic acids exist and any suitable method for detection is encompassed by the instant invention. Typical assay formats utilizing nucleic acid hybridization includes, and are not limited to, 1) nuclear run-on assay, 2) slot blot assay, 3) northern blot assay (Alwine, et al., *Proc. Natl. Acad. Sci.* 74:5350), 4) magnetic particle separation, 5) nucleic acid or DNA chips, 6) reverse Northern blot assay, 7) dot blot assay, 8) in situ hybridization, 9) RNase protection assay (Melton, et al., *Nuc. Acids Res.* 12:7035 and as described in the 1998 catalog of Ambion, Inc., Austin, Tex.), 10) ligase chain reaction, 11) polymerase chain reaction (PCR), 12) reverse transcriptase (RT)-PCR (Berchtold, et al., *Nuc. Acids. Res.* 17:453), 13) differential display RT-PCR (DDRT-PCR) or other suitable combinations of techniques and assays. Labels suitable for use in these detection methodologies include, and are not limited to 1) radioactive labels, 2) enzyme labels, 3) chemiluminescent labels, 4) fluorescent labels, 5) magnetic labels, or other suitable labels, including those set forth below. These methodologies and labels are well known in the art and widely available to the skilled artisan. Likewise, methods of incorporating labels into the nucleic acids are also well known to the skilled artisan.

Thus, the subject invention also provides detection probes (e.g., fragments of the disclosed polynucleotide sequences) for hybridization with a target sequence or the amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}$P, $^{35}$S, $^{3}$H, $^{125}$I) or with a molecule such as biotin, acetylaminofluorene, digoxigenin, 5-bromo-deoxyuridine, or fluorescein to provide probes that can be used in numerous applications.

Polynucleotides of the subject invention can also be used for the qualitative and quantitative analysis of gene expression using arrays or polynucleotides that are attached to a solid support. As used herein, the term array means a one-, two-, or multi-dimensional arrangement of full length polynucleotides or polynucleotides of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full-length polynucleotides of the subject invention, or fragments thereof, in a complementary DNA microarray as described by Schena et al. (*Science* 270:467-470, 1995; *Proc. Natl. Acad. Sci. U.S.A.* 93:10614-10619, 1996). Polynucleotides, or fragments thereof, are amplified by PCR and arrayed onto silylated microscope slides. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

mRNA is isolated from a biological sample and probes are prepared by a single round of reverse transcription. Probes are hybridized to 1 cm$^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the polynucleotides present in a biological sample can also be performed in complementary DNA arrays as described by Pietu et al. (Genome Research 6:492-503, 1996). The polynucleotides of the invention, or fragments thereof, are PCR amplified and spotted on membranes. Then, mRNAs originating from biological samples derived from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, the polynucleotide sequences of to the invention may also be used in analytical systems, such as DNA chips. DNA chips and their uses are well known in the art and (see for example, U.S. Pat. Nos. 5,561,071; 5,753,439; 6,214,545; Schena et al., *BioEssays*, 1996, 18:427-431; Bianchi et al., *Clin. Diagn. Virol.*, 1997, 8:199-208; each of which is hereby incorporated by reference in their entireties) and/or are provided by commercial vendors such as Affymetrix, Inc.

(Santa Clara, Calif.). In addition, the nucleic acid sequences of the subject invention can be used as molecular weight markers in nucleic acid analysis procedures.

The subject invention also provides genetic constructs comprising: a) a polynucleotide sequence encoding a polypeptide comprising SEQ ID No: 2, 4, 6, 8, 10, 12 or 14, or a fragment thereof, b) a polynucleotide sequence having at least about 20% to 99.99% identity to a polynucleotide sequence encoding a polypeptide comprising SEQ ID No: 2, 4, 6, 8, 10, 12 or 14, or a fragment of SEQ ID NO: 2, 4, 6, 8, 10, 12 or 14, wherein said polypeptide has at least one of the biological activities of a polypeptide comprising SEQ ID No: 2, 4, 6, 8, 10, 12 or 14, or a fragment thereof, c) a polynucleotide sequence encoding a polypeptide having at least about 20% to 99.99% identity to a polypeptide comprising SEQ ID No: 2, 4, 6, 8, 10, 12 or 14, or a fragment of SEQ ID NO: 2, 4, 6, 8, 10, 12 or 14, wherein said polypeptide has at least one of the biological activities of a polypeptide comprising SEQ ID No: 2, 4, 6, 8, 10, 12 or 14, or a fragment thereof; d) a polynucleotide sequence encoding a fragment of a polypeptide comprising SEQ ID No: 2, 4, 6, 8, 10, 12 or 14, wherein said fragment has at least one of the activities of the polypeptide of SEQ ID No: 2, 4, 6, 8, 10, 12 or 14; e) a polynucleotide sequence comprising SEQ ID NO: 1, 3, 5, 7, 9, 11 or 13; f) a polynucleotide sequence having at least about 20% to 99.99% identity to the polynucleotide sequence of SEQ ID NO: 1, 3, 5, 7, 9, 11 or 13; g) a polynucleotide sequence encoding variant (e.g., a variant polypeptide) of the polypeptides of SEQ ID Nos: 2, 4, 6, 8, 10, 12 or 14, wherein said variant has at least one of the biological activities associated with the polypeptide of SEQ ID NO: 2, 4, 6, 8, 10, 12 or 14; h) a polynucleotide sequence encoding a fragment of a variant polypeptide as set forth in (g), wherein the fragment of said variant polypeptide has at least one of the biological activities associated with the polypeptide; i) a polynucleotide sequence encoding multimeric construct; or j) a polynucleotide that is complementary to the polynucleotides set forth in (a), (b), (c), (d), (e), (f), (g), (h), or (i). Genetic constructs of the subject invention can also contain additional regulatory elements such as promoters and enhancers and, optionally, selectable markers.

Also within the scope of the subject instant invention are vectors or expression cassettes containing genetic constructs as set forth herein or polynucleotides encoding the polypeptides, set forth supra, operably linked to regulatory elements. The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette(s) may additionally contain selectable marker genes operably linked to control elements.

The expression cassette will include in the 5'-3' direction of transcription, a transcriptional and translational initiation region, a DNA sequence of the invention, and a transcriptional and translational termination regions. The transcriptional initiation region, the promoter, may be native or analogous, or foreign or heterologous, to the host cell. Additionally, the promoter may be the natural sequence or alternatively a synthetic sequence. By "foreign" is intended that the transcriptional initiation region is not found in the native plant into which the transcriptional initiation region is introduced.

As used herein, a chimeric gene comprises a coding sequence operably linked to a transcriptional initiation region that is heterologous to the coding sequence.

Another aspect of the invention provides vectors for the cloning and/or the expression of a polynucleotide sequence taught herein. Vectors of this invention, including vaccine vectors, can also comprise elements necessary to allow the expression and/or the secretion of the said nucleotide sequences in a given host cell. The vector can contain a promoter, signals for initiation and for termination of translation, as well as appropriate regions for regulation of transcription. In certain embodiments, the vectors can be stably maintained in the host cell and can, optionally, contain signal sequences directing the secretion of translated protein. These different elements are chosen according to the host cell used. Vectors can integrate into the host genome or, optionally, be autonomously-replicating vectors.

The subject invention also provides for the expression of a polypeptide, peptide, fragment, or variant encoded by a polynucleotide sequence disclosed herein comprising the culture of a host cell transformed with a polynucleotide of the subject invention under conditions that allow for the expression of the polypeptide and, optionally, recovering the expressed polypeptide.

The disclosed polynucleotide sequences can also be regulated by a second nucleic acid sequence so that the protein or peptide is expressed in a host transformed with the recombinant DNA molecule. For example, expression of a protein or peptide may be controlled by any promoter/enhancer element known in the art. Promoters which may be used to control expression include, but are not limited to, the CMV-IE promoter, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes simplex thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic vectors containing promoters such as the β-lactamase promoter (Villa-Kamaroff, et al., 1978, Proc. Natl. Acad. Sci. U.S.A. 75:3727-3731), or the tac promoter (De-Boer, et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., 1983, Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

The vectors according to the invention are, for example, vectors of plasmid or viral origin. In a specific embodiment, a vector is used that comprises a promoter operably linked to a protein or peptide-encoding nucleic acid sequence contained within the disclosed polynucleotide sequences, one or more origins of replication, and, optionally, one or more selectable markers (e.g., an antibiotic resistance gene). Expression vectors comprise regulatory sequences that control gene expression, including gene expression in a desired host cell. Exemplary vectors for the expression of the polypeptides of the invention include the pET-type plasmid vectors (Promega) or pBAD plasmid vectors (Invitrogen) or those provided in the examples below. Furthermore, the vectors according to the invention are useful for transforming host cells so as to clone or express the polynucleotide sequences of the invention.

The invention also encompasses the host cells transformed by a vector according to the invention. These cells may be obtained by introducing into host cells a nucleotide sequence inserted into a vector as defined above, and then culturing the said cells under conditions allowing the replication and/or the expression of the polynucleotide sequences of the subject invention.

The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells, and/or insect cells using baculovirus vectors. In some embodiments, the host cells for expression of the polypeptides include, and are not limited to, those taught in U.S. Pat. Nos. 6,319,691, 6,277,375, 5,643,570, or 5,565,335, each of which is incorporated by reference in its entirety, including all references cited within each respective patent.

Furthermore, a host cell strain may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

Also provided are transformed plant cells, transgenic seeds, transgenic plant parts and transgenic plants which contain one or more polynucleotide sequence, genetic construct, vector, or expression cassette comprising one or more of the polynucleotides disclosed herein, or biologically active fragments thereof, operably linked to control elements. As used herein, the term "plant" includes algae and higher plants (including, but not limited to trees). Thus, algae, monocots, and dicots may be transformed with genetic constructs of the invention, expression cassettes, or vectors according to the invention. In certain preferred embodiments, tobacco plants or tobacco cell lines are transformed with genetic constructs according to the subject invention.

Thus, polypeptides useful in the production of the compositions or immunization protocols discussed in this application can be derived or obtained from a transgenic plant cell that has been genetically engineered to express a polypeptide comprising (consisting essentially of or consisting of) SEQ ID NO: 2, 4, 6, 8, 10, 12 or 14, fragments thereof, variant polypeptides thereof, or fragments of the aforementioned polypeptides. See, for example, U.S. Patent Pub. No: 2004/0268442 A1, the disclosure of which is hereby incorporated by reference in its entirety.

Transgenic plant is herein defined as a plant cell culture, plant cell line, plant tissue culture, lower plant, monocot plant, dicot plant, or progeny or part thereof derived from a transformed plant cell or protoplast, wherein the genome of the transformed plant contains foreign DNA, introduced by laboratory techniques, not originally present in a native, non-transgenic plant cell of the same species. The terms "transgenic plant" and "transformed plant" have sometimes been used in the art as synonymous terms to define a plant whose DNA contains an exogenous DNA molecule. Where appropriate, the polynucleotides encoding the polypeptides set forth herein can be optimized for expression in the transformed plants, plant cells or plant parts. That is, the genes can be synthesized using species-preferred codons corresponding to the species of interest. Methods are available in the art for synthesizing for example, plant-preferred genes. See, for example, U.S. Pat. Nos. 5,380,831 and 5,436,391, and Murray et al. (1989) Nucleic Acids Res. 17:477-498, herein incorporated by reference.

Construction of gene cassettes for expressing polypeptides in plants is readily accomplished utilizing well known methods, such as those disclosed in Sambrook et al. (1989); and Ausubel et al., (1987) Current Protocols in Molecular Biology, John Wiley and Sons, New York, N.Y.

In preparing the constructs of this invention, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

In carrying out the various steps, cloning is employed, so as to amplify a vector containing the promoter/gene of interest for subsequent introduction into the desired host cells. A wide variety of cloning vectors are available, where the cloning vector includes a replication system functional in *E. coli* and a marker which allows for selection of the transformed cells. Illustrative vectors include pBR322, pUC series, pACYC184, Bluescript series (Stratagene) etc. Thus, the sequence may be inserted into the vector at an appropriate restriction site(s), the resulting plasmid used to transform the *E. coli* host (e.g., *E. coli* strains HB101, JM101 and DH5α), the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Vectors are available or can be readily prepared for transformation of plant cells. In general, plasmid or viral vectors should contain all the DNA control sequences necessary for both maintenance and expression of a heterologous DNA sequence in a given host. Such control sequences generally include a leader sequence and a DNA sequence coding for translation start-signal codon, a translation terminator codon, and a DNA sequence coding for a 3' UTR signal controlling messenger RNA processing. Selection of appropriate elements to optimize expression in any particular species is a matter of ordinary skill in the art utilizing the teachings of this disclosure. Finally, the vectors should desirably have a marker gene that is capable of providing a phenotypical property which allows for identification of host cells containing the vector.

The activity of the foreign coding sequence inserted into plant cells is dependent upon the influence of endogenous plant DNA adjacent the insert. Generally, the insertion of heterologous genes appears to be random using any transformation technique; however, technology exists for producing plants with site specific recombination of DNA into plant cells (see WO 91/09957). Any method or combination of methods resulting in the expression of the desired sequence or sequences under the control of the promoter is acceptable.

The present invention is not limited to any particular method for transforming plant cells. Technology for introducing DNA into plant cells is well-known to those of skill in the art. Four basic methods for delivering foreign DNA into plant cells have been described. Chemical methods (Graham and van der Eb, *Virology*, 54(02):536-539, 1973; Zatloukal, Wagner, Cotten, Phillips, Plank, Steinlein, Curiel, Birnstiel, *Ann. N.Y. Acad. Sci.*, 660:136-153, 1992); Physical methods including microinjection (Capecchi, *Cell*, 1980, 22(2):479-488), electroporation (Wong and Neumann, 1982, *Biochim. Biophys. Res. Commun.*, 107(2):584-587; Fromm, Taylor, Walbot, 1985, *Proc. Natl. Acad. Sci. USA*, 82(17):5824-5828; U.S. Pat. No. 5,384,253) and the gene gun (Johnston and Tang, 1994, *Methods Cell. Biol.*, 43(A):353-365; Fynan, Webster, Fuller, Haynes, Santoro, Robinson, 1993, *Proc. Natl. Acad. Sci. USA*, 90(24):11478-11482); Viral methods (Clapp, 1993, *Clin. Perinatol.*, 20(1):155-168; Lu, Xiao, Clapp, Li, Broxmeyer, 1993, *J. Exp. Med.*, 178(6):2089-2096; Eglitis and Anderson, 1988, *Biotechniques*, 6(7):608-614; Eglitis, Kantoff, Kohn, Karson, Moen, Lothrop, Blaese, Anderson, 1988, *Avd. Exp. Med. Biol.*, 241:19-27); and Receptor-mediated methods (Curiel, Agarwal, Wagner, Cotten, 1991, *Proc. Natl. Acad. Sci. USA*, 88(19):8850-8854; Curiel, Wagner, Cotten, Birnstiel, Agarwal, Li, Loechel, Hu, 1992, *Hum. Gen. Ther.*, 3(2):147-154; Wagner et al., 1992, *Proc. Natl. Acad. Sci. USA*, 89 (13):6099-6103).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material to pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988, *Plant Physiol.*, 87:671-674) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

*Agrobacterium*-mediated transfer is a widely applicable system for introducing foreign DNA into plant cells because the DNA can be introduced into whole plant tissues, eliminating the need to regenerate an intact plant from a protoplast. The use of *Agrobacterium*-mediated plant integrating vectors to introduce DNA into plant cells is well known in the art. See, for example, the methods described in Fraley et al., 1985, *Biotechnology*, 3:629; Rogers et al., 1987, *Meth. in Enzymol.*, 153:253-277. Further, the integration of the Ti-DNA is a relatively precise process resulting in few rearrangements. The region of DNA to be transferred is defined by the border sequences, and intervening DNA is usually inserted into the plant genome as described in Spielmann et al., 1986, *Mol. Gen. Genet.*, 205:34; Jorgensen et al., 1987, *Mol. Gen. Genet.*, 207:471.

Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate construction of vectors capable of expressing various proteins or polypeptides. Convenient multi-linker regions flanked by a promoter and a polyadenylation site for direct expression of inserted polypeptide coding genes are suitable for present purposes. In addition, *Agrobacterium* containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Potrykus et al., 1985, *Mol. Gen. Genet.*, 199:183; Marcotte et al., 1988, *Nature*, 335:454). Application of these systems to different plant species depends on the ability to regenerate the particular species from protoplasts.

Once the plant cells have been transformed, selected and checked for antigen expression, it is possible in some cases to regenerate whole fertile plants. This will greatly depend on the plant species chosen. Methods for regenerating numerous plant species have been reported in the literature and are well known to the skilled artisan. For practice of the present invention, it is preferable to transform plant cell lines that can be cultured and scaled-up rapidly by avoiding the generally lengthy regeneration step. In addition, the use of plant cell cultures avoids open field production and greatly reduces the chances of gene escape and food contamination. Tobacco suspension cell cultures such NT-1 and BY-2 (An, G., 1985, *Plant Physiol.*, 79:568-570) are preferred because these lines are particularly susceptible to handling in culture, are readily transformed, produce stably integrated events and are amenable to cryopreservation.

The tobacco suspension cell line, NT-1, is suitable for the practice of the present invention. NT-1 cells were originally developed from *Nicotiana tabacum* L.cv. bright yellow 2. The NT-1 cell line is widely used and readily available; though, any tobacco suspension cell line is consistent with the practice of the invention. NT-1 cells suitable for use in the examples below are available from the American Type Culture Collection under accession number ATCC No. 74840.

See also U.S. Pat. No. 6,140,075, herein incorporated by reference in its entirety.

Many plant cell culture techniques and systems ranging from laboratory-scale shaker flasks to multi-thousand liter bioreactor vessels have been described and are well know in the art of plant cell culture. See for example Fischer, R. et al, 1999, *Biotechnol. Appl. Biochem.*, 30, 109-112 and Doran, P., 2000, *Current Opinions in Biotechnology*, 11:199-204. After the transformed plant cells have been cultured to the mass desired, they are harvested, gently washed and placed in a suitable buffer for disruption. Many different buffers are compatible with the present invention. In general the buffer is an aqueous isotonic buffered salt solution at or near a neutral pH value that does not contain harsh detergents that can be used to solubilize membranes. Preferred buffers include Dulbecco's Phosphate Buffered Saline and PBS containing 1 mM EDTA.

In one embodiment, cells can be disrupted by sonication. The washed cells are placed in buffer in a range of about 0.01 gm/ml to about 5.0 gm/ml, preferably in a range of about 0.1 gm/ml to about 0.5 gm/ml (washed wet weight cells per volume of buffer). Many commercially available sonication instruments are consistent with the invention and sonication times range from about 5 to about 20 seconds, preferably about 15 to about 20 seconds. The resulting may range in size from a few microns to several hundred microns and expose the HA1 polypeptide or immunogenic fragments thereof.

The subject invention also concerns DNA vaccine compositions that can be employed to elicit an immune response or a protective immune response. In this aspect of the invention, an amount of a composition comprising recombinant DNA or mRNA encoding a polypeptide as provided herein (or a fragment thereof) is administered to an individual in an amount sufficient to elicit an immune response or protective immune response in said individual. Signal sequences may be deleted from the nucleic acid encoding an antigen of interest and the individual may be monitored for the induction of an immune response according to methods known in the art. A "protective immune response" or "therapeutic immune response" refers to a CTL (or $CD8^+$ T cell), an HTL (or $CD4^+$ T cell), and/or a protective humoral immune response to an antigen that, in some way, prevents or at least partially arrests disease symptoms, side effects or progression. In the context of this invention, such a protective or therapeutic response provides increased survival rates (reduced mortality) in immunized individuals as compared to non-immunized individuals or a reduction in viral shedding in immunized individuals challenged with avian influenza virus.

In another embodiment, the subject invention further comprises the administration of polynucleotide (DNA) vaccines in conjunction with a polypeptide antigen, or composition thereof, of the invention. In a preferred embodiment, the antigen is the polypeptide that is encoded by the polynucleotide administered as the polynucleotide vaccine. As a particularly preferred embodiment, the polypeptide antigen is administered as a booster subsequent to the initial administration of the polynucleotide vaccine.

A further embodiment of the subject invention provides for the induction of an immune response to the novel hemagglutinin antigens disclosed herein (see, for example, the polypeptides and peptide fragments set forth in the Sequence Listing attached hereto) using a "prime-boost" vaccination regimen known to those skilled in the art. In this aspect of the invention, a DNA vaccine or polypeptide antigen of the subject invention is administered to an individual in an amount sufficient to "prime" the immune response of the individual. The immune response of the individual is then "boosted" via the administration of: 1) one or a combination of: a peptide, polypeptide, and/or full length polypeptide antigen of the subject invention (optionally in conjunction with a immunostimulatory molecule and/or an adjuvant); or 2) a viral vector that contains nucleic acid encoding one, or more, of the same or, optionally, different, antigens, multi-epitope constructs, and/or peptide antigens set forth herein. In some alternative embodiments of the invention, a gene encoding an immunostimulatory molecule may be incorporated into the viral vector used to "boost the immune response of the individual. Exemplary immunostimulatory molecules include, and are not limited to, IL-1, IL-2, IL-3, IL-4, IL-5, IL-6, IL-7, IL-8, IL-9, IL-10, IL-11, IL-15, Il-16, Il-18, IL-23, IL-24, erythropoietin, G-CSF, M-CSF, platelet derived growth factor (PDGF), MSF, FLT-3 ligand, EGF, fibroblast growth factor (FGF; e.g., aFGF (FGF-1), bFGF (FGF-2), FGF-3, FGF-4, FGF-5, FGF-6, or FGF-7), insulin-like growth factors (e.g., IGF-1, IGF-2); vascular endothelial growth factor (VEGF); interferons (e.g., IFN-γ, IFN-α, IFN-β); leukemia inhibitory factor (LIF); ciliary neurotrophic factor (CNTF); oncostatin M; stem cell factor (SCF); transforming growth factors (e.g., TGF-α, TGF-β1, TGF-β1, TGF-β1), or chemokines (such as, but not limited to, BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1, ABCD-1, MIP-1α, MIP-1β, MIP-2α/GROβ, MIP-3α/Exodus/LARC, MIP-3β/Exodus-3/ELC, MIP-4/PARC/DC-CK1, PF-4, RANTES, SDF1α, TARC, or TECK). Genes encoding these immunostimulatory molecules are known to those skilled in the art and coding sequences may be obtained from a variety of sources, including various patents databases, publicly available databases (such as the nucleic acid and protein databases found at the National Library of Medicine or the European Molecular Biology Laboratory), the scientific literature, or scientific literature cited in catalogs produced by companies such as Genzyme, Inc., R&D Systems, Inc, or InvivoGen, Inc. [see, for example, the 1995 Cytokine Research Products catalog, Genzyme Diagnostics, Genzyme Corporation, Cambridge Mass.; 2002 or 1995 Catalog of R&D Systems, Inc (Minneapolis, Minn.); or 2002 Catalog of InvivoGen, Inc (San Diego, Calif.) each of which is incorporated by reference in its entirety, including all references cited therein].

Methods of introducing DNA vaccines into individuals are well-known to the skilled artisan. For example, DNA can be injected into skeletal muscle or other somatic tissues (e.g., intramuscular injection). Cationic liposomes or biolistic devices, such as a gene gun, can be used to deliver DNA vaccines. Alternatively, iontophoresis and other means for transdermal transmission can be used for the introduction of DNA vaccines into an individual.

Viral vectors for use in the subject invention can have a portion of the viral genome is deleted to introduce new genes without destroying infectivity of the virus. The viral vector of the present invention is, typically, a non-pathogenic virus. At the option of the practitioner, the viral vector can be selected so as to infect a specific cell type, such as professional antigen presenting cells (e.g., macrophage or dendritic cells). Alternatively, a viral vector can be selected that is able to infect any cell in the individual. Exemplary viral vectors suitable for use in the present invention include, but are not limited to poxvirus such as vaccinia virus, avipox virus, fowlpox virus, a highly attenuated vaccinia virus (such as Ankara or MVA

[Modified Vaccinia Ankara]), retrovirus, adenovirus, baculovirus and the like. In a preferred embodiment, the viral vector is Ankara or MVA.

General strategies for construction of vaccinia virus expression vectors are known in the art (see, for example, Smith and Moss Bio Techniques November/December, 306-312, 1984; U.S. Pat. No. 4,738,846 (hereby incorporated by reference in its entirety). Sutter and Moss (Proc. Nat'l. Acad. Sci. U.S.A. 89:10847-10851, 1992) and Sutter et al. (Vaccine, 12(11):1032-40, 1994) disclose the construction and use as a vector, a non-replicating recombinant Ankara virus (MVA) which can be used as a viral vector in the present invention.

Compositions comprising the subject polynucleotides can include appropriate nucleic acid vaccine vectors (plasmids), which are commercially available (e.g., Vical, San Diego, Calif.) or other nucleic acid vectors (plasmids), which are also commercially available (e.g., Valenti, Burlingame, Calif.). Alternatively, compositions comprising viral vectors and polynucleotides according to the subject invention are provided by the subject invention. In addition, the compositions can include a pharmaceutically acceptable carrier, e.g., saline. The pharmaceutically acceptable carriers are well known in the art and also are commercially available. For example, such acceptable carriers are described in E. W. Martin's *Remington's Pharmaceutical Science*, Mack Publishing Company, Easton, Pa.

Example 1

Vector Constructions

Throughout these examples, the following designations may be used to refer to the sequences identified as SEQ ID NOs: 1, 3, 5, 7, 9, 11 or 13:

SEQUENCE ID NO: 1: HA5TW68 v3: Avian Influenza virus (AIV) Hemagglutinin (HA) H5 Turkey/Wisconsin/68; no cleavage site; plant codon optimized; SEQUENCE ID NO: 3: HA5TW68 v4: Avian Influenza virus (AIV) HA H5 Turkey/Wisconsin/68; no cleavage site with serine 239 changed to asparagine; plant codon optimized; SEQUENCE ID NO: 5: HA5TW68 v5: Avian Influenza virus (AIV) HA H5 Turkey/Wisconsin/68 native sequence; plant codon optimized including protease cleavage site;

SEQUENCE ID NO: 7: HA5AH v1: Avian Influenza virus (AIV) HA H5 902755 ancestral consensus hybrid with amino acid modifications at positions 99, 102 and 170; no cleavage site plant codon optimized; SEQUENCE ID NO: 9: HA5AH v2: Avian Influenza virus (AIV) HA H5 902755 ancestral consensus hybrid with amino acid modifications at positions 99, 102 and 239; no cleavage site; plant codon optimized; and SEQUENCE ID NO: 11: HA5AH v3: Avian Influenza virus (AIV) HA H5 902755 ancestral consensus hybrid with amino acid modifications at positions 99, 102, 170 and 239; no cleavage site; plant codon optimized.

The following HA gene/vector constructs, containing SEQ ID NOs: 1, 3, 5, 7, 9, and 11, are also discussed within these examples:

| | |
|---|---|
| pDAB4492 v1 Ubi10-PAT:CsVMV-HA5tw68 v3 | (vector contains SEQ ID NO: 1); |
| pDAB4493 v1 Ubi10-PAT:dMas-HA5tw68 v3 | (vector contains SEQ ID NO: 1); |
| pDAB4494 v2 Ubi10-PAT:dMas-HA5tw68 v4 | (vector contains SEQ ID NO: 3); |
| pDAB4495 v3 Ubi10-PAT:dMas-HA5tw68 v5 | (vector contains SEQ ID NO: 5); |
| pDAB4496 v4 Ubi10-PAT:dMas-HA5AH v1 | (vector contains SEQ ID NO: 7); |
| pDAB4497 v5 Ubi10-PAT:dMas-HA5AH v2 and | (vector contains SEQ ID NO: 9); |
| pDAB4498 v6 Ubi10-PAT:dMas-HA5AH v3 | (vector contains SEQ ID NO: 11). |

For the purposes of these examples, CSVMV is used to designate the Cassava vein mosaic virus promoter disclosed in U.S. Pat. No. 7,053,205 (which is hereby incorporated by reference in its entirety); PAT is used to designate the phosphinothricin aceyltransferase selectable marker as disclosed in U.S. Pat. Nos. 5,633,434; 5,879,903; 5,637,489; 5,276,268; 5,273,894 (each of which is hereby incorporated by reference in its entirety), dMas designates a chimeric constitutive promoter, 4OCSΔMAS disclosed in U.S. Pat. Nos. 5,001,060; 5,573,932 and 5,290,924 (each of which is hereby incorporated by reference in their entirety).

The following also provides a summary of the gene/amino acid modifications within each respective construct:

| Construct and gene | 99 | 102 | 170 | 239 | 343 |
|---|---|---|---|---|---|
| pDAB4492 v1 HA5tw68 v3 | D | T | SNA | S | — |
| pDAB4493 v1 HA5tw68 v3 | D | T | SNA | S | — |
| pDAB4494 v2 HA5tw68 v4 | D | T | SNA | N | — |
| pDAB4495 v3 HA5tw68 v5 | D | T | SNA | S | RQKR |
| pDAB4496 v4 HA5AH v1 | A | V | NST | S | — |
| pDAB4497 v5 HA5AH v2 | A | V | SNA | N | — |
| pDAB4498 v6 HA5AH v3 | A | V | NST | N | — |

Construction of pDAB4492

A plasmid, DASPICO69, containing the plant codon optimized sequence of HA5tw68 v3 (SEQ ID NO: 1; Hemagglutinin H5 Turkey Wisconsin 68 version #3) was received from PicoScript, 8080 North Stadium, Suite 2100, Houston, Tex. 77054. The HA5tw68 v3 DNA coding sequence was isolated from DASPICO69 via a BbsI and SacI restriction enzyme digestion, and cloned into the corresponding NcoI and SacI restriction sites of pDAB3912. The resulting construct, pDAB4485, contained the CsVMV promoter v2 (Cassava vein mosaic virus promoter version #2)—HA5tw68 v3 coding sequence—Atu ORF23 3'UTR v1 (*Agrobacterium tumefaciens* Open Reading Frame 23 3'Untranslated Region version #1) flanked by the Gateway attL recombination sites (The Gateway cloning system and att sites are from Invitrogen Corporation, Carlsbad Calif.). pDAB4485 was confirmed via restriction enzyme digestion.

The CsVMV promoter v2—HA5tw68 v3—Atu ORF23 3'UTR v1 cassette was mobilized into the attR Gateway recombination Sites of the destination binary vector pDAB3736 via the Gateway Clonase enzyme reaction (Cat #11791-019, Invitrogen Corporation, Carlsbad Calif.). Positive clones were identified by restriction enzyme digestion and confirmed via sequencing reactions. The completed binary contained the T-DNA border B—RB7 MARv3 (*Arabidopsis thaliana* Matrix Attachment Region version #3)—CsVMV promoter v2—HA5tw68 v3—Atu ORF23 3'UTR v1—At Ubi10 promoter v2 (*Arabidopsis thaliana* polyUbiquitin10 promoter version #2)—PAT v3 (phosphinothricin acetyl transferase version #3)—Atu ORF1 3'UTR v3 (*Agrobacterium tumefaciens* Open Reading Frame 1 3'Untranslated Region version #3)—T-DNA Border A. The resulting vector was labeled pDAB4492.

Construction of pDAB4493

A plasmid, DASPICO69, containing the plant codon optimized sequence of HA5tw68 v3 (Hemagglutinin H5 Turkey Wisconsin 68 version #3) was received from PicoScript, 8080 North Stadium, Suite 2100, Houston, Tex. 77054. The HA5tw68 v3 DNA coding sequence was isolated from DASPICO69 via a BbsI and SacI restriction enzyme digestion, and cloned into the corresponding NcoI and SacI restriction sites of pDAB3914. The resulting construct, pDAB4486, contained the Delta MAS promoter v1 (Delta MAS 4 OCS promoter version #1)—HA5tw68 v3 coding sequence—Atu ORF23 3'UTR v1 (*Agrobacterium tumefaciens* Open Reading Frame 23 3'Untranslated Region version #1) flanked by the Gateway attL recombination sites (The Gateway cloning system and att sites are from Invitrogen Corporation, Carlsbad Calif.). pDAB4486 was confirmed via restriction enzyme digestion.

The Delta Mas promoter v1—HA5tw68 v3—Atu ORF23 3'UTR v1 cassette was mobilized into the attR Gateway recombination Sites of the destination binary vector pDAB3736 via the Gateway Clonase enzyme reaction (Cat #11791-019, Invitrogen Corporation, Carlsbad Calif.). Positive clones were identified by restriction enzyme digestion and confirmed via sequencing reactions. The completed binary contained the T-DNA border B—RB7 MARv3 (*Arabidopsis thaliana* Matrix Attachment Region version #3)—Delta Mas promoter v1—HA5tw68 v3—Atu ORF23 3'UTR v1—At Ubi10 promoter v2 (*Arabidopsis thaliana* polyUbiquitin10 promoter version #2)—PAT v3 (phosphinothricin acetyl transferase version #3)—Atu ORF1 3'UTR v3 (*Agrobacterium tumefaciens* Open Reading Frame 1 3'Untranslated Region version #3)—T-DNA Border A. The resulting vector was labeled pDAB4493.

Construction of pDAB4494

A plasmid, DASPICO70, containing the plant codon optimized sequence of HA5tw68 v4 (SEQ ID NO: 3; Hemagglutinin H5 Turkey Wisconsin 68 version #4) was received from PicoScript, 8080 North Stadium, Suite 2100, Houston, Tex. 77054. The HA5tw68 v4 DNA coding sequence was isolated from DASPICO70 via a BbsI and SacI restriction enzyme digestion, and cloned into the corresponding NcoI and SacI restriction sites of pDAB3914. The resulting construct, pDAB4487, contained the Delta MAS promoter v1 (Delta MAS 4 OCS promoter version #1)—HA5tw68 v4 coding sequence—Atu ORF23 3'UTR v1 (*Agrobacterium tumefaciens* Open Reading Frame 23 3'Untranslated Region version #1) flanked by the Gateway attL recombination sites (The Gateway cloning system and att sites are from Invitrogen Corporation, Carlsbad Calif.). pDAB4487 was confirmed via restriction enzyme digestion.

The Delta Mas promoter v1—HA5tw68 v4—Atu ORF23 3'UTR v1 cassette was mobilized into the attR Gateway recombination Sites of the destination binary vector pDAB3736 via the Gateway Clonase enzyme reaction (Cat #11791-019, Invitrogen Corporation, Carlsbad Calif.). Positive clones were identified by restriction enzyme digestion and confirmed via sequencing reactions. The completed binary contained the T-DNA border B—RB7 MARv3 (*Arabidopsis thaliana* Matrix Attachment Region version #3)—Delta Mas promoter v1—HA5tw68 v4—Atu ORF23 3'UTR v1—At Ubi10 promoter v2 (*Arabidopsis thaliana* polyUbiquitin10 promoter version #2)—PAT v3 (phosphinothricin acetyl transferase version #3)—Atu ORF1 3'UTR v3 (*Agrobacterium tumefaciens* Open Reading Frame 1 3'Untranslated Region version #3)—T-DNA Border A. The resulting vector was labeled pDAB4494.

Construction of pDAB4495

A plasmid, DASPICO71, containing the plant codon optimized sequence of HA5tw68 v5 (SEQ ID NO: 5; Hemagglutinin H5 Turkey Wisconsin 68 version #5) was received from PicoScript, 8080 North Stadium, Suite 2100, Houston, Tex. 77054. The HA5tw68 v5 DNA coding sequence was isolated from DASPICO71 via a BbsI and SacI restriction enzyme digestion, and cloned into the corresponding NcoI and SacI restriction sites of pDAB3914. The resulting construct, pDAB4488, contained the Delta MAS promoter v1 (Delta MAS 4 OCS promoter version #1)—HA5tw68 v5 coding sequence—Atu ORF23 3'UTR v1 (*Agrobacterium tumefaciens* Open Reading Frame 23 3'Untranslated Region version #1) flanked by the Gateway attL recombination sites (The Gateway cloning system and att sites are from Invitrogen Corporation, Carlsbad Calif.). pDAB4488 was confirmed via restriction enzyme digestion.

The Delta Mas promoter v1—HA5tw68 v5—Atu ORF23 3'UTR v1 cassette was mobilized into the attR Gateway recombination Sites of the destination binary vector pDAB3736 via the Gateway Clonase enzyme reaction (Cat #11791-019), Invitrogen Corporation, Carlsbad Calif.). Positive clones were identified by restriction enzyme digestion and confirmed via sequencing reactions. The completed binary contained the T-DNA border B—RB7 MARv3 (*Arabidopsis thaliana* Matrix Attachment Region version #3)—Delta Mas promoter v1—HA5tw68 v5—Atu ORF23 3'UTR v1—At Ubi10 promoter v2 (*Arabidopsis thaliana* polyUbiquitin10 promoter version #2)—PAT v3 (phosphinothricin acetyl transferase version #3)—Atu ORF1 3'UTR v3 (*Agrobacterium tumefaciens* Open Reading Frame 1 3'Untranslated Region version #3)—T-DNA Border A. The resulting vector was labeled pDAB4495.

Construction of pDAB4496

A plasmid, DASDNA1, containing the plant codon optimized sequence of HA5AH v1 (SEQ ID NO: 7; Hemagglutinin H5 Animal Health version #1) was received from DNA2.0, 1430 O'Brien Drive, Suite E, Menlo Park, Calif., 94025. The HA5AH v1 DNA coding sequence was isolated from DASDNA1 via a BbsI and SacI restriction enzyme digestion, and cloned into the corresponding NcoI and SacI restriction sites of pDAB3914. The resulting construct, pDAB4489, contained the Delta MAS promoter v1 (Delta MAS 4 OCS promoter version #1)—HA5AH v1 coding sequence—Atu ORF23 3'UTR v1 (*Agrobacterium tumefaciens* Open Reading Frame 23 3'Untranslated Region version #1) flanked by the Gateway attL recombination sites (The Gateway cloning system and att sites are from Invitrogen Corporation, Carlsbad Calif.). pDAB4489 was confirmed via restriction enzyme digestion.

The Delta Mas promoter v1—HA5AH v1—Atu ORF23 3'UTR v1 cassette was mobilized into the attR Gateway recombination Sites of the destination binary vector pDAB3736 via the Gateway Clonase enzyme reaction (Cat #11791-019, Invitrogen Corporation, Carlsbad Calif.). Positive clones were identified by restriction enzyme digestion and confirmed via sequencing reactions. The completed binary contained the T-DNA border B—RB7 MARv3 (*Arabidopsis thaliana* Matrix Attachment Region version #3)—Delta Mas promoter v1—HA5AH v1—Atu ORF23 3'UTR v1—At Ubi10 promoter v2 (*Arabidopsis thaliana* polyUbiquitin10 promoter version #2)—PAT v3 (phosphinothricin acetyl transferase version #3)—Atu ORF1 3'UTR v3 (*Agrobacterium tumefaciens* Open Reading Frame 1 3'Untranslated Region version #3)—T-DNA Border A. The resulting vector was labeled pDAB4496.

Construction of pDAB4497

Figure 5:
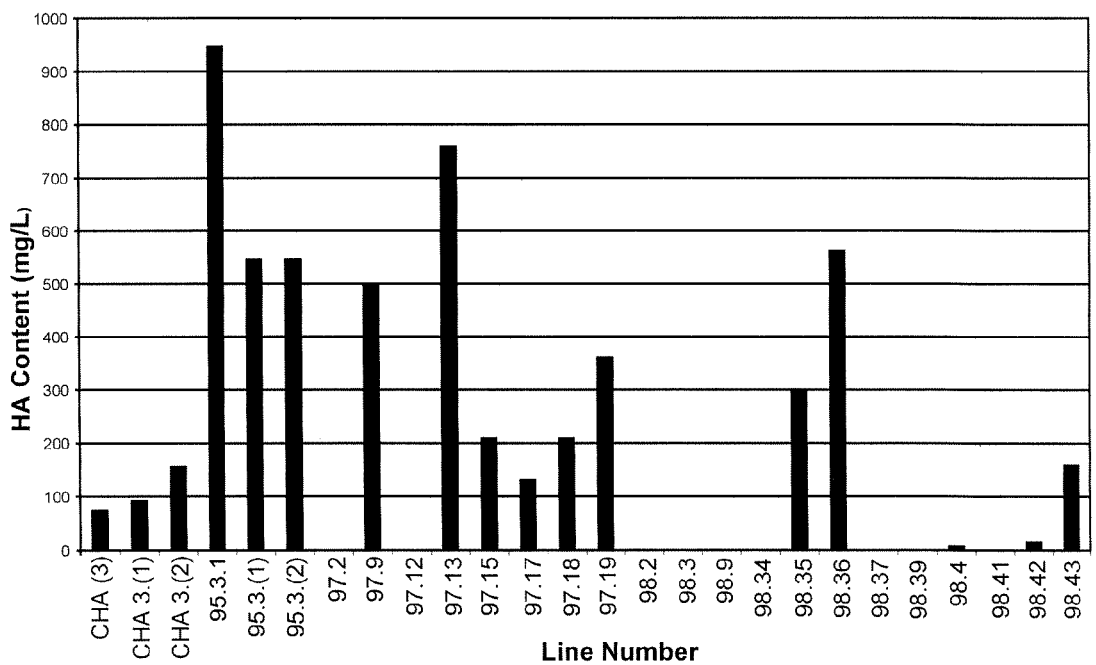
FIG. 5 depicts HA content in cell lines that have stable expression of AIV HA (in NT1 plant cell cultures). The first two digits of the line number indicate the plasmid construct (pDAB44xx).

A plasmid, DASDNA2, containing the plant codon optimized sequence of HA5AH v2 (SEQ ID NO: 9; Hemagglutinin H5 Animal Health version #2) was received from DNA2.0, 1430 O'Brien Drive, Suite E, Menlo Park, Calif., 94025. The HA5AH v2 DNA coding sequence was isolated from DASDNA2 via a BbsI and SacI restriction enzyme digestion, and cloned into the corresponding NcoI and SacI restriction sites of pDAB3914. The resulting construct, pDAB4490, contained the Delta MAS promoter v1 (Delta MAS 4 OCS promoter version #1)—HA5AH v2 coding sequence—Atu ORF23 3'UTR v1 (*Agrobacterium tumefaciens* Open Reading Frame 23 3'Untranslated Region version #1) flanked by the Gateway attL recombination sites (The Gateway cloning system and att sites are from Invitrogen Corporation, Carlsbad Calif.). pDAB4490 was confirmed via restriction enzyme digestion.

The Delta Mas promoter v1—HA5AH v2—Atu ORF23 3'UTR v1 cassette was mobilized into the attR Gateway recombination Sites of the destination binary vector pDAB3736 via the Gateway Clonase enzyme reaction (Cat #11791-019, Invitrogen Corporation, Carlsbad Calif.). Positive clones were identified by restriction enzyme digestion and confirmed via sequencing reactions. The completed binary contained the T-DNA border B—RB7 MARv3 (*Arabidopsis thaliana* Matrix Attachment Region version #3)—Delta Mas promoter v1—HA5AH v2—Atu ORF23 3'UTR v1—At Ubi10 promoter v2 (*Arabidopsis thaliana* polyUbiquitin10 promoter version #2)—PAT v3 (phosphinothricin acetyl transferase version #3)—Atu ORF1 3'UTR v3 (*Agrobacterium tumefaciens* Open Reading Frame 1 3'Untranslated Region version #3)—T-DNA Border A. The resulting vector was labeled pDAB4497.

Construction of pDAB4498

A plasmid, DASDNA3, containing the plant codon optimized sequence of HA5AH v3 (SEQ ID NO: 11; Hemagglutinin H5 Animal Health version #3) was received from DNA2.0, 1430 O'Brien Drive, Suite E, Menlo Park, Calif., 94025. The HA5AH v3 DNA coding sequence was isolated from DASDNA3 via a BbsI and SacI restriction enzyme digestion, and cloned into the corresponding NcoI and SacI restriction sites of pDAB3914. The resulting construct, pDAB4491, contained the Delta MAS promoter v1 (Delta MAS 4 OCS promoter version #1)—HA5AH v3 coding sequence—Atu ORF23 3'UTR v1 (*Agrobacterium tumefaciens* Open Reading Frame 23 3'Untranslated Region version #1) flanked by the Gateway attL recombination sites (The Gateway cloning system and att sites are from Invitrogen Corporation, Carlsbad Calif.). pDAB4491 was confirmed via restriction enzyme digestion.

The Delta Mas promoter v1—HA5AH v3—Atu ORF23 3'UTR v1 cassette was mobilized into the attR Gateway recombination Sites of the destination binary vector pDAB3736 via the Gateway Clonase enzyme reaction (Cat #11791-019, Invitrogen Corporation, Carlsbad Calif.). Positive clones were identified by restriction enzyme digestion and confirmed via sequencing reactions. The completed binary contained the T-DNA border B—RB7 MARv3 (*Arabidopsis thaliana* Matrix Attachment Region version #3)—Delta Mas promoter v1—HA5AH v3—Atu ORF23 3'UTR v1—At Ubi10 promoter v2 (*Arabidopsis thaliana* polyUbiquitin10 promoter version #2)—PAT v3 (phosphinothricin acetyl transferase version #3)—Atu ORF1 3'UTR v3 (*Agrobacterium tumefaciens* Open Reading Frame 1 3'Untranslated Region version #3)—T-DNA Border A. The resulting vector was labeled pDAB4498.

*Agrobacterium* Transformation

Each binary construct was electroporated into *Agrobacterium tumefaciens* strain LBA4404 (1.8V, 25 ΩF, 100Ω).

Tobacco Plant Transient Expression

To see if plants would express the synthetic genes correctly, the binary constructs were transiently transformed into *Nicotiana benthamiana* according to Frederick et al (Frederick, R. D., Thilmony, R. L., Sessa, G. & Martin, G. B. Recognition specificity for the bacterial avirulence protein AvrPto is determined by Thr-204 in the activation loop of the tomato Pto kinase. *Mol Cell* 1998, 2(2), 241-245). Leaf samples were taken 2 and 3 days after inoculation. The expression was then tested through HA-specific ELISA analysis. Ninety-six well ELISA plates were coated with goat anti-HA diluted in 0.01M borate buffer (3.8 $g \cdot l^{-1}$ borax, pH 9, filter sterilized). The plates were incubated overnight at room temperature. Crude protein extracts were made by homogenizing fresh plant materials in 1 $ml \cdot g^{-1}$ of PBS in a Bio 101 Fast prep machine. Insoluble material was removed by centrifugation at 14 000 rpm in an Eppendorf 5415C microcentrifuge at 4° C. for 5 minutes. The resulting sample supernatants are kept on ice during analysis and later stored at −80° C. The plates were washed three times with PBST (PBS Stock+0.05% Tween-20) at 300 μl per well using a plate washer. The plates were then blocked with 5% skim milk in PBST (200 μl per well) for 2 hours at 37° C. and washed three times with PBST at 300 μl per well. The standards and samples were then added to the wells (200 μl per well) and incubated for an hour at 37° C. The plates were washed three times with PBST using 300 μl per well and 100 μl of Chicken anti-AIV per well before incubation at 37° C. for one hour. The plates were then washed three times with PBST before a dilution of the secondary antibody, goat anti-chicken IgG or rabbit anti-goat horseradish peroxidase conjugate (Sigma), was added at 100 μl per well. The plates were incubated for an hour at 37° C., washed three times with PBST then reacted with TMB substrate (Bio Rad, 100 μl per well). The color was allowed to develop for 20-25 minutes before the OD values were read at 450 nm.

As shown in FIG. 4, transient expression of synthetic HA genes was observed (using binary vectors pDAB4492-pDAB4498). The bars represent the average OD of two repetitions of crude extracts made from 7 pooled samples taken 2 or 3 days after inoculation. The ODs of wild type plant leaves were subtracted from the transgenic sample ODs after averaging. "92" represents pDAB4492; "93", pDAB4493; "94", pDAB4494, "95", pDAB4405; "96", pDAB4496; "97", pDAB4497; "98", pDAB4498; "d2", day 2 and "d3", day 3. Thus, the synthetic HA genes were detected by antibodies raised against an avian influenza virus and the synthetic HA genes were also transiently expressed in plants (*N. benthamiana*).

Example 2

Expression in NT1 Cell Lines

Since the synthetic genes were proven expressible by plants, the constructs were used in stable transformation of NT1 cell lines. The plant cell line NT1 is derived from *Nicotiana tobaccum* cells that have reduced alkaloid content and no capacity to regenerate into plants. The plant cell cultures were transformed as described in Cardineau, Guy A.; Mason, Hugh Stanley; Van Eck, Joyce M.; Kirk, Dwayne D.; Walmsley, Amanda Maree. Vectors and cells for preparing immunoprotective compositions, such as Newcastle disease virus HN antigen, from transgenic plants. WO2004098533 (which is hereby incorporated by reference in its entirety) and HA expression determined through the HA-specific ELISA described previously. Table 4 and FIG. 5 illustrate the amounts of HA expressed in the various cell lines.

TABLE 4

Stable expression of AIV HA in NT1 plant cell cultures. The first two digits of the line number indicate the plasmid construct (pDAB44xx)

| Plant Cell Culture Line Number | HA Concentration (mg/L) |
|---|---|
| CHA (3) | 75.43 |
| CHA 3.(1) | 92.57 |
| CHA 3.(2) | 156.86 |
| 95.3.1 | 948.00 |
| 95.3.(1) | 546.86 |
| 95.3.(2) | 546.86 |
| 97.2 | 0 |
| 97.9 | 500.77 |
| 97.12 | 0 |
| 97.13 | 759.23 |
| 97.15 | 210.00 |
| 97.17 | 131.54 |
| 97.18 | 210.00 |
| 97.19 | 362.31 |
| 98.2 | 0 |
| 98.3 | 0 |
| 98.9 | 0 |
| 98.34 | 0 |
| 98.35 | 300.75 |
| 98.36 | 563.25 |
| 98.37 | 0 |
| 98.39 | 0 |
| 98.4 | 8.25 |
| 98.41 | 0 |

Example 3

Petunia Plant Transformation and HA Expression

Figure 6:
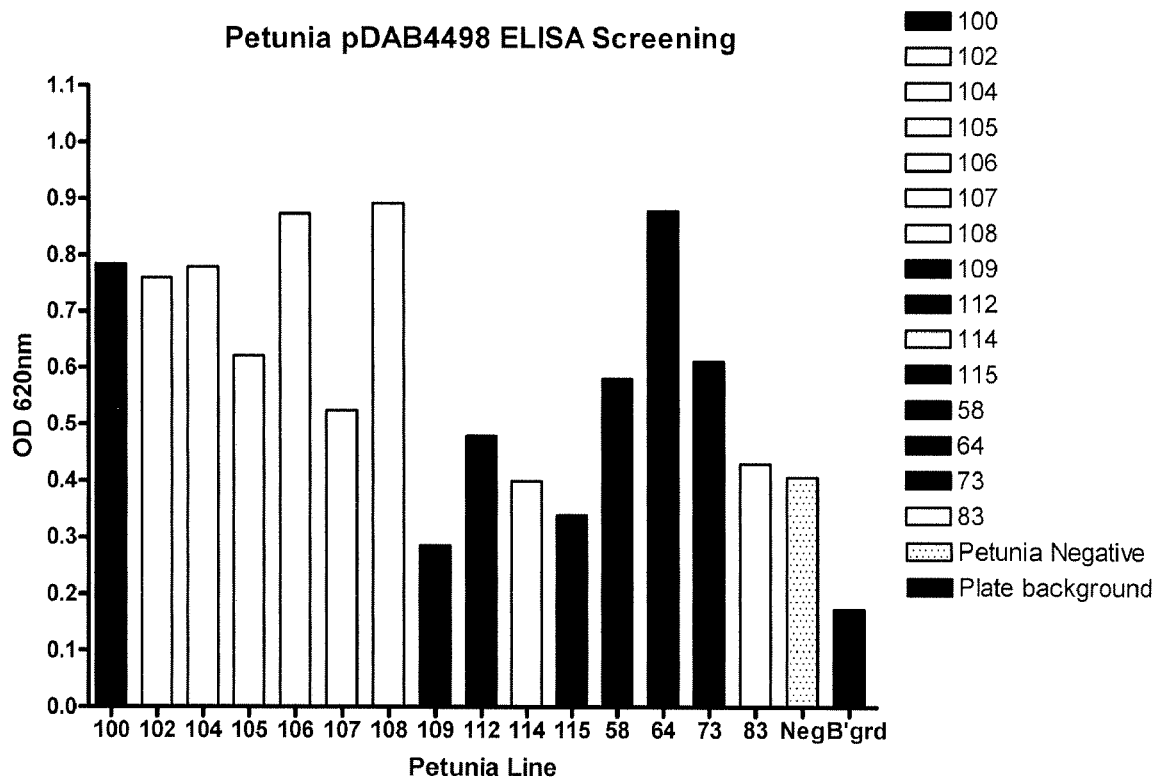
FIG. 6 demonstrates the expression of pDAB4498 in petunia hairy root cultures: 15 lines of petunia, transformed with pDAB4498, along with a petunia negative control were screened for HA expression by ELISA. 50 ug total soluble protein was added to an ELISA plate coated with goat-anti HAv5. HA was detected by the addition of USDA chicken-anti AIV, followed by rabbit-anti chicken then goat-anti rabbit IgG HRP.

Petunia was transformed using the following protocol. 48 hour cultures of *A. rhizogenes* containing the constructs were prepared at 1:5 dilutions in ½ YMB and ½ Murashige and Skoog's basal medium with vitamins (MS media). Diluted cultures were incubated for a further 2 hours at 25° C. Petunia leaf discs were surface sterilised with 0.4% sodium hypochlorite prior to immersion in the *A. rhizogenes* cultures. The infected discs were placed on MS agar plates for 48 hours before being transferred to selection plates. MS agar plates contained MS media, 3% (w/v) sucrose, 1 mgL$^{-1}$ 6-benzylamino-purine (BAP), 1 mgL$^{-1}$ indole-3-acetic acid (IAA), and 0.8% (w/v) agar. Selection plates contained MS media, 3% (w/v) sucrose, 0.8% (w/v) agar and 5 mg/L glufosinate. Newly formed hairy roots, along with a small portion of parent tissue, were transferred to liquid selection MS media containing 500 μgml$^{-1}$ cefotaxime and 5 mg/L glufosinate. After 10 to 14 days of growth, a single root tip was taken from each healthy growing culture and placed into fresh liquid selection MS media. Root cultures were classified as independent lines following this single-root tip sub-culturing. Independent lines were transferred to fresh media every 2 to 3 weeks containing reduced antibiotic concentrations (250 μgml$^{-1}$ cefotaxime) and 5 mg/L glufosinate. As illustrated in FIG. 6, HA recognized by specific antibody could be expressed in petunia Example 4

DNA Vaccine Constructs of Genes pDAB4493-98 and Mouse Vaccination

Figure 7:
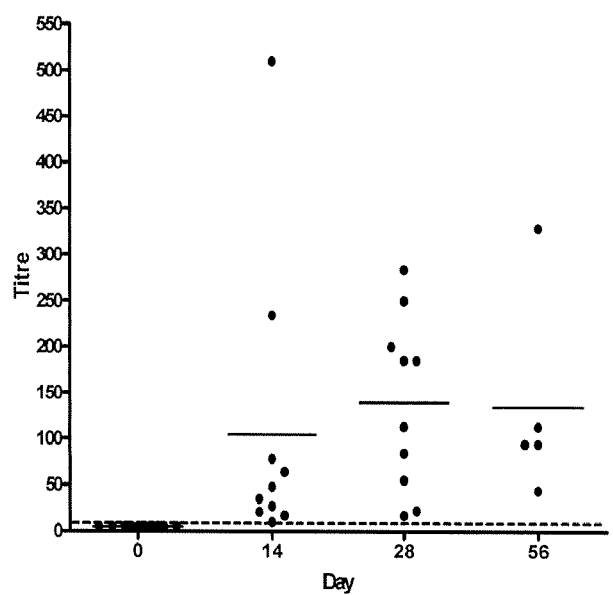
FIG. 7 shows the antibody response to PR-8 HA and was detected by standard ELISA techniques by coating microtiter plates with 5 μg PR-8 HA/well.
Figure 8:
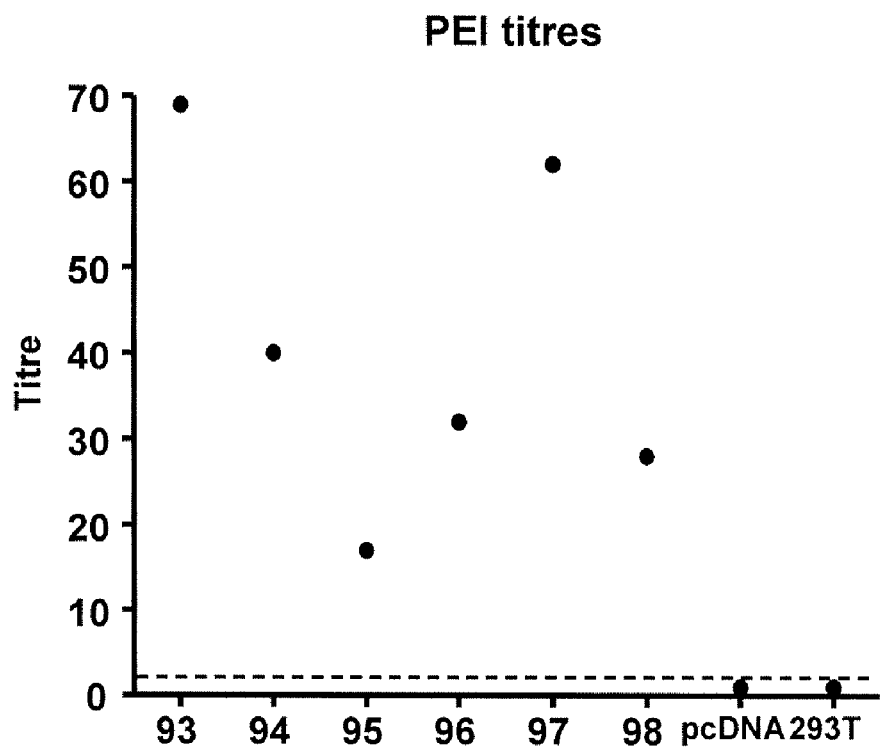
FIG. 8 shows the HA ELISA titers from DNA transfections of animal cells. Results indicate that the ancestor genes 96 (pDAB4496), 97 (pDAB4497) and 98 (pDAB4498) express HA similar to or greater than native Turkey Wisconsin 68 HA genes 93 (pDAB4493), 94 (pDAB4494) and 95 (pDAB4495) or derivatives of the native gene. The harvested transfected cells were added to an ELISA plate coated with goat-anti HAv5. HA was detected by the addition of USDA chicken-anti AIV, followed by rabbit-anti chicken then goat-anti rabbit IgG HRP.
Figure 9A:
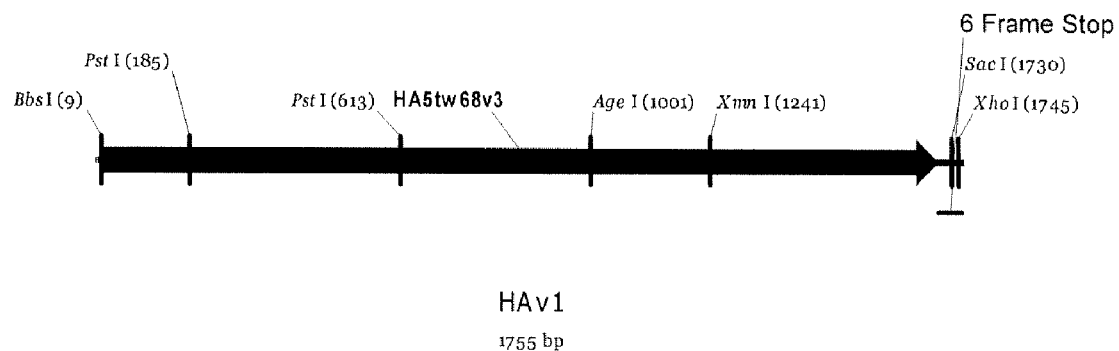
FIGS. 9A (HAv1), 9B (pDAB4492) and 10 (pDAB4493) illustrate various constructs relating to SEQ ID No: 1 (HA5tw68 v3).
Figure 9B:
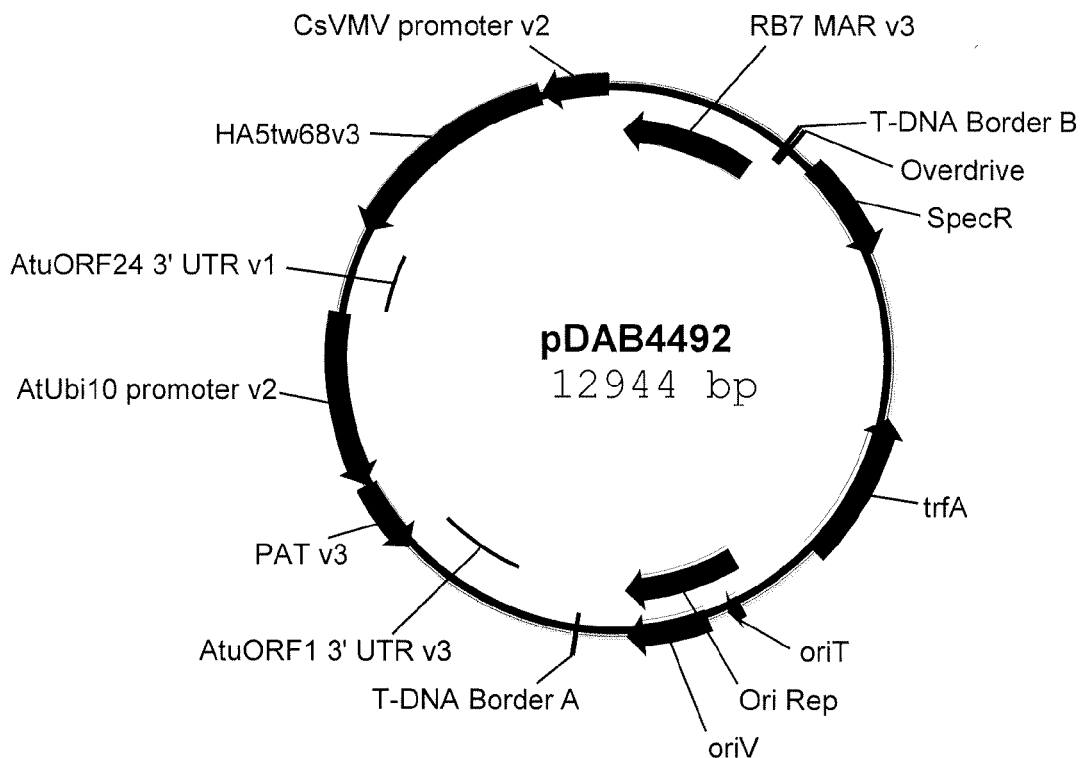
FIGS. 9-15 illustrate gene designs of various plant targeted constructs.
Figure 10:
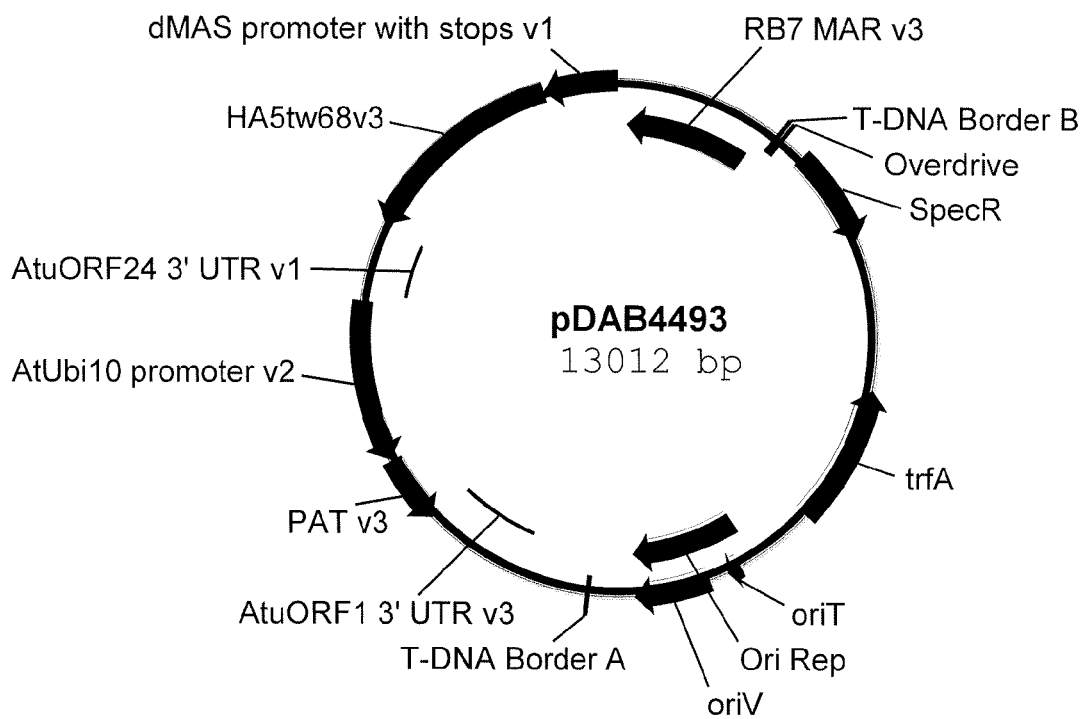
Figure 11A:
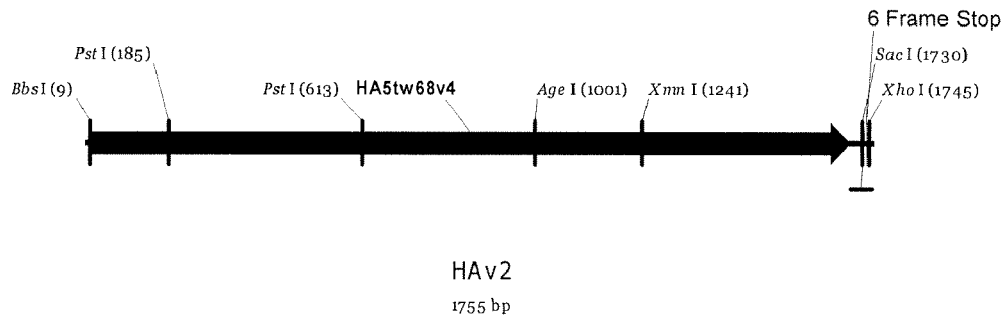
FIGS. 11A (HAv2) and 11B (pDAB4494) depict constructs for SEQ ID NO: 3 (HA5tw68 v4).
Figure 11B:
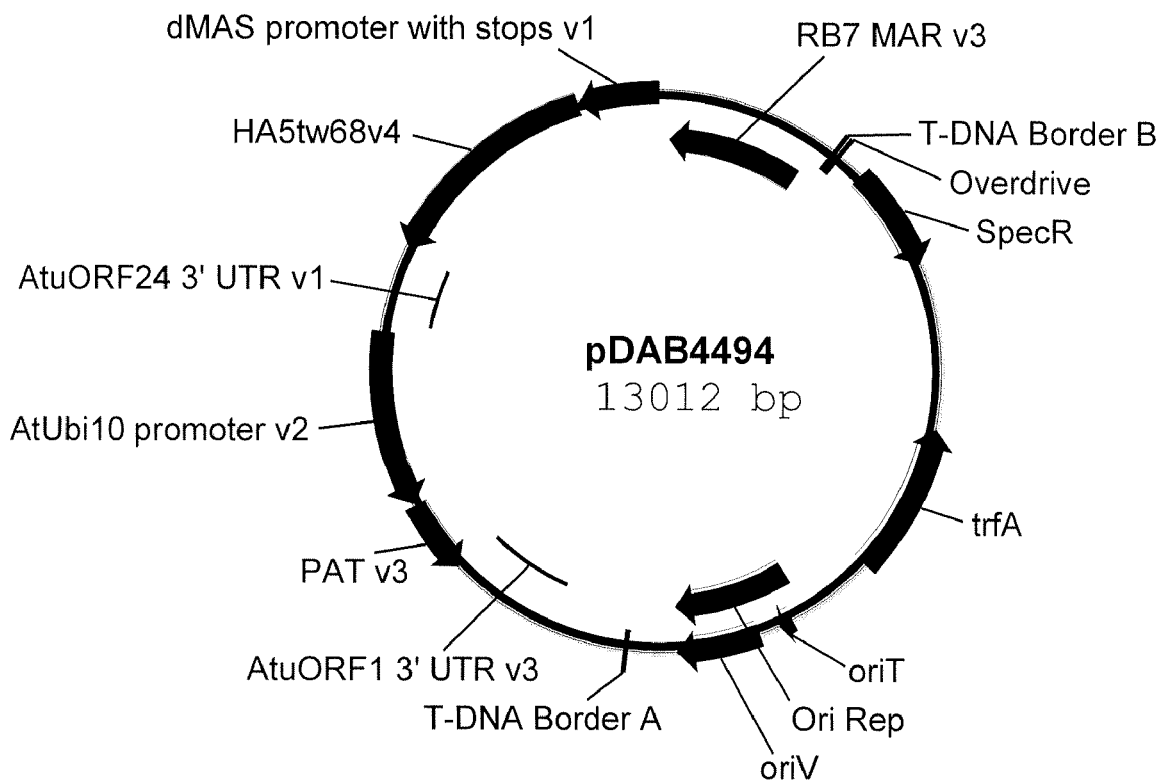
Figure 12A:
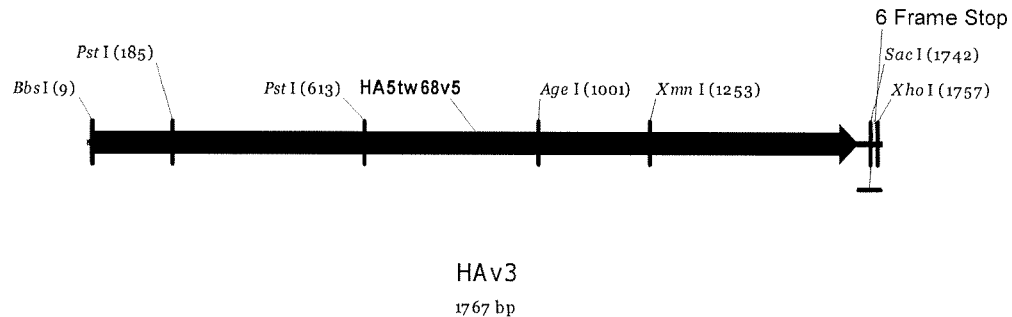
FIGS. 12A (HAv3) and 12B (pDAB4495) depict constructs for SEQ ID NO: 5 (HA5tw68 v5).
Figure 12B:
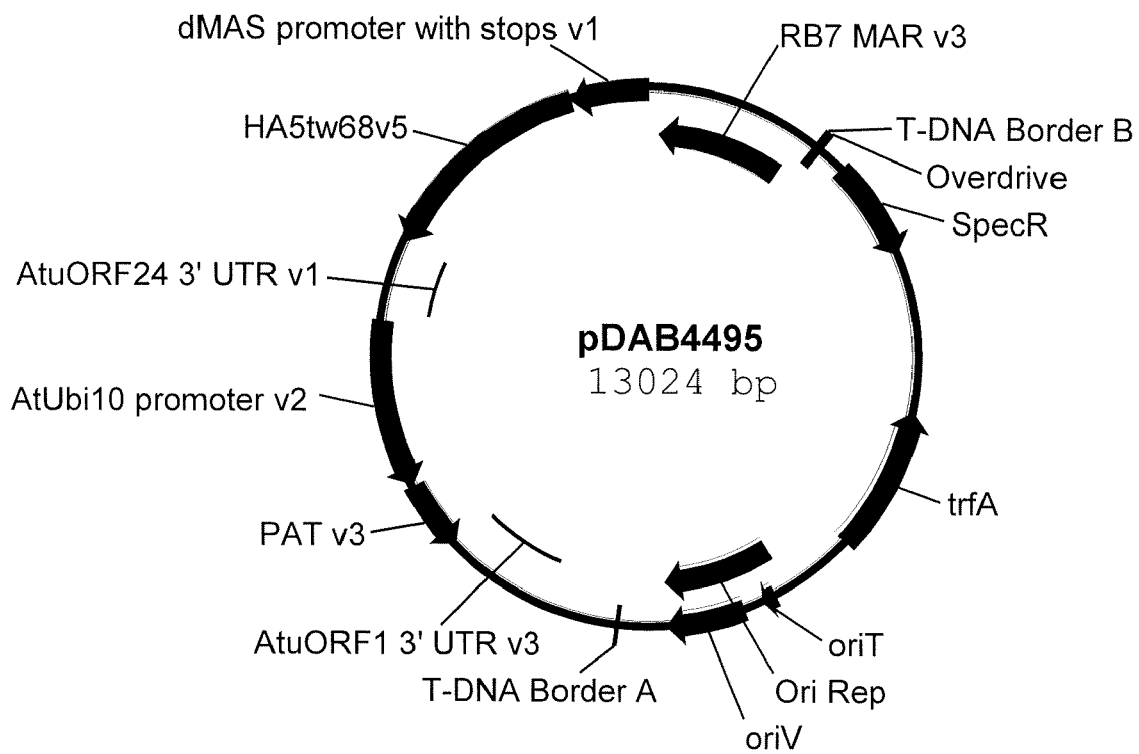
Figure 13A:
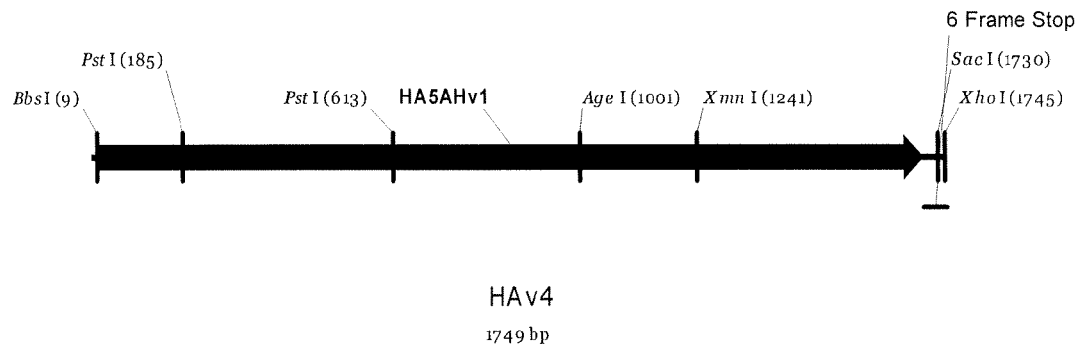
FIGS. 13A (HAv4) and 13B (pDAB4496) depict constructs for SEQ ID NO: 7 (HA5AH v1).
Figure 13B:
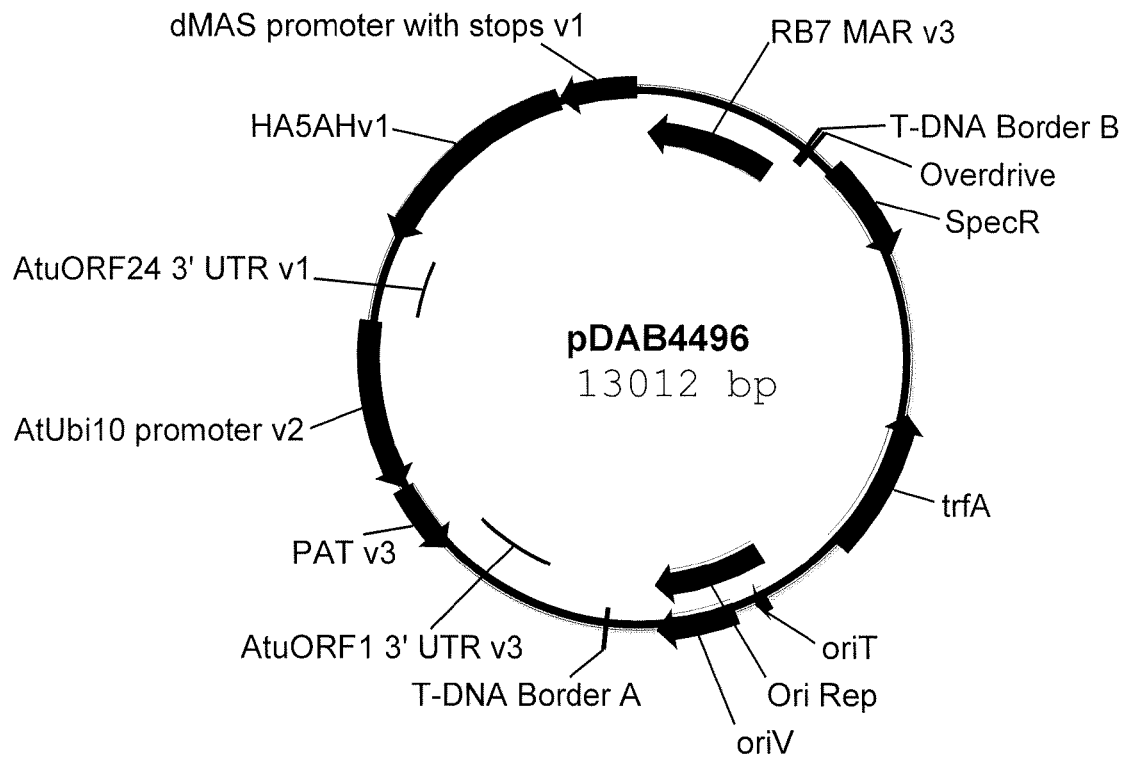
Figure 14A:
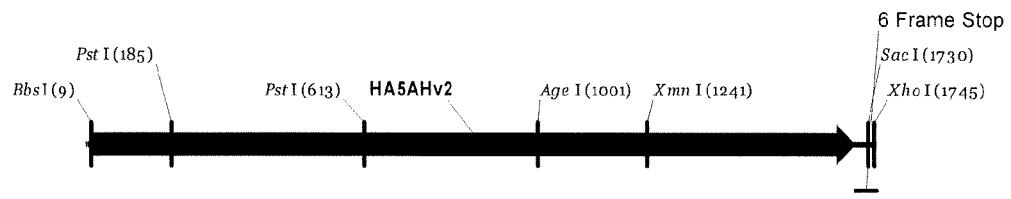
FIGS. 14A (HAv5) and 14B (pDAB4497) depict constructs for SEQ ID NO: 9 (HA5AH v2).
Figure 14B:
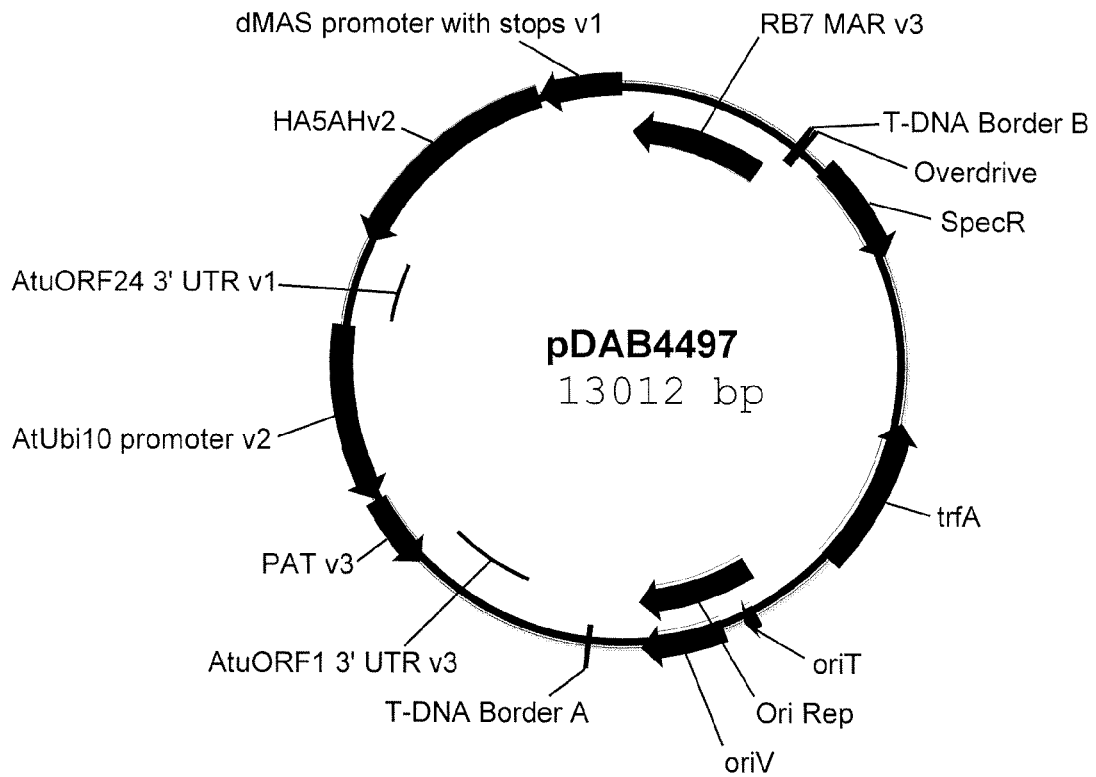
Figure 15A:
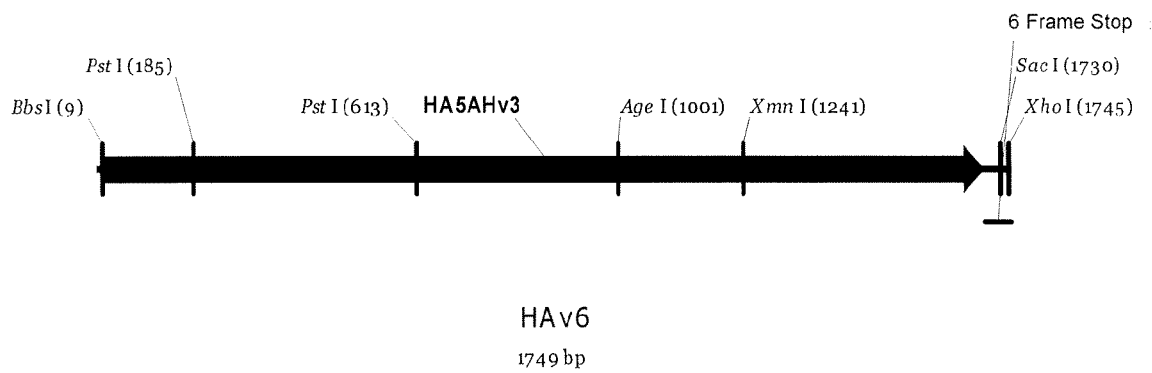
FIGS. 15A (HAv6) and 15B (pDAB4498) depict constructs for SEQ ID NO: 11 (HA5AH v3).
Figure 15B:
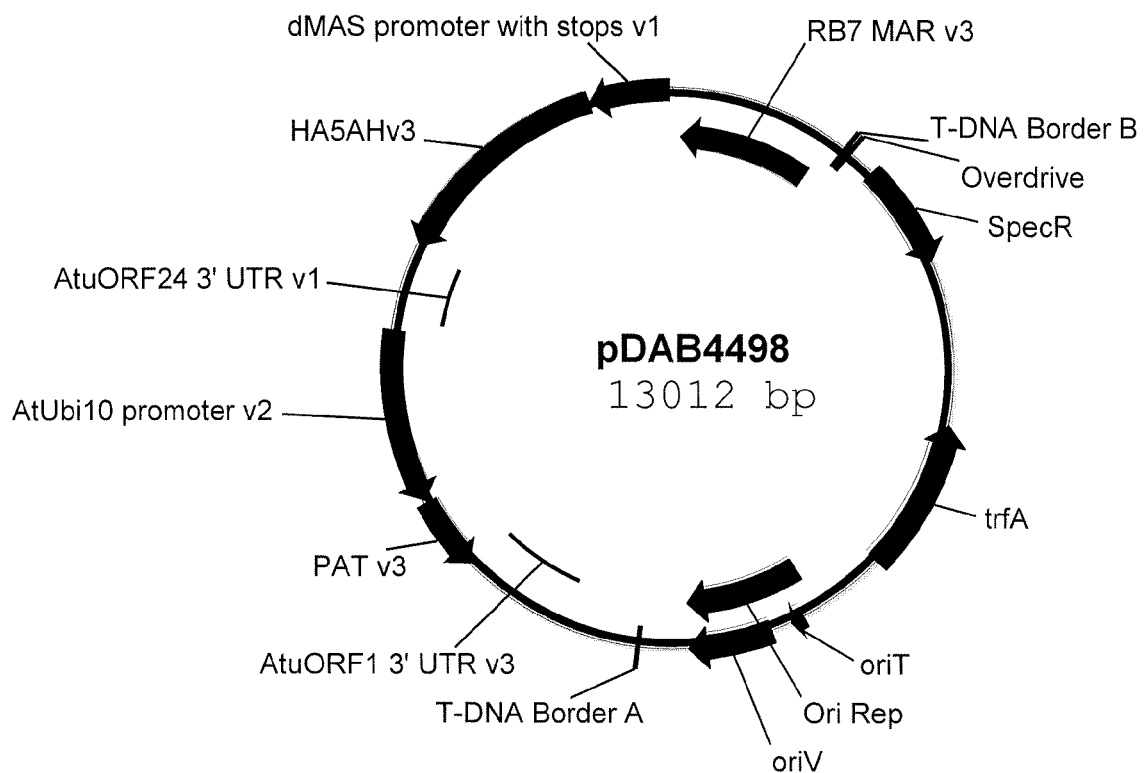

The HA genes including the modified Turkey Wisconsin 68 strain as well as the consensus sequence Ancestral gene with modification were cloned into vectors for DNA vaccines. The HA genes from pDAB4493-4498 were PCR amplified using primers AI 11 (5'-GCTAGCGGCCGCAATGCAGATTCTG-CATTGAA-3') (SEQ ID NO: 15) which contains a Hind III site and AI 12 (5'-GCATAAGCTTCCATGGAGAGGAT-TGTGAT-3') (SEQ ID NO: 16) which contains a Not I site. The PCR products were gel purified (Qiagen kit), digested with Hind III and Not I and ligated into the multi cloning site of pcDNA3 (Invitrogen) digested with Hind III and Not I. The resulting constructs were confirmed by restriction enzyme digest, PCR and sequencing. The positive control pCI-PR8 was supplied by Lorena Brown University of Melbourne, Melbourne Australia. pCI-PR8 contains the HA gene from A/PR/8/34 (PR8)— accession number AF389118. Ten BALBc mice/group (in 2× replicates of five), were intramuscularly immunized with 100 μg of the DNA vaccine on days 0 and 10 and bled on days 14, 28, 56 and 84. Antibody response to PR-8 HA was detected by standard ELISA techniques by coating microtiter plates with 5 μg PR-8 HA/well and is illustrated in FIG. 7.

Example 5

DNA Transfection of Animal Cells

Transfections were carried out on human 293T cells using the Polyethylenimine (PEI) method. Briefly, cells were seeded in 6-well plates in DMEM containing 10% fetal calf serum (TC media) and grown overnight at 37 C, 5% $CO_2$. The following day when the cells were 70-80% confluent the media was removed and replaced with 1 ml of new TC media and incubated for 1 hour at 37 C, 5% $CO_2$. During this incubation the reaction mix was prepared per well as follows: 2 μg DNA, 9 ul PEI in a total volume of 200 ul plain DMEM. The reaction mix was vortexed and incubated for 10-20 min at room temperature. 200 ul was added to each well and the plates incubated for 48 hr at 37 C, 5% $CO_2$. 24 hr into the incubation the wells were washed with PBS and 2 ml new TC media added. The transfections were harvested by removing the media, washing with PBS and resuspending the cells in 500 ul PBS containing 5 mM EDTA (PBSE). The cells were then transferred to a 1.5 ml tube, spun down and resuspended in 200 ul PBSE. The cells were subjected to 3× freeze/thaw cycles and Nonidet P40 (NP-40), a nonionic surfactant, was added to a final concentration of 1%.

To determine the ability of the expressed protein to absorb Chicken red blood cells, mammalian cells (293T and Vero) were transfected, followed by a 1-4-h incubation in serum free media. The media is removed followed by the addition of 500 μl 0.5-1% chicken red blood cells. Following incubation for 45 minutes at room temperature, the cells are washed extensively and examined examine microscopically. The ability of the transgenic HA protein to cross link red blood cells shows that the transgenic protein has retained it conformation and ability to bind to sugar moieties on the surface of red blood cells.

-continued

| Construct | Score (293T) - 48 hr | Score (Vero) - 24 hr |
|---|---|---|
| pCI-PR8 Control construct | ++++ | ++++ |
| pcDNA construct alone. | – | – |
| Mock | – | – |
| pcDNA-4493 tw68 plant codons | +++ | +++ |
| pcDNA-4494 tw68 239 S to N | ++ | ++ |
| pcDNA-4495 tw68 + cleavage | – | ++ |
| pcDNA-4496 ancestor 170 NST | – | + |
| pcDNA-4497 ancestor 239 S to N | + | + |
| pcDNA-4498 ancestor 170 NST 239 N | + | – |

Key
++++, High incidence of hemabsorbing cells with many red blood cells attached
+++, Moderately high incidence of hemabsorbing cells with >5 red blood cells attached
++, Moderate incidence of hemabsorbing cells with >5 red blood cells attached
+ Some incidence of hemabsorbing cells with >5 red blood cells attached
– No incidence of hemabsorbing cells detected TABLE 1a

| N-terminal amino acid position for SEQ ID NOs: 2, 4, 8, 10 or 14 (“Y”) | | | | | | | | | | | |
|---|---|---|---|---|---|---|---|---|---|---|---|
| 1 | 50 | 99 | 148 | 197 | 246 | 295 | 344 | 393 | 442 | 491 | 540 |
| 2 | 51 | 100 | 149 | 198 | 247 | 296 | 345 | 394 | 443 | 492 | 541 |
| 3 | 52 | 101 | 150 | 199 | 248 | 297 | 346 | 395 | 444 | 493 | 542 |
| 4 | 53 | 102 | 151 | 200 | 249 | 298 | 347 | 396 | 445 | 494 | 543 |
| 5 | 54 | 103 | 152 | 201 | 250 | 299 | 348 | 397 | 446 | 495 | 544 |
| 6 | 55 | 104 | 153 | 202 | 251 | 300 | 349 | 398 | 447 | 496 | 545 |
| 7 | 56 | 105 | 154 | 203 | 252 | 301 | 350 | 399 | 448 | 497 | 546 |
| 8 | 57 | 106 | 155 | 204 | 253 | 302 | 351 | 400 | 449 | 498 | 547 |
| 9 | 58 | 107 | 156 | 205 | 254 | 303 | 352 | 401 | 450 | 499 | 548 |
| 10 | 59 | 108 | 157 | 206 | 255 | 304 | 353 | 402 | 451 | 500 | 549 |
| 11 | 60 | 109 | 158 | 207 | 256 | 305 | 354 | 403 | 452 | 501 | 550 |
| 12 | 61 | 110 | 159 | 208 | 257 | 306 | 355 | 404 | 453 | 502 | 551 |
| 13 | 62 | 111 | 160 | 209 | 258 | 307 | 356 | 405 | 454 | 503 | 552 |
| 14 | 63 | 112 | 161 | 210 | 259 | 308 | 357 | 406 | 455 | 504 | 553 |
| 15 | 64 | 113 | 162 | 211 | 260 | 309 | 358 | 407 | 456 | 505 | 554 |
| 16 | 65 | 114 | 163 | 212 | 261 | 310 | 359 | 408 | 457 | 506 | 555 |
| 17 | 66 | 115 | 164 | 213 | 262 | 311 | 360 | 409 | 458 | 507 | 556 |
| 18 | 67 | 116 | 165 | 214 | 263 | 312 | 361 | 410 | 459 | 508 | 557 |
| 19 | 68 | 117 | 166 | 215 | 264 | 313 | 362 | 411 | 460 | 509 | 558 |
| 20 | 69 | 118 | 167 | 216 | 265 | 314 | 363 | 412 | 461 | 510 | 559 |
| 21 | 70 | 119 | 168 | 217 | 266 | 315 | 364 | 413 | 462 | 511 | 560 |
| 22 | 71 | 120 | 169 | 218 | 267 | 316 | 365 | 414 | 463 | 512 | |
| 23 | 72 | 121 | 170 | 219 | 268 | 317 | 366 | 415 | 464 | 513 | |
| 24 | 73 | 122 | 171 | 220 | 269 | 318 | 367 | 416 | 465 | 514 | |
| 25 | 74 | 123 | 172 | 221 | 270 | 319 | 368 | 417 | 466 | 515 | |
| 26 | 75 | 124 | 173 | 222 | 271 | 320 | 369 | 418 | 467 | 516 | |
| 27 | 76 | 125 | 174 | 223 | 272 | 321 | 370 | 419 | 468 | 517 | |
| 28 | 77 | 126 | 175 | 224 | 273 | 322 | 371 | 420 | 469 | 518 | |
| 29 | 78 | 127 | 176 | 225 | 274 | 323 | 372 | 421 | 470 | 519 | |
| 30 | 79 | 128 | 177 | 226 | 275 | 324 | 373 | 422 | 471 | 520 | |
| 31 | 80 | 129 | 178 | 227 | 276 | 325 | 374 | 423 | 472 | 521 | |
| 32 | 81 | 130 | 179 | 228 | 277 | 326 | 375 | 424 | 473 | 522 | |
| 33 | 82 | 131 | 180 | 229 | 278 | 327 | 376 | 425 | 474 | 523 | |
| 34 | 83 | 132 | 181 | 230 | 279 | 328 | 377 | 426 | 475 | 524 | |
| 35 | 84 | 133 | 182 | 231 | 280 | 329 | 378 | 427 | 476 | 525 | |
| 36 | 85 | 134 | 183 | 232 | 281 | 330 | 379 | 428 | 477 | 526 | |
| 37 | 86 | 135 | 184 | 233 | 282 | 331 | 380 | 429 | 478 | 527 | |
| 38 | 87 | 136 | 185 | 234 | 283 | 332 | 381 | 430 | 479 | 528 | |
| 39 | 88 | 137 | 186 | 235 | 284 | 333 | 382 | 431 | 480 | 529 | |
| 40 | 89 | 138 | 187 | 236 | 285 | 334 | 383 | 432 | 481 | 530 | |
| 41 | 90 | 139 | 188 | 237 | 286 | 335 | 384 | 433 | 482 | 531 | |
| 42 | 91 | 140 | 189 | 238 | 287 | 336 | 385 | 434 | 483 | 532 | |
| 43 | 92 | 141 | 190 | 239 | 288 | 337 | 386 | 435 | 484 | 533 | |
| 44 | 93 | 142 | 191 | 240 | 289 | 338 | 387 | 436 | 485 | 534 | |
| 45 | 94 | 143 | 192 | 241 | 290 | 339 | 388 | 437 | 486 | 535 | |
| 46 | 95 | 144 | 193 | 242 | 291 | 340 | 389 | 438 | 487 | 536 | |
| 47 | 96 | 145 | 194 | 243 | 292 | 341 | 390 | 439 | 488 | 537 | |
| 48 | 97 | 146 | 195 | 244 | 293 | 342 | 391 | 440 | 489 | 538 | |
| 49 | 98 | 147 | 196 | 245 | 294 | 343 | 392 | 441 | 490 | 539 | |

TABLE 1b

| C-terminal amino acid position for SEQ ID NOs: 2, 4, 8, 10 or 14 (“Z”) | | | | | | | | | | | |
|---|---|---|---|---|---|---|---|---|---|---|---|
| 5 | 54 | 103 | 152 | 201 | 250 | 299 | 348 | 397 | 446 | 495 | 544 |
| 6 | 55 | 104 | 153 | 202 | 251 | 300 | 349 | 398 | 447 | 496 | 545 |

TABLE 1b-continued

C-terminal amino acid position for SEQ ID NOs: 2, 4, 8, 10 or 14 ("Z")

| | | | | | | | | | | | |
|---|---|---|---|---|---|---|---|---|---|---|---|
| 7 | 56 | 105 | 154 | 203 | 252 | 301 | 350 | 399 | 448 | 497 | 546 |
| 8 | 57 | 106 | 155 | 204 | 253 | 302 | 351 | 400 | 449 | 498 | 547 |
| 9 | 58 | 107 | 156 | 205 | 254 | 303 | 352 | 401 | 450 | 499 | 548 |
| 10 | 59 | 108 | 157 | 206 | 255 | 304 | 353 | 402 | 451 | 500 | 549 |
| 11 | 60 | 109 | 158 | 207 | 256 | 305 | 354 | 403 | 452 | 501 | 550 |
| 12 | 61 | 110 | 159 | 208 | 257 | 306 | 355 | 404 | 453 | 502 | 551 |
| 13 | 62 | 111 | 160 | 209 | 258 | 307 | 356 | 405 | 454 | 503 | 552 |
| 14 | 63 | 112 | 161 | 210 | 259 | 308 | 357 | 406 | 455 | 504 | 553 |
| 15 | 64 | 113 | 162 | 211 | 260 | 309 | 358 | 407 | 456 | 505 | 554 |
| 16 | 65 | 114 | 163 | 212 | 261 | 310 | 359 | 408 | 457 | 506 | 555 |
| 17 | 66 | 115 | 164 | 213 | 262 | 311 | 360 | 409 | 458 | 507 | 556 |
| 18 | 67 | 116 | 165 | 214 | 263 | 312 | 361 | 410 | 459 | 508 | 557 |
| 19 | 68 | 117 | 166 | 215 | 264 | 313 | 362 | 411 | 460 | 509 | 558 |
| 20 | 69 | 118 | 167 | 216 | 265 | 314 | 363 | 412 | 461 | 510 | 559 |
| 21 | 70 | 119 | 168 | 217 | 266 | 315 | 364 | 413 | 462 | 511 | 560 |
| 22 | 71 | 120 | 169 | 218 | 267 | 316 | 365 | 414 | 463 | 512 | 561 |
| 23 | 72 | 121 | 170 | 219 | 268 | 317 | 366 | 415 | 464 | 513 | 562 |
| 24 | 73 | 122 | 171 | 220 | 269 | 318 | 367 | 416 | 465 | 514 | 563 |
| 25 | 74 | 123 | 172 | 221 | 270 | 319 | 368 | 417 | 466 | 515 | 564 |
| 26 | 75 | 124 | 173 | 222 | 271 | 320 | 369 | 418 | 467 | 516 | |
| 27 | 76 | 125 | 174 | 223 | 272 | 321 | 370 | 419 | 468 | 517 | |
| 28 | 77 | 126 | 175 | 224 | 273 | 322 | 371 | 420 | 469 | 518 | |
| 29 | 78 | 127 | 176 | 225 | 274 | 323 | 372 | 421 | 470 | 519 | |
| 30 | 79 | 128 | 177 | 226 | 275 | 324 | 373 | 422 | 471 | 520 | |
| 31 | 80 | 129 | 178 | 227 | 276 | 325 | 374 | 423 | 472 | 521 | |
| 32 | 81 | 130 | 179 | 228 | 277 | 326 | 375 | 424 | 473 | 522 | |
| 33 | 82 | 131 | 180 | 229 | 278 | 327 | 376 | 425 | 474 | 523 | |
| 34 | 83 | 132 | 181 | 230 | 279 | 328 | 377 | 426 | 475 | 524 | |
| 35 | 84 | 133 | 182 | 231 | 280 | 329 | 378 | 427 | 476 | 525 | |
| 36 | 85 | 134 | 183 | 232 | 281 | 330 | 379 | 428 | 477 | 526 | |
| 37 | 86 | 135 | 184 | 233 | 282 | 331 | 380 | 429 | 478 | 527 | |
| 38 | 87 | 136 | 185 | 234 | 283 | 332 | 381 | 430 | 479 | 528 | |
| 39 | 88 | 137 | 186 | 235 | 284 | 333 | 382 | 431 | 480 | 529 | |
| 40 | 89 | 138 | 187 | 236 | 285 | 334 | 383 | 432 | 481 | 530 | |
| 41 | 90 | 139 | 188 | 237 | 286 | 335 | 384 | 433 | 482 | 531 | |
| 42 | 91 | 140 | 189 | 238 | 287 | 336 | 385 | 434 | 483 | 532 | |
| 43 | 92 | 141 | 190 | 239 | 288 | 337 | 386 | 435 | 484 | 533 | |
| 44 | 93 | 142 | 191 | 240 | 289 | 338 | 387 | 436 | 485 | 534 | |
| 45 | 94 | 143 | 192 | 241 | 290 | 339 | 388 | 437 | 486 | 535 | |
| 46 | 95 | 144 | 193 | 242 | 291 | 340 | 389 | 438 | 487 | 536 | |
| 47 | 96 | 145 | 194 | 243 | 292 | 341 | 390 | 439 | 488 | 537 | |
| 48 | 97 | 146 | 195 | 244 | 293 | 342 | 391 | 440 | 489 | 538 | |
| 49 | 98 | 147 | 196 | 245 | 294 | 343 | 392 | 441 | 490 | 539 | |
| 50 | 99 | 148 | 197 | 246 | 295 | 344 | 393 | 442 | 491 | 540 | |
| 51 | 100 | 149 | 198 | 247 | 296 | 345 | 394 | 443 | 492 | 541 | |
| 52 | 101 | 150 | 199 | 248 | 297 | 346 | 395 | 444 | 493 | 542 | |
| 53 | 102 | 151 | 200 | 249 | 298 | 347 | 396 | 445 | 494 | 543 | |

TABLE 2a

N-terminal amino acid position for SEQ ID NO: 6 ("Y")

| | | | | | | | | | | | |
|---|---|---|---|---|---|---|---|---|---|---|---|
| 1 | 50 | 99 | 148 | 197 | 246 | 295 | 344 | 393 | 442 | 491 | 540 |
| 2 | 51 | 100 | 149 | 198 | 247 | 296 | 345 | 394 | 443 | 492 | 541 |
| 3 | 52 | 101 | 150 | 199 | 248 | 297 | 346 | 395 | 444 | 493 | 542 |
| 4 | 53 | 102 | 151 | 200 | 249 | 298 | 347 | 396 | 445 | 494 | 543 |
| 5 | 54 | 103 | 152 | 201 | 250 | 299 | 348 | 397 | 446 | 495 | 544 |
| 6 | 55 | 104 | 153 | 202 | 251 | 300 | 349 | 398 | 447 | 496 | 545 |
| 7 | 56 | 105 | 154 | 203 | 252 | 301 | 350 | 399 | 448 | 497 | 546 |
| 8 | 57 | 106 | 155 | 204 | 253 | 302 | 351 | 400 | 449 | 498 | 547 |
| 9 | 58 | 107 | 156 | 205 | 254 | 303 | 352 | 401 | 450 | 499 | 548 |
| 10 | 59 | 108 | 157 | 206 | 255 | 304 | 353 | 402 | 451 | 500 | 549 |
| 11 | 60 | 109 | 158 | 207 | 256 | 305 | 354 | 403 | 452 | 501 | 550 |
| 12 | 61 | 110 | 159 | 208 | 257 | 306 | 355 | 404 | 453 | 502 | 551 |
| 13 | 62 | 111 | 160 | 209 | 258 | 307 | 356 | 405 | 454 | 503 | 552 |
| 14 | 63 | 112 | 161 | 210 | 259 | 308 | 357 | 406 | 455 | 504 | 553 |
| 15 | 64 | 113 | 162 | 211 | 260 | 309 | 358 | 407 | 456 | 505 | 554 |
| 16 | 65 | 114 | 163 | 212 | 261 | 310 | 359 | 408 | 457 | 506 | 555 |
| 17 | 66 | 115 | 164 | 213 | 262 | 311 | 360 | 409 | 458 | 507 | 556 |
| 18 | 67 | 116 | 165 | 214 | 263 | 312 | 361 | 410 | 459 | 508 | 557 |
| 19 | 68 | 117 | 166 | 215 | 264 | 313 | 362 | 411 | 460 | 509 | 558 |
| 20 | 69 | 118 | 167 | 216 | 265 | 314 | 363 | 412 | 461 | 510 | 559 |
| 21 | 70 | 119 | 168 | 217 | 266 | 315 | 364 | 413 | 462 | 511 | 560 |
| 22 | 71 | 120 | 169 | 218 | 267 | 316 | 365 | 414 | 463 | 512 | 561 |
| 23 | 72 | 121 | 170 | 219 | 268 | 317 | 366 | 415 | 464 | 513 | 562 |

TABLE 2a-continued

| \multicolumn{11}{c}{N-terminal amino acid position for SEQ ID NO: 6 ("Y")} |

| 24 | 73 | 122 | 171 | 220 | 269 | 318 | 367 | 416 | 465 | 514 | 563 |
|----|----|-----|-----|-----|-----|-----|-----|-----|-----|-----|-----|
| 25 | 74 | 123 | 172 | 221 | 270 | 319 | 368 | 417 | 466 | 515 | 564 |
| 26 | 75 | 124 | 173 | 222 | 271 | 320 | 369 | 418 | 467 | 516 |     |
| 27 | 76 | 125 | 174 | 223 | 272 | 321 | 370 | 419 | 468 | 517 |     |
| 28 | 77 | 126 | 175 | 224 | 273 | 322 | 371 | 420 | 469 | 518 |     |
| 29 | 78 | 127 | 176 | 225 | 274 | 323 | 372 | 421 | 470 | 519 |     |
| 30 | 79 | 128 | 177 | 226 | 275 | 324 | 373 | 422 | 471 | 520 |     |
| 31 | 80 | 129 | 178 | 227 | 276 | 325 | 374 | 423 | 472 | 521 |     |
| 32 | 81 | 130 | 179 | 228 | 277 | 326 | 375 | 424 | 473 | 522 |     |
| 33 | 82 | 131 | 180 | 229 | 278 | 327 | 376 | 425 | 474 | 523 |     |
| 34 | 83 | 132 | 181 | 230 | 279 | 328 | 377 | 426 | 475 | 524 |     |
| 35 | 84 | 133 | 182 | 231 | 280 | 329 | 378 | 427 | 476 | 525 |     |
| 36 | 85 | 134 | 183 | 232 | 281 | 330 | 379 | 428 | 477 | 526 |     |
| 37 | 86 | 135 | 184 | 233 | 282 | 331 | 380 | 429 | 478 | 527 |     |
| 38 | 87 | 136 | 185 | 234 | 283 | 332 | 381 | 430 | 479 | 528 |     |
| 39 | 88 | 137 | 186 | 235 | 284 | 333 | 382 | 431 | 480 | 529 |     |
| 40 | 89 | 138 | 187 | 236 | 285 | 334 | 383 | 432 | 481 | 530 |     |
| 41 | 90 | 139 | 188 | 237 | 286 | 335 | 384 | 433 | 482 | 531 |     |
| 42 | 91 | 140 | 189 | 238 | 287 | 336 | 385 | 434 | 483 | 532 |     |
| 43 | 92 | 141 | 190 | 239 | 288 | 337 | 386 | 435 | 484 | 533 |     |
| 44 | 93 | 142 | 191 | 240 | 289 | 338 | 387 | 436 | 485 | 534 |     |
| 45 | 94 | 143 | 192 | 241 | 290 | 339 | 388 | 437 | 486 | 535 |     |
| 46 | 95 | 144 | 193 | 242 | 291 | 340 | 389 | 438 | 487 | 536 |     |
| 47 | 96 | 145 | 194 | 243 | 292 | 341 | 390 | 439 | 488 | 537 |     |
| 48 | 97 | 146 | 195 | 244 | 293 | 342 | 391 | 440 | 489 | 538 |     |
| 49 | 98 | 147 | 196 | 245 | 294 | 343 | 392 | 441 | 490 | 539 |     |

TABLE 2b

| \multicolumn{11}{c}{C-terminal amino acid position for SEQ ID NO: 6 ("Z")} |

| 5  | 54 | 103 | 152 | 201 | 250 | 299 | 348 | 397 | 446 | 495 | 544 |
|----|----|-----|-----|-----|-----|-----|-----|-----|-----|-----|-----|
| 6  | 55 | 104 | 153 | 202 | 251 | 300 | 349 | 398 | 447 | 496 | 545 |
| 7  | 56 | 105 | 154 | 203 | 252 | 301 | 350 | 399 | 448 | 497 | 546 |
| 8  | 57 | 106 | 155 | 204 | 253 | 302 | 351 | 400 | 449 | 498 | 547 |
| 9  | 58 | 107 | 156 | 205 | 254 | 303 | 352 | 401 | 450 | 499 | 548 |
| 10 | 59 | 108 | 157 | 206 | 255 | 304 | 353 | 402 | 451 | 500 | 549 |
| 11 | 60 | 109 | 158 | 207 | 256 | 305 | 354 | 403 | 452 | 501 | 550 |
| 12 | 61 | 110 | 159 | 208 | 257 | 306 | 355 | 404 | 453 | 502 | 551 |
| 13 | 62 | 111 | 160 | 209 | 258 | 307 | 356 | 405 | 454 | 503 | 552 |
| 14 | 63 | 112 | 161 | 210 | 259 | 308 | 357 | 406 | 455 | 504 | 553 |
| 15 | 64 | 113 | 162 | 211 | 260 | 309 | 358 | 407 | 456 | 505 | 554 |
| 16 | 65 | 114 | 163 | 212 | 261 | 310 | 359 | 408 | 457 | 506 | 555 |
| 17 | 66 | 115 | 164 | 213 | 262 | 311 | 360 | 409 | 458 | 507 | 556 |
| 18 | 67 | 116 | 165 | 214 | 263 | 312 | 361 | 410 | 459 | 508 | 557 |
| 19 | 68 | 117 | 166 | 215 | 264 | 313 | 362 | 411 | 460 | 509 | 558 |
| 20 | 69 | 118 | 167 | 216 | 265 | 314 | 363 | 412 | 461 | 510 | 559 |
| 21 | 70 | 119 | 168 | 217 | 266 | 315 | 364 | 413 | 462 | 511 | 560 |
| 22 | 71 | 120 | 169 | 218 | 267 | 316 | 365 | 414 | 463 | 512 | 561 |
| 23 | 72 | 121 | 170 | 219 | 268 | 317 | 366 | 415 | 464 | 513 | 562 |
| 24 | 73 | 122 | 171 | 220 | 269 | 318 | 367 | 416 | 465 | 514 | 563 |
| 25 | 74 | 123 | 172 | 221 | 270 | 319 | 368 | 417 | 466 | 515 | 564 |
| 26 | 75 | 124 | 173 | 222 | 271 | 320 | 369 | 418 | 467 | 516 | 565 |
| 27 | 76 | 125 | 174 | 223 | 272 | 321 | 370 | 419 | 468 | 517 | 566 |
| 28 | 77 | 126 | 175 | 224 | 273 | 322 | 371 | 420 | 469 | 518 | 567 |
| 29 | 78 | 127 | 176 | 225 | 274 | 323 | 372 | 421 | 470 | 519 | 568 |
| 30 | 79 | 128 | 177 | 226 | 275 | 324 | 373 | 422 | 471 | 520 |     |
| 31 | 80 | 129 | 178 | 227 | 276 | 325 | 374 | 423 | 472 | 521 |     |
| 32 | 81 | 130 | 179 | 228 | 277 | 326 | 375 | 424 | 473 | 522 |     |
| 33 | 82 | 131 | 180 | 229 | 278 | 327 | 376 | 425 | 474 | 523 |     |
| 34 | 83 | 132 | 181 | 230 | 279 | 328 | 377 | 426 | 475 | 524 |     |
| 35 | 84 | 133 | 182 | 231 | 280 | 329 | 378 | 427 | 476 | 525 |     |
| 36 | 85 | 134 | 183 | 232 | 281 | 330 | 379 | 428 | 477 | 526 |     |
| 37 | 86 | 135 | 184 | 233 | 282 | 331 | 380 | 429 | 478 | 527 |     |
| 38 | 87 | 136 | 185 | 234 | 283 | 332 | 381 | 430 | 479 | 528 |     |
| 39 | 88 | 137 | 186 | 235 | 284 | 333 | 382 | 431 | 480 | 529 |     |
| 40 | 89 | 138 | 187 | 236 | 285 | 334 | 383 | 432 | 481 | 530 |     |
| 41 | 90 | 139 | 188 | 237 | 286 | 335 | 384 | 433 | 482 | 531 |     |
| 42 | 91 | 140 | 189 | 238 | 287 | 336 | 385 | 434 | 483 | 532 |     |
| 43 | 92 | 141 | 190 | 239 | 288 | 337 | 386 | 435 | 484 | 533 |     |
| 44 | 93 | 142 | 191 | 240 | 289 | 338 | 387 | 436 | 485 | 534 |     |
| 45 | 94 | 143 | 192 | 241 | 290 | 339 | 388 | 437 | 486 | 535 |     |
| 46 | 95 | 144 | 193 | 242 | 291 | 340 | 389 | 438 | 487 | 536 |     |
| 47 | 96 | 145 | 194 | 243 | 292 | 341 | 390 | 439 | 488 | 537 |     |
| 48 | 97 | 146 | 195 | 244 | 293 | 342 | 391 | 440 | 489 | 538 |     |

TABLE 2b-continued

C-terminal amino acid position for SEQ ID NO: 6 ("Z")

| | | | | | | | | | | |
|---|---|---|---|---|---|---|---|---|---|---|
| 49 | 98 | 147 | 196 | 245 | 294 | 343 | 392 | 441 | 490 | 539 |
| 50 | 99 | 148 | 197 | 246 | 295 | 344 | 393 | 442 | 491 | 540 |
| 51 | 100 | 149 | 198 | 247 | 296 | 345 | 394 | 443 | 492 | 541 |
| 52 | 101 | 150 | 199 | 248 | 297 | 346 | 395 | 444 | 493 | 542 |
| 53 | 102 | 151 | 200 | 249 | 298 | 347 | 396 | 445 | 494 | 543 |

TABLE 3a

N-terminal amino acid position for SEQ ID NOs: 12 ("Y")

| | | | | | | | | | | |
|---|---|---|---|---|---|---|---|---|---|---|
| 1 | 50 | 99 | 148 | 197 | 246 | 295 | 344 | 393 | 442 | 491 | 540 |
| 2 | 51 | 100 | 149 | 198 | 247 | 296 | 345 | 394 | 443 | 492 | 541 |
| 3 | 52 | 101 | 150 | 199 | 248 | 297 | 346 | 395 | 444 | 493 | 542 |
| 4 | 53 | 102 | 151 | 200 | 249 | 298 | 347 | 396 | 445 | 494 | 543 |
| 5 | 54 | 103 | 152 | 201 | 250 | 299 | 348 | 397 | 446 | 495 | 544 |
| 6 | 55 | 104 | 153 | 202 | 251 | 300 | 349 | 398 | 447 | 496 | 545 |
| 7 | 56 | 105 | 154 | 203 | 252 | 301 | 350 | 399 | 448 | 497 | 546 |
| 8 | 57 | 106 | 155 | 204 | 253 | 302 | 351 | 400 | 449 | 498 | 547 |
| 9 | 58 | 107 | 156 | 205 | 254 | 303 | 352 | 401 | 450 | 499 | 548 |
| 10 | 59 | 108 | 157 | 206 | 255 | 304 | 353 | 402 | 451 | 500 | 549 |
| 11 | 60 | 109 | 158 | 207 | 256 | 305 | 354 | 403 | 452 | 501 | |
| 12 | 61 | 110 | 159 | 208 | 257 | 306 | 355 | 404 | 453 | 502 | |
| 13 | 62 | 111 | 160 | 209 | 258 | 307 | 356 | 405 | 454 | 503 | |
| 14 | 63 | 112 | 161 | 210 | 259 | 308 | 357 | 406 | 455 | 504 | |
| 15 | 64 | 113 | 162 | 211 | 260 | 309 | 358 | 407 | 456 | 505 | |
| 16 | 65 | 114 | 163 | 212 | 261 | 310 | 359 | 408 | 457 | 506 | |
| 17 | 66 | 115 | 164 | 213 | 262 | 311 | 360 | 409 | 458 | 507 | |
| 18 | 67 | 116 | 165 | 214 | 263 | 312 | 361 | 410 | 459 | 508 | |
| 19 | 68 | 117 | 166 | 215 | 264 | 313 | 362 | 411 | 460 | 509 | |
| 20 | 69 | 118 | 167 | 216 | 265 | 314 | 363 | 412 | 461 | 510 | |
| 21 | 70 | 119 | 168 | 217 | 266 | 315 | 364 | 413 | 462 | 511 | |
| 22 | 71 | 120 | 169 | 218 | 267 | 316 | 365 | 414 | 463 | 512 | |
| 23 | 72 | 121 | 170 | 219 | 268 | 317 | 366 | 415 | 464 | 513 | |
| 24 | 73 | 122 | 171 | 220 | 269 | 318 | 367 | 416 | 465 | 514 | |
| 25 | 74 | 123 | 172 | 221 | 270 | 319 | 368 | 417 | 466 | 515 | |
| 26 | 75 | 124 | 173 | 222 | 271 | 320 | 369 | 418 | 467 | 516 | |
| 27 | 76 | 125 | 174 | 223 | 272 | 321 | 370 | 419 | 468 | 517 | |
| 28 | 77 | 126 | 175 | 224 | 273 | 322 | 371 | 420 | 469 | 518 | |
| 29 | 78 | 127 | 176 | 225 | 274 | 323 | 372 | 421 | 470 | 519 | |
| 30 | 79 | 128 | 177 | 226 | 275 | 324 | 373 | 422 | 471 | 520 | |
| 31 | 80 | 129 | 178 | 227 | 276 | 325 | 374 | 423 | 472 | 521 | |
| 32 | 81 | 130 | 179 | 228 | 277 | 326 | 375 | 424 | 473 | 522 | |
| 33 | 82 | 131 | 180 | 229 | 278 | 327 | 376 | 425 | 474 | 523 | |
| 34 | 83 | 132 | 181 | 230 | 279 | 328 | 377 | 426 | 475 | 524 | |
| 35 | 84 | 133 | 182 | 231 | 280 | 329 | 378 | 427 | 476 | 525 | |
| 36 | 85 | 134 | 183 | 232 | 281 | 330 | 379 | 428 | 477 | 526 | |
| 37 | 86 | 135 | 184 | 233 | 282 | 331 | 380 | 429 | 478 | 527 | |
| 38 | 87 | 136 | 185 | 234 | 283 | 332 | 381 | 430 | 479 | 528 | |
| 39 | 88 | 137 | 186 | 235 | 284 | 333 | 382 | 431 | 480 | 529 | |
| 40 | 89 | 138 | 187 | 236 | 285 | 334 | 383 | 432 | 481 | 530 | |
| 41 | 90 | 139 | 188 | 237 | 286 | 335 | 384 | 433 | 482 | 531 | |
| 42 | 91 | 140 | 189 | 238 | 287 | 336 | 385 | 434 | 483 | 532 | |
| 43 | 92 | 141 | 190 | 239 | 288 | 337 | 386 | 435 | 484 | 533 | |
| 44 | 93 | 142 | 191 | 240 | 289 | 338 | 387 | 436 | 485 | 534 | |
| 45 | 94 | 143 | 192 | 241 | 290 | 339 | 388 | 437 | 486 | 535 | |
| 46 | 95 | 144 | 193 | 242 | 291 | 340 | 389 | 438 | 487 | 536 | |
| 47 | 96 | 145 | 194 | 243 | 292 | 341 | 390 | 439 | 488 | 537 | |
| 48 | 97 | 146 | 195 | 244 | 293 | 342 | 391 | 440 | 489 | 538 | |
| 49 | 98 | 147 | 196 | 245 | 294 | 343 | 392 | 441 | 490 | 539 | |

TABLE 3b

C-terminal amino acid position for SEQ ID NOs: 12 ("Z")

| | | | | | | | | | | |
|---|---|---|---|---|---|---|---|---|---|---|
| 5 | 54 | 103 | 152 | 201 | 250 | 299 | 348 | 397 | 446 | 495 | 544 |
| 6 | 55 | 104 | 153 | 202 | 251 | 300 | 349 | 398 | 447 | 496 | 545 |
| 7 | 56 | 105 | 154 | 203 | 252 | 301 | 350 | 399 | 448 | 497 | 546 |
| 8 | 57 | 106 | 155 | 204 | 253 | 302 | 351 | 400 | 449 | 498 | 547 |
| 9 | 58 | 107 | 156 | 205 | 254 | 303 | 352 | 401 | 450 | 499 | 548 |
| 10 | 59 | 108 | 157 | 206 | 255 | 304 | 353 | 402 | 451 | 500 | 549 |
| 11 | 60 | 109 | 158 | 207 | 256 | 305 | 354 | 403 | 452 | 501 | 550 |
| 12 | 61 | 110 | 159 | 208 | 257 | 306 | 355 | 404 | 453 | 502 | 551 |
| 13 | 62 | 111 | 160 | 209 | 258 | 307 | 356 | 405 | 454 | 503 | 552 |

TABLE 3b-continued

| \multicolumn{11}{c}{C-terminal amino acid position for SEQ ID NOs: 12 ("Z")} |
|---|---|---|---|---|---|---|---|---|---|---|
| 14 | 63 | 112 | 161 | 210 | 259 | 308 | 357 | 406 | 455 | 504 | 553 |
| 15 | 64 | 113 | 162 | 211 | 260 | 309 | 358 | 407 | 456 | 505 |
| 16 | 65 | 114 | 163 | 212 | 261 | 310 | 359 | 408 | 457 | 506 |
| 17 | 66 | 115 | 164 | 213 | 262 | 311 | 360 | 409 | 458 | 507 |
| 18 | 67 | 116 | 165 | 214 | 263 | 312 | 361 | 410 | 459 | 508 |
| 19 | 68 | 117 | 166 | 215 | 264 | 313 | 362 | 411 | 460 | 509 |
| 20 | 69 | 118 | 167 | 216 | 265 | 314 | 363 | 412 | 461 | 510 |
| 21 | 70 | 119 | 168 | 217 | 266 | 315 | 364 | 413 | 462 | 511 |
| 22 | 71 | 120 | 169 | 218 | 267 | 316 | 365 | 414 | 463 | 512 |
| 23 | 72 | 121 | 170 | 219 | 268 | 317 | 366 | 415 | 464 | 513 |
| 24 | 73 | 122 | 171 | 220 | 269 | 318 | 367 | 416 | 465 | 514 |
| 25 | 74 | 123 | 172 | 221 | 270 | 319 | 368 | 417 | 466 | 515 |
| 26 | 75 | 124 | 173 | 222 | 271 | 320 | 369 | 418 | 467 | 516 |
| 27 | 76 | 125 | 174 | 223 | 272 | 321 | 370 | 419 | 468 | 517 |
| 28 | 77 | 126 | 175 | 224 | 273 | 322 | 371 | 420 | 469 | 518 |
| 29 | 78 | 127 | 176 | 225 | 274 | 323 | 372 | 421 | 470 | 519 |
| 30 | 79 | 128 | 177 | 226 | 275 | 324 | 373 | 422 | 471 | 520 |
| 31 | 80 | 129 | 178 | 227 | 276 | 325 | 374 | 423 | 472 | 521 |
| 32 | 81 | 130 | 179 | 228 | 277 | 326 | 375 | 424 | 473 | 522 |
| 33 | 82 | 131 | 180 | 229 | 278 | 327 | 376 | 425 | 474 | 523 |
| 34 | 83 | 132 | 181 | 230 | 279 | 328 | 377 | 426 | 475 | 524 |
| 35 | 84 | 133 | 182 | 231 | 280 | 329 | 378 | 427 | 476 | 525 |
| 36 | 85 | 134 | 183 | 232 | 281 | 330 | 379 | 428 | 477 | 526 |
| 37 | 86 | 135 | 184 | 233 | 282 | 331 | 380 | 429 | 478 | 527 |
| 38 | 87 | 136 | 185 | 234 | 283 | 332 | 381 | 430 | 479 | 528 |
| 39 | 88 | 137 | 186 | 235 | 284 | 333 | 382 | 431 | 480 | 529 |
| 40 | 89 | 138 | 187 | 236 | 285 | 334 | 383 | 432 | 481 | 530 |
| 41 | 90 | 139 | 188 | 237 | 286 | 335 | 384 | 433 | 482 | 531 |
| 42 | 91 | 140 | 189 | 238 | 287 | 336 | 385 | 434 | 483 | 532 |
| 43 | 92 | 141 | 190 | 239 | 288 | 337 | 386 | 435 | 484 | 533 |
| 44 | 93 | 142 | 191 | 240 | 289 | 338 | 387 | 436 | 485 | 534 |
| 45 | 94 | 143 | 192 | 241 | 290 | 339 | 388 | 437 | 486 | 535 |
| 46 | 95 | 144 | 193 | 242 | 291 | 340 | 389 | 438 | 487 | 536 |
| 47 | 96 | 145 | 194 | 243 | 292 | 341 | 390 | 439 | 488 | 537 |
| 48 | 97 | 146 | 195 | 244 | 293 | 342 | 391 | 440 | 489 | 538 |
| 49 | 98 | 147 | 196 | 245 | 294 | 343 | 392 | 441 | 490 | 539 |
| 50 | 99 | 148 | 197 | 246 | 295 | 344 | 393 | 442 | 491 | 540 |
| 51 | 100 | 149 | 198 | 247 | 296 | 345 | 394 | 443 | 492 | 541 |
| 52 | 101 | 150 | 199 | 248 | 297 | 346 | 395 | 444 | 493 | 542 |
| 53 | 102 | 151 | 200 | 249 | 298 | 347 | 396 | 445 | 494 | 543 |

We claim:

1. An isolated, purified, and/or recombinant polypeptide comprising SEQ ID NO: 2 or a fragment of SEQ ID NO: 2, said fragment comprising between 500 and 563 consecutive amino acids of SEQ ID NO: 2.

2. The isolated, purified, and/or recombinant polypeptide according to claim 1, wherein said polypeptide comprises SEQ ID NO: 2.

3. The isolated, purified, and/or recombinant polypeptide according to claim 1, wherein said fragment comprises 500 consecutive amino acids or SEQ ID NO: 2.

4. The isolated polypeptide according to claim 1, wherein said polypeptide fragment comprises 550 consecutive amino acids of SEQ ID NO: 2.

5. A composition comprising a carrier and a polypeptide comprising SEQ ID NO: 2 or a fragment of SEQ ID NO: 2, said fragment comprising between 500 and 563 consecutive amino acids of SEQ ID NO: 2.

6. The composition according to claim 5, wherein said polypeptide comprises SEQ ID NO: 2.

7. The composition according to claim 5, wherein said fragment comprises 500 consecutive amino acids of SEQ ID NO 2.

8. The composition according to claim 5, wherein said polypeptide fragment comprises 550 consecutive amino acids of SEQ ID NO: 2.

* * * * *

UNITED STATES PATENT AND TRADEMARK OFFICE
CERTIFICATE OF CORRECTION

PATENT NO. : 8,163,876 B2
APPLICATION NO. : 12/299404
DATED : April 24, 2012
INVENTOR(S) : Matthew J. Henry, Ignacio M. Larrinua and Sean M. Russell It is certified that error appears in the above-identified patent and that said Letters Patent is hereby corrected as shown below:

Column 11,
Line 36, "Jones *et al.* "Current" should read --Jones *et al.* [1995] "Current--.

Column 34,
Line 5, "25 $\Omega$F" should read --25$\mu$F--.

Signed and Sealed this
Twenty-eighth Day of August, 2012

David J. Kappos
*Director of the United States Patent and Trademark Office*